(12) United States Patent
Schwartz et al.

(10) Patent No.: US 7,670,837 B2
(45) Date of Patent: Mar. 2, 2010

(54) NON-TUMORIGENIC MDCK CELL LINE FOR PROPAGATING VIRUSES

(75) Inventors: Richard Schwartz, San Mateo, CA (US); John Michael Berry, Belmont, CA (US); Ajit Subramanian, Berkeley, CA (US); Xiao Shi, Cupertino, CA (US)

(73) Assignee: Medimmune, LLC, Gaithersburg, MD (US)

( * ) Notice: Subject to any disclaimer, the term of this patent is extended or adjusted under 35 U.S.C. 154(b) by 389 days.

(21) Appl. No.: 11/304,589

(22) Filed: Dec. 16, 2005

(65) Prior Publication Data

US 2006/0188977 A1    Aug. 24, 2006

Related U.S. Application Data

(60) Provisional application No. 60/638,166, filed on Dec. 23, 2004, provisional application No. 60/641,139, filed on Jan. 5, 2005.

(51) Int. Cl.
*C12N 5/00* (2006.01)
*C12N 7/08* (2006.01)
*C12N 5/02* (2006.01)
*C12N 5/16* (2006.01)

(52) U.S. Cl. .................. 435/350; 435/377; 435/375; 435/237; 435/325

(58) Field of Classification Search .................. None
See application file for complete search history.

(56) References Cited

U.S. PATENT DOCUMENTS

| | | | |
|---|---|---|---|
| 5,824,536 | A | 10/1998 | Webster et al. |
| 5,948,410 | A | 9/1999 | Van Scharrenburg et al. |
| 6,455,298 | B1 * | 9/2002 | Groner et al. ............ 435/235.1 |
| 6,656,720 | B2 | 12/2003 | Groner |
| 6,825,036 | B2 | 11/2004 | Makizumi et al. |
| 6,951,752 | B2 | 10/2005 | Reiter et al. |
| 2004/0077086 | A1 | 4/2004 | Reiter et al. |
| 2007/0202527 | A1 | 8/2007 | Wallace et al. |

FOREIGN PATENT DOCUMENTS

| | | |
|---|---|---|
| EP | 0891420 B1 | 2/2005 |
| EP | 1739167 A1 | 1/2007 |
| EP | 1862537 A1 | 12/2007 |
| WO | WO-2004-110484 A1 | 12/2004 |
| WO | WO-2005-026333 A1 | 3/2005 |
| WO | WO-2005-113758 A1 | 12/2005 |
| WO | WO-2006-071563 A3 | 12/2006 |

OTHER PUBLICATIONS

ATCC cell line database search accessed on Mar. 23, 2009 <http://www.atcc.org/ATCCAdvancedCatalogSearch/AllCollectionSearch/tabid/454/Default.aspx>.*

American Type Culture Collection Cell Repository, et al. "Registry of Animal Cell Lines: Certified by the Cell Culture Collection Committee: MDCK." (1964) : 1-2.

Bashir, N., et al. "Phospholipids Regulate Growth and Function of MDCK Cells in Hormonally Defined Serum Free Medium." *In Vitro Cell.Dev.Biol.* (1992) 28A: 663-8.

Boerner, P., et al. "Characterization of Chemically and Virally Transformed Variants of Madin-Darby Canine Kidney (MDCK) Epithelial Cells." *J.Cell.Physiol.* (1985) 122: 299-307.

Boerner, P., et al. "Nutrient Transport and Growth Regulation in Kidney Epithelial Cells (MDCK) Cultured in a Defined Medium." *Cold Spring Harbor Conferences on Cell Proliferation.*, 1982. 555-65.Cold Spring Harbor Laboratory.

Brands, R., et al. "Influvac: A Safe Madin Darby Canine Kidney (MDCK) Cell Culture-Based Influenza Vaccine." *Dev.Biol.Stand.* (1999) 98: 93,100; discussion 111.

Coelingh, K., Presentation: "Next Generation Flu Vaccines: Taking a Crack at Vaccine Production using Cell Culture Technology." The Vaccine Discovery and Commercialization Meeting. Philadelphia, PA, USA, May 23, 2006. pp. 1-10.

Dumitrescu, M. R., et al. "A Three Years Experience in using MDCK Cell Line for Influenza Virus Isolation (1979-1981)." *Arch.Roum.Pathol.Exp.Microbiol.* (1981) 40: 313-6.

Furminger, I. "Vaccine Production." *Textbook of Influenza.*, 1998. Chapter 24: 324-32. BlackwellOxford, UK.

Gaush, C. R., et al. "Characterization of an Established Line of Canine Kidney Cells (MDCK)." *Proc.Soc.Exp.Biol.Med.* (1966) 122: 931-5.

Genzel, Y., et al. "Metabolism of MDCK Cells during Cell Growth and Influenza Virus Production in Large-Scale Microcarrier Culture." *Vaccine* (2004) 22: 2202-8.

George, M., and et al. Abstract and Poster Presentation: "Development of a Fully Disposable Platform Process for Cell Culture Production of Cold-Adapted Live Attenuated Influenza Vaccine (CAIV) Strains of FluMist(R)." WillBio-Single-use BioProcessing Components and Systems. Concord, CA, USA, Jul. 16-18, 2007. pp. 1-5.

Ghendon, Y. Z., et al. "Development of Cell Culture (MDCK) Live Cold-Adapted (CA) Attenuated Influenza Vaccine." *Vaccine* (2005) 23: 4678-84.

Halperin, S. A., et al. "Safety and Immunogenicity of a Trivalent, Inactivated, Mammalian Cell Culture-Derived Influenza Vaccine in Healthy Adults, Seniors, and Children." (2002) 20: 1240-7.

(Continued)

*Primary Examiner*—Stacy B Chen
*Assistant Examiner*—Benjamin P Blumel

(57) ABSTRACT

The present invention provides novel MDCK-derived adherent non-tumorigenic cell lines that can be grown in the presence or absence of serum. The cell lines of the present invention are useful for the production of vaccine material (e.g., viruses). More specifically, the cell lines of the present invention are useful for the production of influenza viruses in general and ca/ts influenza viruses in particular. The invention further provides methods and media formulations for the adaptation and cultivation of MDCK cells such that they remain non-tumorigenic. Additionally, the present invention provides methods for the production of vaccine material (e.g., influenza virus) in the novel cell lines of the invention.

8 Claims, 22 Drawing Sheets

OTHER PUBLICATIONS

Johnson, J. B., et al. "Tumorigenicity of Continuous Monkey Cell Lines in in Vivo and in Vitro Systems." *Dev.Biol.Stand.* (1981) 50: 27-35.

Kalbfüss, B., et al. "Harvesting and Concentration of Human Influenza A Virus Produced in Serum-Free Mammalian Cell Culture for the Production of Vaccines." *Biotechnol.Bioeng.* (2007) 97: 73-85.

Kemble, G. Seminar: "Development of LAIV Production in Cell Culture." Meeting with the World Health Organization. Geneva, Switzerland, Jun. 12, 2007. pp. 1-5.

Kessler, N., et al. "Suitability of MDCK Cells Grown in a Serum-Free Medium for Influenza Virus Production." *Dev.Biol.Stand.* (1999) 98: 13,21; discussion 73-4.

Leighton, J., et al. "Clinical and Experimental Tumors of the Kidney in Tissue Culture and in the Chick Embryo." *Eur.J.Cancer* (1972) 8: 281-5.

Leighton, J., et al. "A Cell Line Derived from Normal Dog Kidney (MDCK) Exhibiting Qualities of Papillary Adenocarcinoma and of Renal Tubular Epithelium." *Cancer* (1970) 26: 1022-8.

Leighton, J., et al. "Secretory Activity and Oncogenicity of a Cell Line (MDCK) Derived from Canine Kidney." *Science* (1969) 163: 472-3.

Liu, J., and et al., Abstract and Presentation: "Selection and Characterization of a High Producing Host Cell Line for Influenza Vaccine Production." WillBio Meeting-Cell Engineering and Banking. Washington, DC, USA, Dec. 4-6, 2006. pp. 1-9.

Liu, J., R. Schwartz and et al., Abstract and Presentation: "Development of a Process for Cell Culture Production of a Cold-Adapted Live Attenuated Influenza Vaccine (LAIV)." WillBio Meeting-BioProcess Technology. Amsterdam, Netherlands, Apr. 2-4, 2007. pp. 1-13.

Madin, S. H., et al. "Established Kidney Cell Lines of Normal Adult Bovine and Ovine Origin." *Proc.Soc.Exp.Biol.Med.* (1958) 98: 574-6.

Mani, S., Abstract and Presentation: "Characterization of a Madin Darby Canine Kidney (MDCK) Cell Bank used in the Production of a Live Attenuated Influenza Vaccine (LAIV)." WillBio Meeting-Cell Engineering and Banking. Philadelphia, PA, USA, Dec. 3-5, 2007. pp. 1-8.

Maranga, L., and et al., Abstract and Poster: "Development of a Platform Process for Cell Culture Production of Cold-Adapted Live Attenuated Influenza (CAIV) Strains of FluMist(R)." 20th Meeting of the European Society for Animal Cell Technology (ESACT). Dresden, Germany, Jun. 17-20, 2007. pp. 1-6.

Maranga, L., and et al., Abstract and Presentation: "Development of a Platform Process for Cell Culture Production of Cold-Adapted Live Attenuated Influenza Vaccine." Biochemical Engineering XV. Quebec City, Canada, Jul. 15-19, 2007. pp. 1-7.

Medema, J., et al. "Safety Assessment of Madin Darby Canine Kidney Cells as Vaccine Substrate." *Dev.Biol.(Basel)* (2006) 123: 243,50; discussion 265-6.

MedImmune Vaccines, Inc. "Written Opinion of the International Searching Authority for PCT/US2005/45587 (FL410PCT)." (Jul. 26, 2006) : 1-4.

Merten, O. W., et al. "Production of Influenza Virus in Serum-Free Mammalian Cell Cultures." *Dev.Biol.Stand.* (1999) 98: 23,37; discussion 73-4.

Merten, O. W., et al. *"Production of Influenza Virus in Cell Cultures for Vaccine Preparation." Adv.Exp.Med.Biol.* (1996) 397: 141-51.

Pakes, S. P., et al. "Chromosome Analysis of 2 Canine Tumor Cell Lines." *Am.J.Vet.Res.* (1965) 26: 837-43.

Percheson, P. B., et al. "A Phase I, Randomized Controlled Clinical Trial to Study the Reactogenicity and Immunogenicity of a New Split Influenza Vaccine Derived from a Non-Tumorigenic Cell Line." *Dev. Biol.Stand.* (1999) 98: 127,32; discussion 133-4.

Rindler, M. J., et al. "Retention of Differentiated Properties in an Established Dog Kidney Epithelial Cell Line (MDCK)." *J.Cell Biol.* (1979) 81: 635-48.

Saier, M. H.,Jr, et al. "Studies on Growth Regulation and the Mechanism of Transformation of the Kidney Epithelial Cell Line, MDCK: Importance of Transport Function to Growth." *Prog.Clin.Biol.Res.* (1982) 91: 569-97.

Saier, M. H.,Jr. "Growth and Differentiated Properties of a Kidney Epithelial Cell Line (MDCK)." *Am.J.Physiol.* (1981) 240: C106-9.

Schwartz, R., Abstract and Presentation: "Transitioning from Eggs to Cell Culture Production FluMist(R), a Live Attenuated Influenza Vaccine (LAIV), and Modeling Seasonal and Pandemic Vaccine Production." WillBio Meeting-BioProcess Technology. Singapore, Jul. 30-Aug. 1, 2007. pp. 1-14.

Stiles, C. D., et al. "Growth Control of Heterologous Tissue Culture Cells in the Congenitally Athymic Nude Mouse." *Cancer Res.* (1976) 36: 1353-60.

Stiles, C. D., et al. "Relationship of Cell Growth Behavior in Vitro to Tumorigenicity in Athymic Nude Mice." *Cancer Res.* (1976) 36: 3300-5.

Subramanian, A., and et al., Abstract and Poster: "Developing a Cell Culture Process for Production of Live Attenuated Influenza Virus Vaccine in Madin Darby Canine Kidney Cells." WillBio Meeting-Viral Vectors and Vaccines. Amsterdam, Netherlands, May 25-27, 2005. pp. 1-6.

Subramanian, A., and et al., Presentation: "Developing a Cell Culture Process for Production of a Live Attenuated Influenza Virus Vaccine in Madin Darby Canine Kidney Cells." WillBio Meeting-Viral Vectors and Vaccines. Austin, Texas, USA, Nov. 14-16, 2005. pp. 1-5.

Taub, M., et al. "Alterations in Growth Requirements of Kidney Epithelial Cells in Defined Medium Associated with Malignant Transformation." *J.Supramol.Struct.Cell.Biochem.* (1981) 15: 63-72.

Taub, M., et al. "Growth of Functional Primary Cultures of Kidney Epithelial Cells in Defined Medium." *J.Cell.Physiol.* (1980) 105: 369-78.

Taub, M., et al. "Growth of Madin-Darby Canine Kidney Epithelial Cell (MDCK) Line in Hormone-Supplemented, Serum-Free Medium." *Proc.Natl.Acad.Sci.U.S.A.* (1979) 76: 3338-42.

Taub, M., et al. "An Established but Differentiated Kidney Epithelial Cell Line (MDCK)." *Methods Enzymol.* (1979) 58: 552-60.

Taub, N., et al. "The Development of Serum-Free Hormone-Supplemented Media for Primary Kidney Cultures and their use in Examining Renal Functions." *Ann.N.Y.Acad.Sci.* (1981) 372: 406-21.

Voeten, J. T., et al. "Characterization of High-Growth Reassortant Influenza A Viruses Generated in MDCK Cells Cultured in Serum-Free Medium." *Vaccine* (1999) 17: 1942-50.

Voeten, J. T., et al. "Generation and Characterization of Reassortant Influenza A Viruses Propagated in Serum-Free Cultured MDCK-SF1 Cells." *Dev.Biol.Stand.* (1999) 98: 77,87; discussion 89-90.

Youil, R., et al. "Comparative Study of Influenza Virus Replication in Vero and MDCK Cell Lines." *J.Virol.Methods* (2004) 120: 23-31.

Zambon, M. "Laboratory Diagnosis of Influenza." *Textbook of Influenza.*, 1998. 291-313.Blackwell ScienceOxford.

Tree, J.A. et al., Comparison of large-scale mammalian cell culture system with egg culture for production of influenza virus A vaccine strains, Vaccine, May 2001, 19, 3444-50.

Gibco BRL, A Guide to Serum-Free Cell Culture, on line catalog, published on 2003, Please see catalog of VP-SFM+ 11681-020.

Gendon, IuZ, et al. "Further Development (MDCK) of Live Cold-Adapted Influenza Vaccine: Cultivation of Vaccine Strains in Production Fermenters (English Translation of ref. C10 submitted Feb. 29, 2008)." *Vopr.Virusol.* (2005) 50: 4-9.

Radaeva, I. F., et al. "Development and Certification of Libraries of the MDCK Continuous Cell Line for Production of Influenza Vaccine (English Translation of ref. C34 submitted Feb. 29, 2008)." *Vopr. Virusol.* (2005) 50: 43-6.

U.S. Appl. No. 11/855,769, filed Sep. 14, 2007, Liu, J., et al.

"Guidance for Industry: Characterization and Qualification of Cell Substrates and Other Biological Starting Materials used in the Production of Viral Vaccines for the Prevention and Treatment of Infectious Diseases." (2006) 25: 697-723.

Arthur, J. M. "The MDCK Cell Line is made Up of Populations of Cells with Diverse Resistive and Transport Properties." *Tissue Cell* (2000) 32: 446-50.

Chiron Behring Gmbh. "Use of MDCK Cells for Manufacture of Inactivated Influenza Virus Vaccines. (Briefing Document)." FDA—Vaccines and Related Biological Products Advisory Committee. Bethesda, MD, Nov. 16, 2005. pp. 1-14 (as downloaded Dec. 12, 2008 from http://www.fda.gov/ohrms/dockets/ac/05/briefing/5-4188B1__18.pdf).

Dobbelaer, R. "ICH Guidelines and PhEur Monographs on Derivation and Characterisation of Cell Substrates used for Production of biotechnological/biological Products. International Conference on Harmonisation." *Dev.Biol.Stand.* (1999) 98: 159-65.

Griffiths, E. "WHO Requirements for the use of Animal Cells as in Vitro Substrates for the Production of Biologicals: Application to Influenza Vaccine Production." *Dev.Biol.Stand.* (1999) 98: 153-7.

Lewis, A. M., Jr, et al. "A Defined-Risks Approach to the Regulatory Assessment of the use of Neoplastic Cells as Substrates for Viral Vaccine Manufacture." *Dev.Biol.(Basel)* (2001) 106: 513-35.

Mabrouk, T., et al. "Influenza Vaccine Technologies and the use of the Cell-Culture Process (Cell-Culture Influenza Vaccine)." *Dev.Biol. (Basel)* (2002) 110: 125-34.

MedImmune. "Use of MDCK Cells for Manufacture of Live Attenuated Influenza Virus Vaccines. (Briefing Document)." FDA—Vaccines and Related Biological Products Advisory Committee. Silver Spring, MD, Sep. 25, 2008. pp. 1-5.

MedImmune. "Live, Attenuated Influenza Vaccine Manufactured in MDCK Cells (VRBPAC Presentation)." FDA—Vaccines and Related Biological Products Advisory Committee. Silver Spring, MD, Sep. 25, 2008. pp. 1-29.

MedImmune. "Use of MDCK Cells for Manufacture of Live, Attenuated Influenza Vaccines (VRBPAC Background Summary)." FDA—Vaccines and Related Biological Products Advisory Committee. Silver Spring, MD, Sep. 25, 2008. pp. 1-9.

Nakazato, Y., et al. "Characterization of Subclones of Madin-Darby Canine Kidney Renal Epithelial Cell Line." *Biochim.Biophys.Acta* (1989) 1014: 57-65.

Palker, T., et al. "Protective Efficacy of Intranasal Cold-Adapted Influenza A/New Caledonia/20/99 (H1N1) Vaccines Comprised of Egg- Or Cell Culture-Derived Reassortants." *Virus Res.* (2004) 105: 183-94.

Solvay. "Madin Darby Canine Kidney Continuous Cell Line (Briefing Document)." FDA—Vaccines and Related Biological Products Advisory Committee. Bethesda, MD, Nov. 16, 2005. pp. 1-21(as downloaded Dec. 12, 2008 from http://www.fda.gov/ohrms/dockets/ac/05/briefing/5-4188B1__19a.pdf).

MedImmune Vaccines, Inc. "Extended European Search Report for EP Appn. No. 05857088.8 (PCT/US2005/045587) (FL410EU)." (Feb. 24, 2009): 1-6.

Palache, A. M., et al "Immunogenicity and Reactogenicity of Influenza Subunit Vaccines Produced in MDCK Cells or Fertilized Chicken Eggs." The Journal of infectious diseases 176 Suppl 1 (1997): S20-3.

* cited by examiner

Tektagen Vero Clone 27F9     ATCC MDCK

Day 1

Day 2

Day 3

NON-TUMORIGENIC MDCK CELL LINE FOR PROPAGATING VIRUSES

CROSS REFERENCE TO RELATED APPLICATIONS

This application claims the benefit under 35 U.S.C. §119 (e) of the following U.S. Provisional Application Nos.: 60/638,166 filed Dec. 23, 2004 and 60/641,139 filed Jan. 5, 2005. The priority applications are hereby incorporated by reference herein in their entirety for all purposes.

FIELD OF THE INVENTION

The present invention relates to novel non-tumorigenic MDCK cells, which can be used for the production of vaccine material. The non-tumorigenic MDCK cells may be adapted to serum-free culture medium. The present invention further relates to media formulations and cultivation methods for the propagation of the non-tumorigenic MDCK cells as well as methods for maintaining the non-tumorigenic nature of the cell lines of the invention. The present invention further relates to processes for the production of influenza viruses in cell culture using non-tumorigenic MDCK cells. The present invention also relates to the viruses (e.g., influenza) obtainable by the process described and immunogenic compositions which contain viruses of this type and/or components thereof.

BACKGROUND OF THE INVENTION

Vaccination is the most important public health measure for preventing disease caused by annual epidemics of influenza. The effective use of vaccines is dependent on being able to quickly produce large quantities of vaccine material (e.g., virus) from a stable and easy to cultivate source. The rapid development of vaccines and their abundant availability is critical in combating many human and animal diseases. Delays in producing vaccines and shortfalls in their quantity can cause problems in addressing outbreaks of disease. For example, recent studies suggest that there is cause for concern regarding the long lead times required to produce vaccines against pandemic influenza. See, for example, Wood, J. M., 2001, Philos. Trans. R. Soc. Lond. B. Biol. Sci., 356:1953. Efficient vaccine production requires the growth of large quantities of vaccine material produced in high yields from a host system. Different vaccine materials require different growth conditions in order to obtain acceptable yields. Vaccine material may be produced in embryonated eggs, primary tissue culture cells, or in established cell lines. However, these host systems currently suffer from a number of limitations detailed below.

Embryonated eggs are typically used for influenza vaccine virus production in a time-, labor-, and cost intensive process that necessitates the management of chicken breeding and egg fertilization. In addition, influenza vaccine produced in eggs is contraindicated for persons with egg allergies due to the severe immediate hypersensitivity reaction that can occur. Thus, there has been an effort by the vaccine industry to develop alternative production platforms that do not utilize eggs such as producing influenza vaccine in a cell culture system.

The use of primary tissue culture cells is hampered by the difficulties encountered in developing and maintaining a stable primary cell population. Often established cells lines are used to circumvent the technical limitations of primary cells. However, many of these cell lines are known to be tumorigenic and as such raise safety concerns and are subject to significant regulatory constraints against their use for vaccine production. In fact, the applicable guidelines of the World Health Organization indicate that only a few cell lines are allowed for vaccine production. Additional problems arise from the use of serum and/or protein additives derived from animal or human sources in cell culture media. For example, variability in the quality and composition among lots of additives and the risk of contamination with mycoplasma, viruses, BSE-agents and other infectious agents are well known. In general, serum or serum-derived substances like albumin, transferrin or insulin may contain unwanted agents that can contaminate the culture and the biological products produced from therefrom. Therefore, many groups are working to develop efficient host systems and cultivation conditions that do not require serum or serum derived products.

Consequently, there has been a demand for establishing a non-tumorigenic cell line useful for the production of vaccine materials in a low-cost, highly safe and stable manner preferably in serum-free or in animal protein-free culture conditions. Such a cell system would be particularly useful for the production of influenza vaccine material.

Madin Darby Canine Kidney (MDCK) cells have been traditionally used for the titration of influenza viruses (Zambon M., in *Textbook of Influenza*, ed Nicholson, Webster and Hay, pg 291-313, Blackwell Science (1998)). These cells were established in 1958 from the kidney of a normal male cocker spaniel. The ATCC list the MDCK (CCL 34) line as having been deposited by S. Madin and N. B. Darby however, numerous other lineages of MDCK cells are available. Leighton J and his coworkers published a series of papers (Leighton et al.,1969, Science 163:472; Leighton et al., 1970, Cancer 26:1022 and Leighton et al., 1972 Europ J. Cancer 8:281) documenting the oncogenic characteristics of the MDCK cells. However, the lineage and passage number of the MDCK cells used for these studies was not described and it was already known that MDCK cells from different lineages and different passages showed changes in chromosome numbers and structure (Gaush et al., 1966, *Proc. Soc. Exp. Biol. Med.*, 122: 931) which could result in cells with tumorigenic properties.

Since one of the major considerations for the acceptability of a cell line for vaccine production concerns the potential malignancy of those cells the use of MDCK cells for the production of vaccine material using currently described cell lines is limited. Groner et al. (U.S. Pat. No. 6,656,720) and Makizumi et al. (U.S. Pat. No. 6,825,036) both purport to disclose cell lines derived from MDCK cells which have been adapted to grow in serum-free media in suspension and which can be utilized for the production of influenza virus. However, it has been reported that there is correlation between the loss of anchorage requirement and the transformation of normal animal cells to cells which are tumorigenic (Stiles et al., 1976, *Cancer Res.*, 36:3300). Several groups (Kessler et al., 1999, *Cell Culture Dev Biol Stand*, 98:13; Merten et al., 1999, *Cell Culture Dev Biol Stand*, 98:23 and Tree et al., 2001, *Vaccine*, 19:3444) purport to describe the use of MDCK cells for the large-scale production of influenza virus; however, they do not address the potential transformation of the MDCK cells used.

Citation or discussion of a reference herein shall not be construed as an admission that such is prior art to the present invention. In addition, citation of a patent shall not be construed as an admission of its validity.

SUMMARY OF THE INVENTION

The present invention provides non-tumorigenic MDCK cells which have been adapted to grow in either serum containing or serum-free media formulations including animal protein-free (APF) formulations. In one embodiment, the non-tumorigenic MDCK cells of the invention are adherent. In another embodiment, the non-tumorigenic MDCK cells of the invention have an epithelial morphology. In yet another embodiment, the non-tumorigenic MDCK cells of the invention are adherent and have an epithelial morphology. Tumorigenicity is in one embodiment, determined by the adult nude mouse model (e.g., Stiles et al., 1976, *Cancer Res*, 36:1353, and Example 2 below). Tumorigenicity may also be tested by other assays, for example, by injection into a chick embryo and/or topical application to the chorioallantois (Leighton et al., 1970, *Cancer*, 26:1022).

Viruses that can be grown in the MDCK cells of the invention include but are not limited to negative strand RNA viruses, including but not limited to influenza, RSV, parainfluenza viruses 1, 2 and 3, and human metapneumovirus.

The present invention further provides methods and media formulations useful for the derivation and maintenance of non-tumorigenic MDCK cells. The MDCK cells of the invention are particularly useful for the production of vaccine material such as, for example, viruses.

Other aspects of the invention include methods of producing vaccine material (e.g., virus) by culturing any MDCK cell of the invention, in a suitable culture medium under conditions permitting production of vaccine material and, isolating the material from one or more of the host cell or the medium in which it is grown.

Immunogenic compositions are also features of the invention. For example, immunogenic compositions comprising the vaccine material produced as described above and, optionally, an excipient such as a pharmaceutically acceptable excipient or one or more pharmaceutically acceptable administration component.

Methods of producing immunogenic responses in a subject through administration of an effective amount of one or more above described immunogenic compositions to a subject are also within the current invention. Additionally, methods of prophylactic or therapeutic treatment of a viral infection (e.g., viral influenza) in a subject through administration of one or more above described immunogenic compositions in an amount effective to produce an immunogenic response against the viral infection are also part of the current invention. Subjects for such treatment can include mammals (e.g., humans). Additionally, such methods can also comprise administration of a composition of one or more viruses produced in the MDCK cells of the invention and a pharmaceutically acceptable excipient that is administered to the subject in an amount effect to prophylactically or therapeutically treat the viral infection.

These and other objects and features of the invention will become more fully apparent when the following detailed description is read in conjunction with the accompanying figures appendix.

DETAILED DESCRIPTION OF THE INVENTION

Figure 1A:
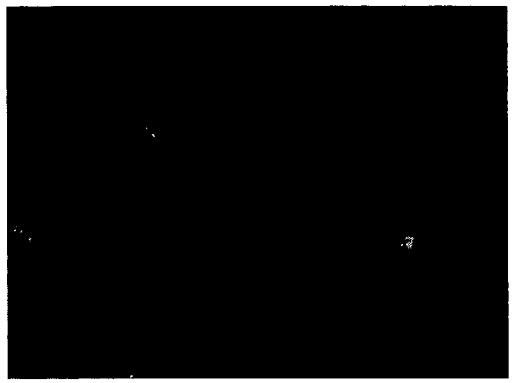
FIG. 1 Growth of Influenza strains in cells. Panel A is a photograph showing the results of a fluorescent focus assay comparing the spread of infection of a representative ca/ts influenza strain in MDCK cells and a Vero Cell Clone (27F9). Panel B is a growth curve of influenza strain ca A/Vietnam/1203/2004 (H5N1) in MDCK cells. Titers peaked at 48 hours post infection at ~8 $\log_{10}$ TCID$_{50}$/mL and remained stable for the next 3 to 4 days.
Figure 1A:
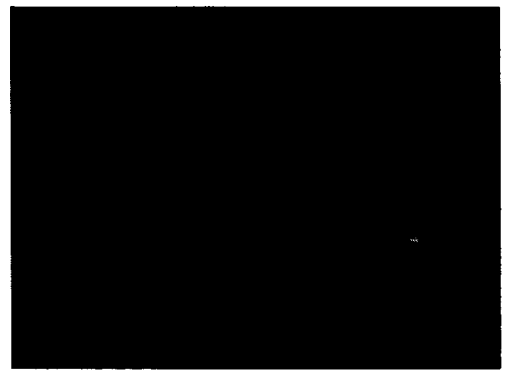
Figure 1A:
Figure 1A:
Figure 1A:
Figure 1A:
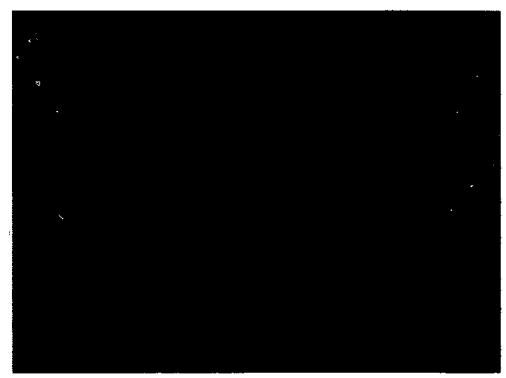
Figure 1B:
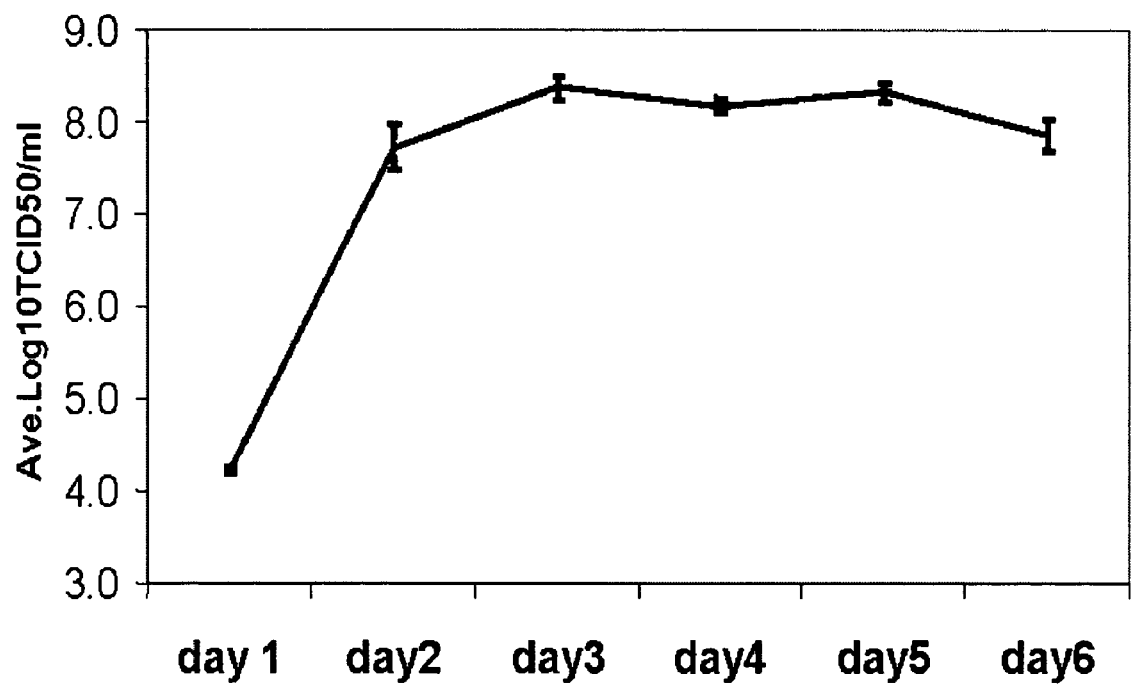

The present invention is based in part on the discovery that MDCK cells can be cultivated under conditions wherein they remain non-tumorigenic. The present invention provides non-tumorigenic cell lines, including MDCK cell lines and other types of cells which have been adapted to a variety of cell culture conditions including serum-free media formulations and are referred to herein as "cells of the invention". In addition, the present invention provides cell culture compositions comprising cells of the invention and other components including, but not limited to, media (e.g., a media disclosed herein), media components, buffers, chemical compounds, additional cell types, viral material (e.g., viral genomes, viral particles) and heterologous proteins. The present invention also provides methods and media formulations useful for the cultivation of non-tumorigenic cells, including MDCK cells, with one more specific characteristics including but not limited to, being non-tumorigenic (e.g., not forming nodules in a nude mouse) and/or growth as adherent cells and/or having an epithelial-like morphology and/or supporting the replication of various viruses including but not limited to orthomyxoviruses, paramyxoviruses, rhabdoviruses and flavoviruses. The culture conditions of the present invention include serum containing and serum-free media formulations, as well as animal protein-free (APF) formulations. In addition, the present invention also provides methods of producing vaccine material (e.g., influenza virus) in non-tumorigenic cells, including MDCK cells, preparing vaccine material from non-tumorigenic cells, and methods of preventing influenza infection utilizing vaccine materials produced in non-tumorigenic cells. The cells of the invention are particularly useful for the production of cold adapted/temperature sensitive/attenuated (ca/ts/att) influenza strains (e.g., those in FluMist®) which do not replicate as efficiently in other mammalian cell lines (e.g., Vero, PerC6, HEK-293, MRC-5 and WI-38 cells).

Cell Characteristics

The cells according to the invention are in one embodiment, vertebrate cells. In another embodiment, the cells of the invention are mammalian cells, e.g., from hamsters, cattle, monkeys or dogs, in particular kidney cells or cell lines derived from these. In still another embodiment, the cells of the invention are MDCK cells (e.g., derived from ATCC CCL-34 MDCK) and are specifically referred to herein as "MDCK cells of the invention" and are encompassed by the term "cells of the invention". In a specific embodiment, the cells of the invention are derived from ATCC CCL-34 MDCK. Cells of the invention may be derived from CCL-34 MDCK cells by methods well known in the art. For example, the CCL-34 MDCK cells may be first passaged a limited number of times in a serum containing media (e.g., Dulbecco's Modified Eagle Medium (DMEM)+10% Fetal Bovine Serum (FBS)+4 mM glutamine+4.5 g/L glucose, or other media described herein) followed by cloning of individual cells and characterization of the clones. Clones with superior biological and physiological properties including, but not limited to, doubling times, tumorigenicity profile and viral production, are selected for the generation of a master cell bank (MCB). In one aspect, the cells of the invention are adapted to growth in a media of choice (e.g., a serum-free or APF media, such as those described herein). Such adaptation may occur prior to, concurrently with, or subsequent to the cloning of individual cells. In certain embodiments, cells of the invention are adapted to grow in MediV SF101, MediV SF102, MediV SF103, MediV SF104 or MediV SF105. Cells of the invention adapted to grow in these media are referred to herein as "MDCK-SF101, MDCK-SF102, MDCK-SF103, MDCK-SF104 and MDCK-SF105" cells, respectively and as "MDCK-SF cells" collectively. In other embodiments, cells of the invention are adapted to grow in serum containing media (e.g., Dulbecco's Modified Eagle Medium (DMEM)+10% Fetal Bovine Serum (FBS)+4 mM glutamine+4.5 g/L glucose), such cells are referred to herein as "MDCK-S" cells. MDCK-SF and MDCK-S cells are also encompassed by the terms "cells of the invention" and "MDCK cells of the invention".

In a specific embodiment of the invention the cells are of the cell lines including, but not limited to, those which have been deposited with the American Type Culture Collection (10801 University Boulevard, Manassas, Va. 20110-2209) and assigned ATCC Deposit Nos. PTA-6500 (Deposited on Jan. 5, 2005), PTA-6501 (Deposited on Jan. 5, 2005), PTA-6502 (Deposited on Jan. 5, 2005), and PTA-6503 (Deposited on Jan. 5, 2005), these cells are referred to herein as "MDCK-S, MDCK-SF101, MDCK-SF102 and MDCK-SF103", respectively and as "the MDCK cells of the invention" collectively. These deposits will be maintained under the terms of the Budapest Treaty on the International Recognition of the Deposit of Microorganisms for the Purposes of Patent Procedure. In one embodiment, the MDCK cells of the invention are used to generate a cell bank useful for the preparation of vaccine material suitable for approval by the U.S. Food and Drug Administration for human use.

The cells lines MDCK-S, MDCK-SF101, MDCK-SF102, MDCK-SF103, MDCK-SF104 and MDCK-SF105 are derived from the cell line MDCK (CCL 34) by passaging and selection with respect to one or more specific characteristics including but not limited to, growing as adherent cells either in serum containing, or serum-free media or animal protein-free media, having an epithelial-like morphology, being non-tumorigenic (e.g., not forming nodules in a nude mouse) and/or supporting the replication of various viruses including but not limited to orthomyxoviruses, paramyxoviruses, rhabdoviruses and flavoviruses.

In one embodiment, the MDCK cells of the invention are non-tumorigenic. Methods for determining if cells are tumorigenic are well known in the art (see, for example, Leighton et al., 1970, *Cancer*, 26:1022 and Stiles et al., 1976, *Cancer Res*, 36:1353), the method currently preferred by the U.S. Food and Drug Administration using the nude mouse model is detailed in Example 2 below. In a specific embodiment, the MDCK cells of the invention are non-tumorigenic in the adult nude mouse model (see, Stiles et al., Id and Example 2 below). In another specific embodiment, the MDCK cells of the invention are non-tumorigenic when injected into a chick embryo and/or topically applied to the chorioallantois (see, Leighton et al., Id). In still another embodiment, the MDCK cells of the invention are non-tumorigenic in the adult nude mouse model but not when injected into a chick embryo and/or topically applied to the chorioallantois. In yet another embodiment, the MDCK cells of the invention are non-tumorigenic in the adult nude mouse model and when injected into a chick embryo and/or topically applied to the chorioallantois. In still another embodiment, the MDCK(cells of the invention are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium. In yet another specific embodiment the medium is a media described herein (e.g., Medi SF103).

Tumorigenicity may be quantified in numerous ways known to one of skill in the art. One method commonly utilized is to determine the "$TD_{50}$" value which is defined as the number of cells required to induce tumors in 50% of the animals tested (see, e.g., Hill R. The $TD_{50}$ assay for tumor cells. In: Potten C, Hendry J, editors. Cell clones. London: Churchill Livingstone; 1985. p. 223). In one embodiment, the MDCK cells of the invention have a $TD_{50}$ value of between about $10^{10}$ to about $10^1$, or between about $10^8$ to about $10^3$, or between about $10^7$ to about $10^4$. In a specific embodiment, the MDCK cells of the invention have a $TD_{50}$ value of more than about $10^{10}$, or of more than about $10^9$, or of more than about $10^8$, or of more than about $10^7$, or of more than about $10^6$, or of more than about $10^5$, or of more than about $10^4$, or of more than about $10^3$, or of more than about $10^2$, or of more than about $10^1$.

In another embodiment, the non-tumorigenic cells of the invention grow as adherent cells either in serum containing or serum-free media or animal protein-free media. In still another embodiment, the non-tumorigenic cells of the invention have an epithelial-like morphology. In yet another embodiment, the MDCK cells of the invention support the replication of various viruses including but not limited to orthomyxoviruses, paramyxoviruses, rhabdoviruses and flavoviruses. It is contemplated that the MDCK cells of the invention may have any combination of one or more specific characteristics including but not limited to, being non-tumorigenic, growing as adherent cells, having an epithelial-like morphology and supporting the replication of various viruses.

It is contemplated that each and every passage of the MDCK cells of the invention is documented in sufficient detail such that the complete lineage of each cell line is available. The documentation of each and every passage may facilitate approval by the U.S. Food and Drug Administration and other regulatory bodies around the world for the use of the MDCK cells of the invention for the preparation of vaccine material.

In another embodiment, the MDCK cells of the invention are free of microbial contaminants (e.g., bacterial, viral and fungal contaminants). Methods for testing for the presence of bacterial and fungal contaminants are well known in the art and routinely performed by commercial contractors (e.g., BioReliance®, Rockville, Md.). Accepted microbial sterility and mycoplasm tests are detailed in Example 2 below. Specific examples of microbial agents which may be tested for are listed in Table 6.

In yet another embodiment, the MDCK cells of the invention support the replication of viruses including but not limited to orthomyxoviruses (including influenza A and/or B strains), paramyxoviruses (including RSV A and/or B, human metapneumovirus and parainfluenza 1, 2 and/or 3), rhabdoviruses and flaboviruses. In a specific embodiment, the MDCK cells of the invention support the replication of cold adapted/temperature sensitive (ca/ts) influenza viruses such as those found, for example, in FluMist® (Belshe et al., 1998, *N Engl J Med* 338:1405; Nichol et al., 1999, *JAMA* 282:137; Jackson et al., 1999, *Vaccine*, 17:1905) and/or reassortant viruses comprising the backbone of these viruses or comprising the backbone (or one or more vRNA segment(s)) of influenza viruses having one or more of the following characteristics: cold adapted, attenuated, and temperature sensitive. One indication of the ability of a cell to support viral replication is the yield of virus obtained from an infected cell culture. Viral yield can be determined by numerous methods known to one skilled in the art. For example, viral yield can be quantified by determining the concentration of virus present in a sample according to a median tissue culture infectious dose ($TCID_{50}$) assay that measures infectious virions. The $TCID_{50}$ values are often reported as the $\log_{10} TCID_{50}/mL$. In one embodiment, the MDCK cells of the invention support the replication of influenza viruses (e.g., ca/ts strains) to a $\log_{10} TCID_{50}/mL$ of at least 6.0, or at least 6.2, or at least 6.4, or at least 6.6, or at least 6.8, or at least 7.0, or at least 7.2, or at least 7.4, or at least 7.6, or at least 7.8, or at least 8.0, or at least 8.2, or at least 8.4, or at least 8.6, or at least 8.8, or at least 9.0, or at least 9.2, or at least 9.4, or at least 9.6, or at least 9.8. In another embodiment, the MDCK cells of the invention support the replication of influenza viruses (e.g., ca/ts strains) to a $\log_{10} TCID_{50}/mL$ of at least about 6.0, or at least about 6.2, or at least about 6.4, or at least about 6.6, or at least about 6.8, or at least about 7.0, or at least about 7.2, or at least about 7.4, or at least about 7.6, or at least about 7.8, or at least about 8.0, or at least about 8.2, or at least about 8.4, or at least about 8.6, or at least about 8.8, or at least about 9.0, or at least about 9.2, or at least about 9.4, or at least about 9.6, or at least about 9.8.

It will be understood by one of skill in the art that the cells of the invention will generally be part of a cell culture composition. The components of a cell culture composition will vary according to the cells and intended use. For example, for cultivation purposes a cell culture composition may comprise cells of the invention and a suitable media for growth of the cells. Accordingly, the present invention provides cell culture compositions comprising cells of the invention and other components including, but not limited to, media (e.g., a media disclosed herein), media components, buffers, chemical compounds, additional cell types, viral material (e.g., viral genomes, viral particles) and heterologous proteins. In one embodiment, a cell culture composition comprises cells of the invention and a media or components thereof. Media which may be present in a cell culture composition include serum-free media, serum containing media and APF media. In one embodiment, a cell composition comprises a media disclosed herein (e.g., MediV SF101, MediV SF102, MediV SF103, MediV SF104 or MediV SF105) or components thereof.

Methods and Media Formulations

The present invention provides methods and media formulations for the cultivation of non-tumorigenic MDCK cells in serum containing media. The present invention also provides methods for the adaptation to and subsequent cultivation of non-tumorigenic MDCK cells in serum-free media including APF media formulations. In certain aspects of the invention, the medias are formulated such that the MDCK cells retain one or more of the following characteristics including but not limited to, being non-tumorigenic, growing as adherent cells, having an epithelial-like morphology and supporting the replication of various viruses when cultured. It is contemplated that the media formulations disclosed herein or components thereof, may be present in a cell culture compostion.

Serum containing media formulations are well known in the art. Serum containing media formulations include but are not limited to, Dulbecco's Modified Eagle Medium (DMEM)+Fetal Bovine Serum (FBS)+glutamine+glucose. In one embodiment, FBS is present in a serum containing media at a concentration between about 1% and about 20%, or between about 5% and about 15%, or between about 5% and about 10%. In a specific embodiment, FBS is present in a serum containing media at a concentration of 10%. In another embodiment, glutamine is present in a serum containing media at a concentration of between about 0.5 mM and about 10 mM, or between about 1 mM and 10 mM, or between about 2 mM and 5 mM. In a specific embodiment, glutamine is present in a serum containing media at a concentration of 4 mM. In still another embodiment, glucose is present in a serum containing media at a concentration of between about 1 g/L and about 10 g/L, or between about 2 g/L and about 5 g/L. In a specific embodiment, glucose is present in a serum containing media at a concentration of 4.5 g/L. In yet another embodiment, a serum containing media formulation comprises, FBS at a concentration between about 1% and about 20%, glutamine at a concentration of between about 0.5 mM and about 10 mM, and glucose a concentration of between about 1 g/L and about 10 g/L. In a specific embodiment, a serum containing media formulation comprises, Dulbecco's Modified Eagle Medium (DMEM)+10% Fetal Bovine Serum (FBS)+4 mM glutamine+4.5 g/L glucose. DMEM is readily available from numerous commercial sources including, for example, Gibco/BRL (Cat. No. 11965-084). FBS is readily available from numerous commercial sources including, for example, JRH Biosciences (Cat. No. 12107-500M). While FBS is the most commonly applied supplement in animal cell culture media, other serum sources are also routinely used and encompassed by the present invention, including newborn calf, horse and human.

In one embodiment, MDCK-S serum adapted non-tumorigenic cells of the invention are derived from Madin Darby Canine Kidney Cells (MDCK) cells obtained from the American type Culture Collection (ATCC CCL34) by culturing them in a chemically defined media supplemented with serum. In a specific embodiment, MDCK cells (ATCC CCL34) are expanded in a chemically defined media supplemented with serum to generate the MDCK-S cell line as follows: The MDCK (ATCC CCL34) cells are passaged as need in Dulbecco's Modified Eagle Medium (DMEM) supplemented with fetal bovine serum (10% v/v), 4 mM glutamine and 4.5 g/L glucose to obtain enough cell to prepare a frozen pre Master Cell Bank (PreMCB) designated MDCK-S. In another specific embodiment, the cells are cultured using the process detailed in Example 2, infra. It is specifically contemplated that the MDCK-S serum adapted cell are passaged for another 20 passages or more, from a vial of PreMCB and tested for tumorigenicity in an vivo adult nude mice model and karyology in a karyotype assay. In certain embodiments, the expanded MDCK-S cells will not produce nodules when injected subcutaneously into adult nude mice and will have a modal chromosome number of 78 with a range of chromosome numbers of no more then about 60-88, or of no more then about 65-85, or of no more than about 65-80, or of no more then about 70-85. In one embodiment, the MDCK-S cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium (e.g., a media described herein).

It will be appreciated by one of skill in the art that the use of serum or animal extracts in tissue culture applications may have drawbacks (Lambert, K. J. et al., In: Animal Cell Biotechnology, Vol 1, Spier, R. E. et al., Eds., Academic Pres New York, pp. 85-122 (1985)). For example, the chemical composition of these supplements may vary between lots, even from a single manufacturer. In addition, supplements of animal or human origin may also be contaminated with adventitious agents (e.g., mycoplasma, viruses, and prions). These agents can seriously undermine the health of the cultured cells when these contaminated supplements are used in cell culture media formulations. Further, these agents may pose a health risk when substances produced in cultures contaminated with adventitious agents are used in cell therapy and other clinical applications. A major fear is the presence of prions which cause spongiform encephalopathies in animals and Creutzfeld-Jakob disease in humans. Accordingly, the present invention further provides serum-free media formulations.

Serum-free media formulations of the invention include but are not limited to MediV SF101 (Taub's+Plant Hydrolysate), MediV SF102 (Taub's+Lipids), MediV SF103 (Taub's+Lipds+Plant Hydrolysate), MediV SF104 (Taub's+Lipds+Plant Hydrolysate+growth factor) and Medi SF105 (same as MediV SF104 except transferrin is replaced with Ferric ammonium citrate/Tropolone or Ferric ammonium sulfate/Tropolone). It is specifically contemplated that Taub's SF medium (Taub and Livingston, 1981, *Ann NY Acad. Sci.*, 372:406) is a 50:50 mixture of DMEM and Ham's F12 supplemented with hormones, 5 µg/mL insulin, 5 µg/mL transferrin, 25 ng/mL prostaglandin E1, 50 nM hydrocortisone, 5 pM triiodthyronine and 10 nM $Na_2SeO_3$, 4.5 g/L glucose, 2.2 g/L $NaHCO_3$ and 4 mM L-glutamine. Taub's SF medium is also referred to herein as Taub's medium or simply "Taub's".

Plant hydrolysates include but are not limited to, hydrolysates from one or more of the following: corn, cottonseed, pea, soy, malt, potato and wheat. Plant hydrolysates may be produced by enzymatic hydrolysis and generally contain a mix of peptides, free amino acids and growth factors. Plant hydrolysates are readily obtained from a number of commercial sources including, for example, Marcor Development, HyClone and Organo Technie. It is also contemplated that yeast hydrolysates my also be utilized instead of, or in combination with plant hydrolysates. Yeast hydrolysates are readily obtained from a number of commercial sources including, for example, Sigma-Aldrich, USB Corp, Gibco/BRL and others.

Lipids that may be used to supplement culture media include but are not limited to chemically defined animal and plant derived lipid supplements as well as synthetically derived lipids. Lipids which may be present in a lipid supplement includes but is not limited to, cholesterol, saturated and/or unsaturated fatty acids (e.g., arachidonic, linoleic, linolenic, myristic, oleic, palmitic and stearic acids). Cholesterol may be present at concentrations between 0.10 mg/ml and 0.40 mg/ml in a 100× stock of lipid supplement. Fatty acids may be present in concentrations between 1 µg/ml and 20 µg/ml in a 100× stock of lipid supplement. Lipids suitable for media formulations are readily obtained from a number of commercial sources including, for example HyClone, Gibco/BRL and Sigma-Aldrich.

In one embodiment, Taub's media is supplemented with a plant hydrolysate and a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L. In a specific embodiment, Taub's media is supplemented with a wheat hydrolysate. In another specific embodiment, Taub's media is supplemented with a wheat hydrolysate at a final concentration of 2.5 g/L. The present invention provides a serum-free media referred to herein as MediV SFM 101 comprising Taub's media supplemented with a wheat hydrolysate at a final concentration of 2.5 g/L.

In another embodiment, Taub's media is supplemented with a lipid mixture at a final concentration of at least 50%, or at least 60%, or at least 70%, or at least 80%, or at least 90%, or at least 100%, or at least 125%, or at least 150%, or at least 200%, or at least 300% of the manufacturers recommended final concentration. In a specific embodiment, Taub's media is supplemented with a chemically defined lipid mixture. In another specific embodiment, Taub's media is supplemented with a chemically defined lipid mixture at a final concentration of 100% of the manufacturers recommended final concentration (e.g., a 100× stock obtained from a manufacture would be add to the media to a final concentration of 1×). The present invention provides a serum-free media referred to herein as MediV SFM 102 comprising Taub's media supplemented with a chemically defined lipid mixture at a final concentration of 100% of the manufacturers recommended final concentration.

In still another embodiment, Taub's media is supplemented with a plant hydrolysate at a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L and with a lipid mixture at a final concentration of at least 50%, or at least 60%, or at least 70%, or at least 80%, or at least 90%, or at least 100%, or at least 125%, or at least 150%, or at least 175%, or at least 200% of the manufacturers recommended concentration. In a specific embodiment, Taub's media is supplemented with wheat hydrolysate and a chemically defined lipid mixture. In another specific embodiment, Taub's media is supplemented with a wheat hydrolysate at a final concentration of 2.5 g/L and a chemically defined lipid mixture at a final concentration of 100% of the manufacturers recommended final concentration. The present invention provides a serum-free media referred to herein as MediV SFM 103 comprising Taub's media supplemented with a wheat hydrolysate at a final concentration of 2.5 g/L and a chemically defined lipid mixture at a final concentration of 100% of the manufacturers recommended final concentration.

In yet another embodiment, Taub's media is supplemented with a growth hormone. Growth hormones which may be used include but are not limited to, Epidermal Growth Factor (EGF), Insulin Growth Factor (IGF), Transforming Growth Factor (TGF) and Fibroblast Growth Factor (FGF). In a particular embodiment, the growth hormone is Epidermal Growth Factor (EGF). In one embodiment, Taub's media is supplemented with a growth factor at a final concentration of between about 0.1 to about 50.0 ng/ml, or between about 0.5 to about 25.0 ng/ml, or between about 1.0 to about 20 ng/ml, or between about 5.0 to about 15.0 ng/ml, or between about 8 ng/ml to about 12 ng/ml. In a specific embodiment, Taub's media is supplemented with a EGF at a final concentration of about 10 ng/ml. In still other embodiments, Taub's media is supplemented with a growth factor at a final concentration of between about 0.1 to about 50.0 ng/ml, or between about 0.5 to about 25.0 ng/ml, or between about 1.0 to about 20 ng/ml, or between about 5.0 to about 15.0 ng/ml, or between about 8 ng/ml to about 12 ng/ml and with a plant hydrolysate at a final concentration of at least 0.5 g/L, or at least 1.0 g/L, or at least 1.5 g/L, or at least 2.0 g/L, or at least 2.5 g/L, or at least 3.0 g/L, or at least 5.0 g/L, or at least 10 g/L, or at least 20 g/L and with a lipid mixture at a final concentration of at least 50%, or at least 60%, or at least 70%, or at least 80%, or at least 90%, or at least 100%, or at least 125%, or at least 150%, or at least 175%, or at least 200% of the manufacturers recommended concentration. In another specific embodiment, Taub's media is supplemented with a wheat hydrolysate at a final concentration of 2.5 g/L and a chemically defined lipid mixture at a final concentration of 100% of the manufacturers recommended final concentration and EGF at a final concentration of about 10 ng/ml. The present invention provides a serum-free media referred to herein as MediV SFM 104 comprising Taub's media supplemented with a wheat hydrolysate at a final concentration of 2.5 g/L and a chemically defined lipid mixture at a final concentration of 100% of the manufacturers recommended final concentration and EGF at a final concentration of about 10 ng/ml.

It will also be appreciated by one skilled in the art that animal protein-free media formulations may be desirable for the production of virus used in the manufacture of vaccines. Accordingly, in certain embodiments one or more or all of the animal derived components of the serum-free media disclosed herein (e.g., MediV SF101, MediV SF102, MediV SF103, MediV SF104 and Medi SF105) is replaced by an animal-free derivative. For example, commercially available recombinant insulin derived from non-animal sources (e.g., Biological Industries Cat. No. 01-818-1) may utilized instead of insulin derived from an animal source. Likewise, iron binding agents (see, e.g., U.S. Pat. Nos. 5,045,454; 5,118,513; 6,593,140; and PCT publication number WO 01/16294) may be utilized instead of transferrin derived from an animal source. In one embodiment, serum-free media formulations of the invention comprise tropolone (2-hydroxy-2,4,6-cyclohepatrien-1) and a source of iron (e.g., ferric ammonium citrate, ferric ammonium sulphate) instead of transferrin. For example, tropolone or a tropolone derivative will be present in an excess molar concentration to the iron present in the medium for at a molar ratio of about 5 to 1 to about 70 to 1, or of about 10 to 1 to about 70 to 1. Accordingly, where the iron concentration in the medium is around 0.3 µM, the tropolone or derivative thereof may be employed at a concentration of about 1.5 µM to about 20 µM, e.g. about 3 µM to about 20 µM. The iron may be present as ferrous or ferric ions, for example resulting from the use of simple or complex iron salts in the medium such as ferrous sulphate, ferric chloride, ferric nitrate or in particular ferric ammonium citrate. The present invention provides a serum-free media referred to herein as MediV SFM 105 comprising Taub's media without transferrin supplemented with a wheat hydrolysate at a final concentration of 2.5 g/L and a chemically defined lipid mixture at a final concentration of 100% of the manufacturers recommended final concentration and EGF at a final concentration of about 10 ng/ml and Ferric ammonium citrate:Tropolone or Ferric ammonium sulfate:Tropolone at a ratio of between 10 to 1 and 70 to 1.

In one embodiment, MDCK-SF101, MDCK-SF102, MDCK-SF103, MDCK-SF104 and MDCK-SF105 serum-free adapted non-tumorigenic cells (collectively referred to herein as MDCK-SF) are derived from Madin Darby Canine Kidney Cells (MDCK) cells obtained from the American type Culture Collection (ATCC CCL34) by culturing in a chemically defined media supplemented with serum for at least one passage and then passaging them in a serum-free media such as, for example, the serum-free medias described supra. In a specific embodiment, MDCK cells (ATCC CCL34) are adapted to serum-free media to generate a MDCK-SF cell line as follows: The MDCK (ATCC CCL34) cells are passaged in Dulbecco's Modified Eagle Medium (DMEM) supplemented with fetal bovine serum (10% v/v), 4 mM glutamine and 4.5 g/L glucose at least once and then passaged in serum-free media. The MDCK-SF cells are then passaged as needed in serum-free media to obtain enough cell to prepare a frozen pre Master Cell Bank (PreMCB). In certain embodiments, the cells are passaged in a serum containing media (e.g., Dulbecco's Modified Eagle Medium (DMEM) supplemented with fetal bovine serum (10% v/v), 4 mM glutamine and 4.5 g/L glucose) between 1 and 5 times, or between 4 and 10 time, or between 9 and 20 times, or more than 20 times, and then passaged in serum-free media (e.g., MediV SF101, MediV SF102, MediV SF103, MediV SF104 and Medi SF105).

It is specifically contemplated that the MDCK-SF serum-free adapted cells are passaged for another 20 passages or more, from a vial of PreMCB and tested for tumorigenicity in an vivo adult nude mice model and karyology in a karyotype assay. In certain embodiments, the expanded MDCK-SF cells will not produce nodules when injected subcutaneously into adult nude mice and/or will have a modal chromosome number of 78. In another embodiment, the expanded MDCK-SF cells will have a modal chromosome number of 78 with a range of chromosome numbers of no more then about 60 to about 88, or of no more then about 65 to about 85, or of no more then about 65-80, or of no more then about 70 to about 85. In one embodiment, the MDCK-SF cells are non-tumorigenic after at least 20 passages, or after at least 30 passages, or after at least 40 passages, or after at least 50 passages, or after at least 60 passages, or after at least 70 passages, or after at least 80 passages, or after at least 90 passages, or after at least 100 passages in a medium (e.g., a media described herein).

In one embodiment, the serum-free media used for the derivation of MDCK-SF cells is MediV SF101. In another embodiment, the serum-free media used for the derivation of MDCK-SF cells is MediV SF102. In yet another embodiment, the serum-free media used for the derivation of MDCK-SF cells is MediV SF103. In still another embodiment, the serum-free media used for the derivation of MDCK-SF cells is MediV-SF104. In another embodiment, the serum-free media used for the derivation of MDCK-SF cells is MediV SF105. In yet another embodiment, the serum-free media used for the derivation of MDCK-SF cells is an APF media. It is contemplated that the media described herein may be formulated to eliminate animal proteins. For example bovine transferrin may be replaced with a recombinant transferrin derived from a non animal source.

Culture Conditions

The present invention provides methods for the cultivation of MDCK cells (preferably non-tumorigenic) and other animal cells (tumorigenic or not) in serum containing and serum-free media formulations (supra). It is specifically contemplated that additional culture conditions may play a role in the maintenance of the MDCK-S and MDCK-SF cells in a non-tumorigenic state. These culture conditions include but are not limited to the choice of adherent surface, cell density, temperature, $CO_2$ concentration, method of cultivation, dissolved oxygen content and pH.

It is specifically contemplated that one skilled in the art may adapt the culture conditions in a number of ways to optimize the growth of the MDCK cells of the invention. Such adaptations may also result in a increase in the production of viral material (e.g., virus), alternatively, one skilled in the art may adapt the culture conditions to optimize the production of vaccine material from the MDCK cells of the invention without regard for the growth of the cells. These culture conditions include but are not limited to adherent surface, cell density, temperature, $CO_2$ concentration, method of cultivation, dissolved oxygen content and pH.

In one embodiment, the MDCK cells of the invention are cultivated as adherent cells on a surface to which they attach. Adherent surfaces on which tissue culture cells can be grown on are well known in the art. Adherent surfaces include but are not limited to, surface modified polystyrene plastics, protein coated surfaces (e.g., fibronectin and/or collagen coated glass/plastic) as well as a large variety of commercially available microcarriers (e.g., DEAE-Dextran microcarrier beads, such as Dormacell, Pfeifer & Langen; Superbead, Flow Laboratories; styrene copolymer-tri-methylamine beads, such as Hillex, SoloHill, Ann Arbor). Microcarrier beads are small spheres (in the range of 100-200 microns in diameter) that provide a large surface area for adherent cell growth per volume of cell culture. For example a single liter of medium can include more than 20 million microcarrier beads providing greater than 8000 square centimeters of growth surface. The choice of adherent surface is determined by the methods utilized for the cultivation of the MDCK cells of the invention and can be determined by one skilled in the art. Suitable culture vessels which can be employed in the course of the process according to the invention are all vessels known to the person skilled in the art, such as, for example, spinner bottles, roller bottles, fermenters or bioreactors. For commercial production of viruses, e.g., for vaccine production, it is often desirable to culture the cells in a bioreactor or fermenter. Bioreactors are available in volumes from under 1 liter to in excess of 100 liters, e.g., Cyto3 Bioreactor (Osmonics, Minnetonka, Minn.); NBS bioreactors (New Brunswick Scientific, Edison, N.J.); laboratory and commercial scale bioreactors from B. Braun Biotech International (B. Braun Biotech, Melsungen, Germany).

In one embodiment, the MDCK cells of the invention are cultivated as adherent cells in a batch culture system. In still another embodiment, the MDCK cells of the invention are cultivated as adherent cells in a perfusion culture system. It is specifically contemplated that the MDCK cells of the invention will be cultured in a perfusion system, (e.g., in a stirred vessel fermenter, using cell retention systems known to the person skilled in the art, such as, for example, centrifugation, filtration, spin filters and the like) for the production of vaccine material (e.g., virus).

In one embodiment, the MDCK cells of the invention are cultivated at a $CO_2$ concentration of at least 1%, or of at least 2%, or of at least 3%, or of at least 4%, or of at least 5%, or of at least 6%, or of at least 7%, or of at least 8%, or of at least 9%, or of at least 10%, or of at least 20%.

In one embodiment the dissolved oxygen (DO) concentration ($pO_2$ value) is advantageously regulated during the cultivation of the MDCK cells of the invention and is in the range from 5% and 95% (based on the air saturation), or between 10% and 60%. In a specific embodiment the dissolved oxygen (DO) concentration ($pO_2$ value) is at least 10%, or at least 20%, or at least 30%, or at least 50%, or at least 60%.

In another embodiment, the pH of the culture medium used for the cultivation of the MDCK cells of the invention is regulated during culturing and is in the range from pH 6.4 to pH 8.0, or in the range from pH 6.8 to pH 7.4. In a specific embodiment, the pH of the culture medium is at least 6.4, or at least 6.6, or at least 6.8, or at least 7.0, or at least 7.2, or at least 7.4, or at least 7.6, or at least 7.8, or at least 8.0.

In a further embodiment, the MDCK cells of the invention are cultured at a temperature of 25° C. to 39° C. It is specifically contemplated that the culture temperature may be varied depending on the process desired. For example, the MDCK cells of the invention may be grown at 37° C. for proliferation of the cells and at a lower temperature (e.g., 25° C. to 35° C.) of for the production of vaccine material (e.g., virus). In another embodiment, the cells are cultured at a temperature of less than 30° C., or of less than 31° C., or of less than 32° C., or of less than 33° C., or of less than 34° C. for the production of vaccine material. In another embodiment, the cells are cultured at a temperature of 30° C., or 31° C., or 32° C., or 33° C., or 34° C. for the production of vaccine material.

In order to generate vaccine material (e.g., virus) it is specifically contemplated that the MDCK cells of the invention are cultured such that the medium can be readily exchanged (e.g., a perfusion system). The cells may be cultured to a very high cell density, for example to between $1 \times 10^6$ and $25 \times 10^6$ cells/mL. The content of glucose, glutamine, lactate, as well as the pH and $pO_2$ value in the medium and other parameters, such as agitation, known to the person skilled in the art can be readily manipulated during culture of the MDCK cells of the invention such that the cell density and/or virus production can be optimized.

Production of Vaccine Material (e.g., Virus)

The present invention provides a process for the production of viruses in cell culture (referred to hereinafter as "the process of the invention"), in which the MDCK cells of the invention are used. In one embodiment the process comprises the following steps:
 i) proliferation of the MDCK cells of the present invention in culture media;
 ii) infection of the cells with virus; and
 iii) after a further culturing phase, isolating the viruses replicated in the non-tumorigenic cells.

In one embodiment the MDCK cells of the invention are proliferated in step (i) as adherent cells. The MDCK cells of the invention can be cultured in the course of the process in any media including, but not limited to, those described supra. In certain embodiments, the MDCK cells of the invention are cultured in the course of the process in a serum-free medium such as, for example, MediV-SF101, MediV-SF102, MediV-SF103, MediV-SF104, MediV-SF105 and APF formulations thereof. Optionally, the MDCK cells of the invention can be cultured in the course of the process in a serum containing media (e.g., DMEM+10% FBS+4 mM glutamine+4.5 g/L glucose). Additional culture conditions such as, for example, temperature, pH, $pO_2$, $CO_2$ concentration, and cell density are described in detail supra. One skilled in the art can establish a combination of culture conditions for the proliferation of the MDCK cells of the invention for the production of virus.

The temperature for the proliferation of the cells before infection with viruses is in one embodiment between 22° C. and 40° C. In certain embodiments, the temperature for the proliferation of the cells before infection with viruses is less then 39° C., or less than 38° C., or less than 37° C., or less than 36° C., or less than 35° C., or less than 34° C., or less than 33° C., or less than 32° C., or less than 30° C., or less than 28° C., or less than 26° C., or less than 24° C. Culturing for proliferation of the cells (step (i)) is carried out in one embodiment of the process in a perfusion system, e.g. in a stirred vessel fermenter, using cell retention systems known to the person skilled in the art, such as, for example, centrifugation, filtration, spin filters, microcarriers, and the like.

The cells are in this case proliferated for 1 to 20 days, or for 3 to 11 days. Exchange of the medium is carried out in the course of this, increasing from 0 to approximately 1 to 5 fermenter volumes per day. The cells are proliferated up to high cell densities in this manner, for example up to at least $1 \times 10^6$-$25 \times 10^6$ cells/mL. The perfusion rates during culture in the perfusion system can be regulated via the cell count, the content of glucose, glutamine or lactate in the medium and via other parameters known to the person skilled in the art. Alternatively, the cells in step (i) of the process according to the invention be cultured in a batch process.

In one embodiment of the process according to the invention, the pH, $pO_2$ value, glucose concentration and other parameters of the culture medium used in step (i) is regulated during culturing as described above using methods known to the person skilled in the art.

In another embodiment, the infection of the cells with virus is carried out at an m.o.i. (multiplicity of infection) of about 0.0001 to about 10, or about 0.0005 to about 5, or about 0.002 to about 0.5. In still another embodiment, the infection of the cells with virus is carried out at an m.o.i. (multiplicity of infection) of 0.0001 to 10, or 0.0005 to 5, or 0.002 to 0.5. After infection, the infected cell culture is cultured further to replicate the viruses, in particular until a maximum cytopathic effect or a maximum amount of virus antigen can be detected. In one embodiment, after infection the cells are cultured at a temperature of between 22° C. and 40° C. In certain embodiments, after infection with viruses the cells are cultured at a temperature of less then 39° C., or less than 38° C., or less than 37° C., or less than 36° C., or less than 35° C., or less than 34° C., or less than 33° C., or less than 32° C., or less than 30° C., or less than 28° C., or less than 26° C., or less than 24° C. In another embodiment, after infection the cells are cultured at a temperature of less than 33° C. In still another embodiment, after infection the cells are cultured at a temperature of 31° C. In certain embodiments, the culturing of the cells is carried out for 2 to 10 days. The culturing can be carried out in the perfusion system or optionally in the batch process.

The culturing of the cells after infection with viruses (step (iii)) is in turn carried out such that the pH and $pO_2$ value are maintained as described above. During the culturing of the cells or virus replication according to step (iii) of the process, a substitution of the cell culture medium with freshly prepared medium, medium concentrate or with defined constituents such as amino acids, vitamins, lipid fractions, phosphates etc. for optimizing the antigen yield is also possible. The cells can either be slowly diluted by further addition of medium or medium concentrate over several days or can be incubated during further perfusion with medium or medium concentrate. The perfusion rates can in this case in turn be regulated by means of the cell count, the content of glucose, glutamine, lactate or lactate dehydrogenase in the medium or other parameters known to the person skilled in the art. A combination of the perfusion system with a fed-batch process is further possible.

In one embodiment of the process, the harvesting and isolation of the produced viruses (step (iii)) is carried out after a sufficient period to produce suitable yields of virus, such as 2 to 10 days, or optionally 3 to 7 days, after infection. In one embodiment of the process, the harvesting and isolation of the produced viruses (step (iii)) is carried out 2 days, or 3 days, or 4 days, or 5 days, or after 6 days, or 7 days, or 8 days, or 9 days, or 10 days, after infection.

Viruses which may be produced in the MDCK cells of the present invention include but are not limited to, animal viruses, including families of Orthomyxoviridae, Paramyxoviridae, Togaviridae, Herpesviridae, Rhabdoviridae, Retroviridae, Reoviridae, Flaviviridae, Adenoviridae, Picornaviridae, Arenaviridae and Poxyiridae.

Systems for producing influenza viruses in cell culture have also been developed in recent years (See, e.g., Furminger. in *Textbook of Influenza*, ed Nicholson, Webster and Hay, pp. 324-332, Blackwell Science (1998); Merten et al. in *Novel Strategies in The Design and Production of Vaccines*, ed Cohen & Shafferman, pp. 141-151, Kluwer Academic (1996)). Typically, these methods involve the infection of suitable immortalized host cells with a selected strain of virus. While eliminating many of the difficulties related to vaccine production in hen's eggs, not all pathogenic strains of influenza grow well and can be produced according to established tissue culture methods. In addition, many strains with desirable characteristics, e.g., attenuation, temperature sensitivity and cold adaptation, suitable for production of live attenuated vaccines, have not been successfully grown, especially at commercial scale, in tissue culture using established methods.

The present invention provides several non-tumorigenic MDCK cell lines, which have been adapted to grow in either serum containing or serum-free medias and which are capable of supporting the replication of viruses including but not limited to influenza when cultured. These cells lines are suitable for the economical replication of viruses in cell culture for use as vaccine material. The MDCK cells of the present invention are particularly useful for the production of cold adapted, temperature sensitive (ca/ts) strains of influenza (e.g., the influenza strains found in FluMist®) which do not grow well using other established cell lines (see, Example 1, infra). Further, the MDCK cells of the present invention are useful for the production of strains of influenza which may not grow in embryonated eggs such as avian influenza viruses which can also cause disease in humans (e.g., a "pandemic" strains)

Influenza viruses which may be produced by the process of the invention in the MDCK cells of the invention include but are not limited to, reassortant viruses that incorporate selected hemagglutinin and/or neuramimidase antigens in the context of an attenuated, temperature sensitive, cold adapted (ca/ts/at) master strain. For example, viruses can comprise the backbones (or one or more vRNA segment) of master strains that are one or more of, e.g., temperature-sensitive (ts), cold-adapted (ca), or an attenuated (att) (e.g., A/Ann Arbor/6/60, B/Ann Arbor/1/66, PR8, B/Leningrad/14/17/55, B/14/5/1, B/USSR/60/69, B/Leningrad/179/86, B/Leningrad/14/55, B/England/2608/76 etc.). Methods for the production of reassortant influenza vaccine strains in either eggs or cell lines are known in the art and include, for example, Kilbourne, E. D. in *Vaccines* ($2^{nd}$ Edition), ed. Plotkin and Mortimer, WB Saunders Co. (1988) and those disclosed in PCT Application PCT Patent Publication Nos. WO 05/062820 and WO 03/091401. Other influenza viruses which may be produced by the process of the invention in the MDCK cells of the invention include recombinant influenza viruses which may express a heterologous gene product, see for example, U.S. Patent Publication Nos. 2004/0241139 and 2004/0253273.

In one embodiment, the cells are proliferated (step (i)) as described supra, the cells are then infected with influenza viruses (step (ii)). In certain embodiments, the infection is carried out at an m.o.i. (multiplicity of infection) of 0.0001 to 10, or of 0.0005 to 5, or of 0.002 to 0.5. In other embodiments, the infection is carried out at an m.o.i. (multiplicity of infection) of about 0.0001 to about 10, or of about 0.0005 to about 5, or of about 0.002 to about 0.5. Optionally a protease is added which brings about the cleavage of the precursor protein of hemagglutinin [$HA_0$] and thus the adsorption of the viruses on the cells. The addition of a protease can be carried out according to the invention shortly before, simultaneously to or shortly after the infection of the cells with influenza viruses (step (ii)). If the addition is carried out simultaneously to the infection, the protease can either be added directly to the cell culture to be infected or, for example, as a concentrate together with the virus inoculate. The protease is, in certain aspects of the invention, a serine protease, or a cysteine protease, or an asparagine protease. In one embodiment, trypsin is used. In a specific embodiment, TPCK-treated trypsin is used.

In one embodiment, trypsin is added to the cell culture up to a final concentration of 1 to 5000 mU/ml, or 5 to 1000 mU/ml, or 100 to 500 mU/ml. In an alternative embodiment, trysin is added to the cell culture up to a final concentration of 1 to 200 μg/ml, or 5 to 50 μg/ml, or 5 to 30 μg/ml in the culture medium. During the further culturing of the infected cells according to step (iii) of the process according to the invention, trypsin reactivation can be carried out by fresh addition of trypsin in the case of the batch process or in the case of the perfusion system by continuous addition of a trypsin solution or by intermittent addition.

After infection, the infected cell culture is cultured further to replicate the viruses, in particular until a maximum cytopathic effect or a maximum amount of virus and/or virus antigen can be detected. In certain embodiments, the culturing of the cells is carried out for 2 to 10 days. The culturing can in turn be carried out in the perfusion system or optionally in the batch process. In a further embodiment, the cells are cultured at a temperature of 25° C. to 36° C., or of 29° C. to 34° C., after infection with influenza viruses. The culturing of the infected cells at temperatures below 33° C., in particular in the temperature ranges indicated above, leads to the production of higher yields of certain influenza viruses, such as, for example B strains. Furthermore, the culturing of the infected cells at temperatures below 35° C. is contemplated for the production of temperature sensitive, cold adapted (ts/ca) influenza virus. It is contemplated that ts/ca viruses may also be attenuated (att). In another embodiment, the cells are cultured at a temperature of less than 30° C., or of less than 31° C., or of less than 32° C., or of less than 33° C., or of less than 34° C. for the production of ts/ca influenza strains. In a specific embodiment, the cells are cultured at a temperature of 31° C., for the production of influenza virus B strains.

The culturing of the cells after infection with influenza viruses (step (iii)) is in turn carried out, for example, as described supra In one embodiment of the process, the harvesting and isolation of the produced influenza viruses (step (iii)) is carried out after a sufficient period to produce suitable yields of virus, such as 2 to 10 days, or 3 to 7 days, after infection. Viruses are typically recovered from the culture medium, in which infected cells have been grown. Typically crude medium is clarified prior to concentration of influenza viruses. Common methods include filtration, ultrafiltration, adsorption on barium sulfate and elution, and centrifugation. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus may be concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode. Additional details sufficient to guide one of skill through the preparation of influenza viruses from tissue culture are provided, e.g., in Furminger, in *Textbook of Influenza* pp. 324-332 Nicholson et al. (ed); Merten et al., in *Novel Strategies in Design and Production of Vaccines* pp. 141-151 Cohen & Shafferman (ed), and U.S. Pat. No. 5,690,937. If desired, the recovered viruses can be stored at −80° C. in the presence of a stabilizer, such as sucrose-phosphate-glutamate (SPG).

In certain embodiments of the process, the virus is treated with Benzonase® or other a non-specific endonuclease. Optionally, the Benzonase® treatment occurs early in the harvesting and isolation of the produced influenza viruses (step (iii)). In other embodiments of the process, following Benzonase® treatment, the material is clarified. Methods useful for clarification include but are not limited to, direct flow filtration (DFF). Additional steps which may be utilized for the harvesting and isolation of the produced influenza virus (step(iii)) include but are not limited to, tangential flow filtration (TFF), affinity chromatography as well as ion-exchange chromatography and/or hydroxyapatite chromatography. Other steps are exemplified in the Examples section infra.

Vaccine Compositions and Methods of Use

The invention further relates to viruses (e.g., influenza) which are obtainable by a process of the invention. These viruses can be formulated by known methods to provide a vaccine for administration to humans or animals. The viruses can be present as intact virus particles (e.g., live attenuated viruses) or as inactive/disintegrated virus (e.g., treated with detergents of formaldehyde). Optionally, a defined viral component (e.g., protein) may be isolated from the viruses by methods know to the person skilled in the art, and used in the preparation of a vaccine.

The formulation of intact virus particles (e.g., live attenuated viruses) may include additional steps including, but not limited to, a buffer exchange by filtration into a final formulation followed by a sterilization step. Buffers useful for such a formulation may contain 200 mM sucrose and a phosphate or histidine buffer of pH 7.0-7.2 with the addition of other amino acid excipients such as arginine. In certain embodiments, stabilization protein hydrolysates such as porcine gelatin are added. In some embodiments, the final viral solutions/vaccines of the invention can comprise live viruses that are stable in liquid form for a period of time sufficient to allow storage "in the field" (e.g., on sale and commercialization when refrigerated at 2-8° C., 4° C., 5° C., etc.) throughout an influenza vaccination season (e.g., typically from about September through March in the northern hemisphere). Thus, the virus/vaccine compositions are desired to retain their potency or to lose their potency at an acceptable rate over the storage period. In other embodiments, such solutions/vaccines are stable in liquid form at from about 2° C. to about 8° C., e.g., refrigerator temperature. For example, methods and compositions for formulating a refrigerator stable attenuated influenza vaccine are described in PCT Patent Application PCT/US2005/035614 filed Oct. 4, 2005, also see PCT Publication WO 05/014862. Optionally, spray drying, a rapid drying process whereby the formulation liquid feed is spray atomized into fine droplets under a stream of dry heated gas, may be utilized to extend storage time of a vaccine formulation. The evaporation of the fine droplets results in dry powders composed of the dissolved solutes (see, e.g., US Patent Publication 2004/0042972). Methods for the generation and formulation of inactive/disintegrated virus particles for vaccine compositions are well known in the art and have been utilized for over 40 years.

Generally, virus or viral components can be administered prophylactically in an appropriate carrier or excipient to stimulate an immune response specific for one or more strains of virus. Typically, the carrier or excipient is a pharmaceutically acceptable carrier or excipient, such as sterile water, aqueous saline solution, aqueous buffered saline solutions, aqueous dextrose solutions, aqueous glycerol solutions, ethanol or combinations thereof. The preparation of such solutions insuring sterility, pH, isotonicity, and stability is effected according to protocols established in the art. Generally, a carrier or excipient is selected to minimize allergic and other undesirable effects, and to suit the particular route of administration, e.g., subcutaneous, intramuscular, intranasal, etc.

Optionally, the formulation for prophylactic administration of the viruses, or components thereof, also contains one or more adjuvants for enhancing the immune response to the influenza antigens. Suitable adjuvants include: saponin, mineral gels such as aluminum hydroxide, surface active substances such as lysolecithin, pluronic polyols, polyanions, peptides, oil or hydrocarbon emulsions, bacille Calmette-Guerin (BCG), *Corynebacterium parvum*, and the synthetic adjuvants QS-21 and MF59.

Generally, vaccine formulations are administered in a quantity sufficient to stimulate an immune response specific for one or more strains of influenza virus. Preferably, administration of the viruses elicits a protective immune response. Dosages and methods for eliciting a protective immune response against one or more viral strain are known to those of skill in the art. For example, inactivated influenza viruses are provided in the range of about 1-1000 $HID_{50}$ (human infectious dose), i.e., about $10^5$-$10^8$ pfu (plaque forming units) per dose administered. Alternatively, about 10-50 μg, e.g., about 15 μg HA is administered without an adjuvant, with smaller doses being administered with an adjuvant. Typically, the dose will be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needleless injection device. Alternatively, the vaccine formulation is administered intranasally, either by drops, large particle aerosol (greater than about 10 microns), or spray into the upper respiratory tract. While any of the above routes of delivery results in a protective systemic immune response, intranasal administration confers the added benefit of eliciting mucosal immunity at the site of entry of the influenza virus. For intranasal administration, attenuated live virus vaccines are often preferred, e.g., an attenuated, cold adapted and/or temperature sensitive recombinant or reassortant influenza virus. While stimulation of a protective immune response with a single dose is preferred, additional dosages can be administered, by the same or different route, to achieve the desired prophylactic effect. These methods can be adapted for any virus including but not limited to, orthomyxoviruses (including influenza A and B strains), paramyxoviruses (including RSV, human metapneumovirus and parainfluenza), rhabdoviruses and flavoviruses.

Influenza Virus

The methods, processes and compositions herein primarily concerned with production of influenza viruses for vaccines. Influenza viruses are made up of an internal ribonucleoprotein core containing a segmented single-stranded RNA genome and an outer lipoprotein envelope lined by a matrix protein. Influenza A and influenza B viruses each contain eight segments of single stranded negative sense RNA. The influenza A genome encodes eleven polypeptides. Segments 1-3 encode three polypeptides, making up a RNA-dependent RNA polymerase. Segment 1 encodes the polymerase complex protein PB2. The remaining polymerase proteins PB1 and PA are encoded by segment 2 and segment 3, respectively. In addition, segment 1 of some influenza strains encodes a small protein, PB1-F2, produced from an alternative reading frame within the PB1 coding region. Segment 4 encodes the hemagglutinin (HA) surface glycoprotein involved in cell attachment and entry during infection. Segment 5 encodes the nucleocapsid nucleoprotein (NP) polypeptide, the major structural component associated with viral RNA. Segment 6 encodes a neuramimidase (NA) envelope glycoprotein. Segment 7 encodes two matrix proteins, designated M1 and M2, which are translated from differentially spliced mRNAs. Segment 8 encodes NS1 and NS2, two nonstructural proteins, which are translated from alternatively spliced mRNA variants.

The eight genome segments of influenza B encode 11 proteins. The three largest genes code for components of the RNA polymerase, PB1, PB2 and PA. Segment 4 encodes the HA protein. Segment 5 encodes NP. Segment 6 encodes the NA protein and the NB protein. Both proteins, NB and NA, are translated from overlapping reading frames of a biscistronic mRNA. Segment 7 of influenza B also encodes two proteins: M1 and M2. The smallest segment encodes two products, NS1 which is translated from the full length RNA, and NS2 which is translated from a spliced mRNA variant.

Reassortant viruses are produced to incorporate selected hemagglutinin and neuraminidase antigens in the context of an approved master strain also called a master donor virus (MDV). FluMist® makes use of approved cold adapted, attenuated, temperature sensitive MDV strains (e.g., A/AnnArbor/6/60 and B/Ann Arbor/1/66). A number of methods are useful for the generation of reassortant viruses including egg-based methods and more recently cell culture methods See, e.g., PCT Publications WO 03/091401; WO 05/062820 and U.S. Pat. Nos. 6,544,785; 6,649,372; 6,951,754). It is contemplated that the MDCK cells, media and processes of the invention are useful for the production of influenza viruses including, but not limited to, the influenza strains disclosed herein (e.g., A/AnnArbor/6/60 and B/AnnArbor/1/66) and reassortant viruses comprising genes of the A/AnnArbor/6/60, B/AnnArbor/1/66, PR8. It is further contemplated that that the MDCK cells, media and processes of the invention are useful for the production of influenza viruses, including reassortant viruses, having one or more of the following phenotypes, temperature sensitive, cold adapted, attenuated. Reassortants may be generated by classical reassortant techniques, for example by co-infection methods or optionally by plasmid rescue techniques (see, e.g., PCT Publications WO 03/091401; WO 05/062820 and U.S. Pat. Nos. 6,544,785; 6,649,372, 6,951,754).

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Example 1

Determination of Spread of Infection of ca/ts Influenza Strains in Cell Lines and Characterization of Influenza Produced in MDCK Cells There has been an effort by the vaccine industry to develop alternative production platforms that do not utilize eggs and to produce influenza vaccines in a mammalian or insect cell culture system. The obvious advantages are easy scalability, increased process control and removal of egg proteins that could cause allergic reaction in some vaccines. Since cell culture based systems can be rapidly scaled up, it offers an additional advantage at the time of a influenza pandemic, when there is a potential for shortage of supply of eggs and rapid production of vaccine is required. Initial studies have been performed with a total of 7 different cell lines: 2 human diploid lung fibroblast lines (MRC-5 and WI-38) (data not shown), a human retinoblastoma and a human kidney cell line both of which were genetically constructed for production of adenoviral products (PER.C6 and 293, respectively) (data not shown), a fetal rhesus lung cell line (FRhL2) (data not shown), an African green monkey kidney cell line (Vero), and a Marin-Darby canine kidney cell line (MDCK). MDCK cells were the only cell line of those tested to be capable of propagating all four types of cold adapted, temperature sensitive attenuated (ca/ts/att) reassortant influenza virus strains, H1N1, H3N2, the potential pandemic vaccine strain H5N1, as well as B strains, to commercially reasonable titers (>$10^7$ Log $TCID_{50}$/mL) (FIG. 1 and data not shown). The genetic and antigenic characteristics of virus grown in MDCK cells was compared to that of virus grown in eggs. No significant changes in the genomic sequence were seen (data not shown) and the antigenicity as determined by HAI titers were comparable (Table 1).

Fluorescent Focus Assay: MDCK and Vero cells were grown in 96 well black plates over 4 days (DMEM+4 mM glutamine+PEN/Strep). Each well was infected with the ca/ts influenza B-strains (B/HongKong/330/01 and B/Yamanashi/166/98) at an MOI of ~0.01 in DMEM+4 mM glutamine+60 mU/mL TPCK trypsin. The virus infected plates were fixed and immuno-stained as follows to determine the spread of infection. The medium containing virus was removed from each plate and the plates washed once with 200 µl/well with DPBS (no Ca2+/Mg2+) and the plates were then fixed by addition of 200 µl/well of cold 4% (v/v) paraformaldehyde in PBS. The plates were washed twice with 200 µl/well of DPBS (no $Ca^{2+}/Mg^{2+}$) followed by incubation of the cells with primary antibody (sheep anti B yamanshi and sheep anti B hongkong diluted in 0.1% saponin, 1% BSA in PBS at a ratio of 1:1000). After incubation for an hour, the primary antibody was removed and cells were washed thrice with 0.1% Tween 20 in PBS and the wells were incubated with secondary antibody (rabbit anti sheep labeled with FITC in 0.1% saponin, 1% BSA in PBS at 1:100 ratio dilution). The wells were visualized daily for 4 days using a fluorescence microscope and the images were taken daily using SPOT program.

Results And Discussion

A fluorescent focus assay was use to assess whether there was spread of infection of ca/ts influenza B-strains in MDCK and Vero and also assess if there was any difference in the spread of virus infection among the 50 cell clones of Vero. Since the fluorescence in the monolayer increased over 4 days in the MDCK cells but not in the Vero cells (see, FIG. 1A), it was concluded that the Vero were not permissive for the production of ca/ts B strains while MDCK were. This data was similar to the data in earlier experiments that showed that B-strains could be produced to 7-7.5 $\log_{10}$ $TCID_{50}$ in MDCK cells but only to 4-4.5 $\log_{10}$ $TCID_{50}$ in Vero Cells (data not shown).

The MDCK cells were also tested for their ability to support replication of a number of ca/ts/att reassortant strains including a potential pandemic vaccine strain, ca A/Vietnam/1203/2004. MDCK cells were infected at a low multiplicity of infection with ca A/Vietnam/1203/2004 and virus in the supernatant was quantified at various times post infection. By 48 hours post infection, the titers of ca A/Vietnam/1203/2004 reached approximately 8 $\log_{10}$ $TCID_{50}$/mL and remained stable for the next 3 to 4 days. See FIG. 1B and Table 2.

Ca/ts/att strains of type A/H1N1, A/H5N1, A/H3N2 and B replicated to relatively high titers in MDCK cells. In addition, passaging these ca/ts/att strains in MDCK cells did not significantly alter their genomic sequence. Three ca/ts/att strains, ca A/Sydney/05/97, ca A/Beijing/262/95, and ca B/Ann Arbor/1/94 were passaged once or twice in MDCK cells and the entire coding regions of all 6 internal genes were sequenced and compared to the starting material. No nucleotide changes were observed (data not shown), demonstrating that this passaging through this substrate did not change the genetic composition of these strains. Further sequence characterizations is performed on different vaccine strains produced in MDCK cells under conditions that are expected to mimic the production process including media composition, input dose (moi), temperature of incubation and time of harvest. Based on the preliminary data, it is expected that there will be no significant changes in the genomic sequence of MDCK-produced virus.

Because the genome was genetically stable following passage in MDCK cell, the biological traits of the vaccine produced in eggs or MDCK cells are expected to be indistinguishable. However, the primary viral product from cell culture may have some subtle differences compared to the egg based product, particularly with respect to post-translational modification of viral proteins including HA and NA, or composition of lipids in the viral membrane; both of which could potentially change the overall physical properties of the virion. Preliminary preclinical data on the antigenicity of cell culture produced and egg produced vaccine demonstrated that there were no detectable differences in this important parameter. Egg stocks of several vaccine strains were passaged through MDCK cells and the antigenicity of both products was determined by measuring the HAI titers using reference antisera. As show in Table 1, all the HAI titers were within 2-fold of one another, indicating that replication of the vaccine in cells did not change the antigenicity of the vaccine compared to egg derived material.

TABLE 1

HAI Titers of strains produced in eggs and MDCK cells

| Strain | HAI Titer Egg derived | HAI Titer MDCK derived |
|---|---|---|
| A/Panama/20/99 | 256 | 256 |
| A/Wuhan/359/95 | 1024 | 2048 |
| A/Wyoming/03/2003 | 512 | 1024 |
| B/Jilin/20/2003 | 64 | 32 |
| B/Hong Kong/330/01 | 64 | 64 |
| B/Jiangsu/10/2003 | 128 | 128 |

Example 2

Derivation of Non-Tumorigenic Serum MDCK Cells

MDCK cells have been traditionally used for the titration of influenza viruses (Zambon, 1988, in Textbook of Influenza, ed Nicholson, Webster and Hay, ch 24, pg 324-332, Blackwell Science) and thus could be used for the propagation of influenza for the production of vaccine materials. However, MDCK cells have traditionally been grown in basal medium formulations like Eagle's Minimal Essential Medium (EMEM) supplemented with FBS. Multiple reports indicate that MDCK cells may be tumorigenic when cultivated under these conditions and/or for extended periods of time (see for example, Gaush et al., *Proc Soc Exp Biol Med,* 122:931; Leighton et al., 1968, *Science,* 163:472 and Leighton et al., 1970, *Cancer,* 26:1022). Thus, there is concern about the use of MDCK cells for the production of vaccine materials and efforts have focused on the development of other cell lines (e.g., PER.C6 and VERO). Unfortunately, not all influenza strains grow well in other mammalian cell lines, in particular the cold adapted influenza viruses that comprise FluMist®, a live attenuated influenza vaccine, only grow to reasonable titers (>$10^7$ TCID 50/mL) in MDCK cells (see Example 1, supra). Early reports characterizing MDCK cells indicate that early passages of MDCK cells may not be tumorigenic (Gaush et al., 1966, *Proc Soc Exp Biol Med.* 122: 931). It was the goal of this experiment to establish a culture media and passage protocol to maintain MDCK cells in a non-tumorigenic state.

MDCK cells obtained from the ATCC(CCL 34) were expanded in T-flasks using DMEM supplemented with 10% FBS, 4 mM glutamine and 4.5 g/L glucose as the growth medium. A pre-Master MDCK cell bank was established on the serum grown MDCK cells (MDCK-S cells), which was tested for bacterial/fungal contaminants and mycoplasma contamination using routine tests performed by a commercial contractor (BioReliance, Rockville, Md.). The cells were found to be negative for the presence of bacterial/fungal contaminants. The MDCK-S cells were also found to be negative for the presence of cultivatable mycoplasma. The MDCK-S cells from the bank were also tested by a karyotype assay and found to be canine in origin and had a modal chromosome number of 78 with chromosome numbers ranging from 70 to 84. The MDCK-S cells were then passaged for another 20 passages from a vial of PreMCB and tested for karyology and tumorigenicity in an vivo adult nude mice model. The karyology test showed that late passage MDCK-S cells (p 81/24) showed the same modal chromosome number (78) and range of chromosomes (70 to 84) as the early passage MDCK-S cells, showing that the cells did not change on extended passaging. 1×$10^7$ MDCK-S cells when injected subcutaneously into adult nude mice did not result in the formation of any nodules and were deemed to be non tumorigenic.

Materials and Methods

Materials: MDCK cell (ATCC, Cat. No: CCL-34); T-25, T-75, T-225 flasks (Corning, Cat No.: 430639, 430641, 431082); Dulbecco's Modified Eagle's Medium (DMEM) powder (Gibco, Grand Island N.Y., Formulation No.: 01-5052EF); Fetal Bovine Serum, Gamma-irradiated (JRH, Lenexa Kans., Cat. No.: 12107-500M); L-Glutamine (JRH, Lenexa Kans., Cat. No.: 59202-100M); D-Glucose (Amresco, Cat. No.: 0188-1KG); Dulbecco's Phosphate buffered saline (DPBS) without $Ca^{2+}$ and $Mg^{2+}$ powder (Gibco, Grand Island N.Y., Cat. No.: 21600-069); 0.05% Trypsin-EDTA (Gibco, Grand Island N.Y., Cat. No.: 25300) Dimethylsulphoxide, DMSO (Sigma, St. Louis Miss., Cat. No.: D2650); 0.4% w/v Trypan blue dye in PBS (Sigma, St. Louis Miss., Cat. No.: T8154); $CO_2$ Incubator (Form a Scientific, Model No.: 3110); YSI Bioanalyzer (YSI, Model No.: 2700 select); Vitro Chemistry System (Ortho clinic, Model: DT60 II); Improved Neubaurr hemacytometer (Hausser Scientific, Brightline 0.1 mm deep/Reichert, Brightline 0.1 mm deep).

Subculturing of Serum MDCK (MDCK-S) cells in Tissue Culture Flasks: A vial of serum MDCK cells was obtained from the ATCC. The cells were grown in DMEM medium supplemented with 10% (v/v) FBS, 4.5 g/L glucose, 2.2 g/L $NaHCO_3$ and 4 mM L-glutamine in T-75 flasks. The cells were passaged 3 or 4 days postseeding, with a complete medium exchange performed on day 3 after seeding if the cells were passaged on day 4. The cells were recovered from T-flasks as described below.

The spent growth medium was removed and the cell monolayer washed twice with DPBS (calcium and magnesium free). The appropriate amount of trypsin-EDTA (3 mL/T-75, 7.5 mL/T-225), prewarmed in a 37° C. water batch, was added to each flask and the T-flasks incubated in a 37° C., 5% $CO_2$ incubator for about 15-20 min. The flasks were checked every 5 minutes to check if cells had detached and the flasks were rapped several times to help detach the cells. When the cells had completed detached from the T-flask, the trypsin was inhibited by addition of equal volumes of complete growth medium containing 10% serum (3 mL/T-75, 7.5 mL/T-225). The cell suspension was aspirated up and down with an appropriately sized pipette to break any large cell clumps. Two 0.5 mL samples of cell suspension were counted in a hemacytometer. The cell counts were repeated if the results of the two counts were not within 15% of each other. The cells were diluted to $0.05 \times 10^6$ viable cells/mL in fresh warm growth medium (DMEM+10% FBS+4.5 g/L glucose+4 mM glutamine) in fresh flasks and seeded in T-flasks (35 mL/T75 or 100 mL/T-225). The flasks were then incubated in a $37 \pm 1°$ C., 5% $CO_2$ environment for 3 days prior to subculturing or media exchange.

Preparation of MDCK-S cell bank: MDCK-S cells were expanded in T-flasks as described above until the total required amount of cells needed for banking could be recovered ($4 \times 10^6$ cells/vial×number of vials). The MDCK-S cells were recovered when in the exponential growth phase (3 days post seeding) by trypsinization as described. The MDCK-S cell suspensions from individual flasks were pooled and cells were recovered by centrifugation at 150-250 g for $7 \pm 1$ min. The supernatant was aspirated off from each tube and the cell pellets were resuspended in fresh complete growth medium (DMEM+10% FBS+4.5 g/L glucose+4 mM glutamine). The cell suspensions from different centrifuge bottles were pooled and cell suspension was aspirated up and down with a pipette several times to break any large cells clumps. The total cell number was determined and the total number of vials that could be frozen at $4 \times 10^6$ cells/vial was determined.

The volume of cell suspension was then adjusted to the above value using fresh growth medium. Equal volumes of freshly prepared 2× freezing medium (DMEM+10% FBS+4 mM glutamine+4.5/L glucose+15% DMSO) was added to the cell suspension. Cell suspension was mixed thoroughly and 1 mL of cell suspension was dispensed into each cryovial. All the vials were transferred into Nalgene freezing containers and were placed in a $\leq -60°$ C. freezer. The frozen vials were transferred to a liquid nitrogen storage tank.

Preparation of MDCK-S cells Growth Curve in T-75 flasks: Cells were passaged at least 4 times (post thaw) in their growth medium prior to cell growth curve study. MDCK-S cells were expanded into T-225 flasks in order to obtain at least $2.7 \times 10^7$ total cells. The flasks were grown to 80-95% confluent prior to trypsinization as described above. The recovered MDCK-S cells were pooled and cell suspension aspirated up and down with a pipette several times to break any large cell clumps. Two samples (0.5 mL) were removed for cell counts and cell density determined. The two sample counts were repeated if they were not within 15% of each other. $2.7 \times 10^7$ total MDCK-S cells were then diluted to a total volume of 540 mL of complete growth medium ($5.0 \times 10^4$ cells/mL). This MDCK-S cell suspension was then dispensed into 14×T-75 flasks (35 mL/T-75 flask). The flasks were placed in a $37 \pm 1°$ C., 5% $CO_2$ incubator.

Two T-flasks were removed daily from incubator for cell counts and metabolic analysis. Two samples (approximately 1.0 mL) of cell culture media were removed from each flask for metabolic analysis. One sample was used to determine glucose, lactate, glutamine, glutamate and ammonia concentrations using the YSI and Vitros analyzers. The other sample was frozen at $-70°$ C. for amino acid analysis at a later date. The MDCK-S cells were recovered from each flask by trypsinization as described above. The cell density was determined and the total number of cells/T-flask was also determined. The two counts were repeated if they were not within 15% of each other. The numbers presented are the average of two independent growth curves studies performed at two different passage numbers (p63 and p65) of MDCK-S cells.

Karyology Test: The karyology test was carried out at Applied Genetics Laboratories in Melbourne, Fla. Briefly, MDCK-S cells grown in T-225 flasks were shipped to Applied Genetics Laboratories. The cells were maintained and sub-cultured as per the methods listed above. When the cells were thought to have enough mitotic cells, the cells were harvested for mitotic analysis. The cells were treated with colcemid (0.02 µg/mL) for 150 minutes at 37° C. The cells were then harvested by trypsinization, and cells centrifuged for 5 minutes at 200 g. The supernatant was aspirated off and the cells resuspended in prewarmed hypotonic solution and incubated at 37° C. for 10 minutes. The swollen cells were pelleted by centrifugation and then fixed by incubation in carnoy's solution (3:1 methanol:glacial acetic acid) at room temperature for 40 minutes. The cells were again centrifuged and cells washed at least twice with Carnoy's fixative. After the last centrifugation, the cells were resuspended in 1 to 3 ml of fresh fixative to produce an opalescent cell suspension. Drops of the final cell suspension were placed on clean slides and air dried.

Cells were stained by addition of Wright's stain solution in phosphate buffer to the slides and incubating for 7-10 minutes. The slides were washed with tap water after 7-10 minutes and then air dried. The cells were scanned with low power objectives (10×) to find cells in the metaphase stage of cell division and the chromosomes of cells in metaphase were analyzed via a high power oil immersion lens (100×). A 100 cells in metaphase were analyzed for cytogenic abnormalities and chromosome count. 1000 cells were scanned to determine polyploid frequency and mitotic index (percent of cells under going mitosis).

Sterility Testing of the MDCK-S PRE-MCB (Bacteriostatic and Fungastatic and Four Media Sterility): The MDCK-S Pre-MCB was tested for bacteriostatic and funstatic activity at Bioreliance Inc., Rockville, Md. The assay was performed to meet US 26 and 21 CFR 610.12 requirements. This assays tests whether the there is a difference in growth of control organisms (*Bacillus subtilis, Candida albicans, Clostridium sporogenes, Staphylococcus aureus, Pseudomonas aeruginonsa, Aspergillus Niger*) inoculated in appropriate broth medium containing 0.1 mL of test sample versus broth medium containing control organisms only. Briefly, the test article was inoculated into three tubes of TSB (soybean-casein digest medium), four tubes of THIO (fluid thioglycollate medium), two tubes of SAB (Sabourand Dextrose Agar) and one tube of PYG (peptone yeast extract). Each control organism containing less that 100 cfu of control organism was then inoculated into the appropriate media type. Positive controls consisted of *Bacillus subtilis* in TSB and THIO, *Candida albicans* in TSB and SAB (at 20-25° C. and 30-35° C.), *Clostridium* sporogenes in THIO and PYG, *Pseudomonas aeruginosa, Staphyloccus* aureus and *Aspergillus niger*. The negative control was sterile PBS. The media were incubated for 3-5 days and checked for growth of organisms.

The test article was also analyzed for presence of bacterial and fungal contaminants using the four media sterility test at Bioreliance, Rockville Md. and the assay was designed to meet USP 26, EP and 21CFR610.12 requirements. Briefly, the test article was inoculated in two tubes of two tubes of TSB (soybean-casein digest medium), two tubes of THIO (fluid thioglycollate medium), three tubes of SAB (Sabourand Dextrose Agar) and two tubes of PYG (peptone yeast extract). The media were incubated at appropriate temperatures (SAB slants were incubated at two temperatures) and all tubes observed over a 14 day period with the tubes checked on third/fourth or fifth day, seventh or eight day and fourteenth day of testing. Any test article inoculated tubes which appeared turbid were plated out and gram stains performed on the plate. Negative controls were sterile PBS.

Mycoplasma/mycoplasmstasis test: A vial of frozen MDCK-S cells (MDCK preMCB lot no. 747p105) was sent to Bioreliance. The cells were expanded and cultured in T-flasks as explained above. Cell lysates at a concentration of 5×10$^5$ cells/mL were prepared and frozen at −70° C. The test article was tested for ability to inhibit growth of *Mycoplasmapneumoniae, Mycoplasma orale* and *Mycoplasma hyorhinis* either in agar broth/plates and/or in VERO cells.

For the agar isolation assay, the test article was test either spiked or unspiked on agar plates or broth bottles. The test article was spiked with *Mycoplasmapneumoniae* and *Mycoplasma orale* to achieve a dilution of 10 to 100 cfu/0.2 mL (for Agar test) and 10 to 100 cfu/10 mL (for semi broth assay). A portion of the test sample was not spiked. 4 semi solid broth bottles were inoculated with 10 ml each of spiked (2 bottles) or unspiked (2 bottles). One bottle each of spiked/upspiked were incubated either aerobically or anaerobically at appropriate temperatures. 10 type A agar plates and 10 type B agar plates were inoculated with each spiked sample or unspiked sample. Half the type A agar plates and type B agar plates were incubated either aerobically or anaerobically at appropriate temperatures. Uninoculated mycoplasma semi-solid broth served as the uninoculated negative control. All broth bottles were observed for 21 days. Each broth bottle (with exception of uninoculated negative control) was subcultured on days 3, 7 and 14 onto Type A agar plates or Type B agar plates (10 plates each, 0.2 mL/plate) and incubated under the same conditions as the appropriate bottle. They were examined once a day for 21 days.

For the enhanced VERO cell culture assay, the test article was tested spiked or unspiked. The test article was spiked with *M. orale* and *M. hyorhinis* at a concentration of 10-100 cfu/0.2 mL. The spiked test articles, unspiked test articles, positive controls and negative controls were each inoculated onto T-75 flasks of VERO cell cultures. After 3-5 days of incubation, the cells from each flask were scraped and snap frozen. Two tenths of one mL of cell lysate from each flask, was inoculated into each of well of a six well plate containing VERO cells. In addition positive and negative controls were inoculated into appropriate wells of six well plates containing VERO cells. After 3-5 days the cells were fixed and stained with DNA binding HOECHT dye and evaluated for presence of mycoplasma.

Tumorizenicity test of MDCK-S cells in Nude Mice: Evaluation of tumor formation in nude (nu/nu) athymic mice was performed by BioReliance®, Rockville, Md. Briefly, thirty female athymic mice (4 weeks old) were injected subcutaneously with 0.2 mL (1×10$^7$ cells/mice) of either positive control (18Cl-10T cells), negative control (Syrian hamster embryo cells; SHE cells) or the test cells (Serum MDCK cells, 747p105 high passage). The animals were randomized before injection and all mice were injected using a 22 gauge needle on the same day. All animals were observed every working day and the injection site was palpated twice a week for lesion development for a period of eighty four days. Each lesion was measured and the animals were held as long as there was no visible increase in size of the lesion. This was for a maximum of 3 months. All mice were sacrificed and necropsied after 84 days and the injection site, lungs, scapular lymph nodes and gross lesions analyzed by histopathological methods.

Replication of cold adapted influenza strains in MDCK-S: T-75 flasks were seeded at 5×10$^4$ cells/mL (35 mL of DMEM+10% FBS+4 mM glutamine) and grown in an incubator maintained at 37° C. and 5% CO$_2$ for 3 days. 3 days post seeding, the total cells per T-flask were determined by harvesting using trypsin EDTA and cell counts determined by Trypan-Blue Exclusion. The remaining T-flasks were then infected as follows. The growth media was aspirated off and cells washed twice with 10 mL DPBS (no Ca$^{2+}$/Mg$^{2+}$) per flask. The amount of virus to infect each T-flask at a multiplicity of infection (MOI) of 0.01 was determined as per the equation below:

$$\text{Amount of virus(mL)} = \frac{\text{Total Cells per flask} * MOI}{10^{\wedge}(\log TCID50/\text{mL})}$$

MOI being defined as the virus particles per cell added

The required amount of virus is then added to 35 mL of post infection medium in each T-flask. (DMEM+4 mM glutamine+60 mu/mL TPCK trypsin). The T-flasks were then incubated at 33° C., 5% CO$_2$ and samples taken each day for 6 days. 10×SP was added to each sample as a stabilizer and the samples were stored at <−70° C. prior to testing for infectivity.

The concentration of virus present in each sample was determined according to a median tissue culture infectious dose (TCID$_{50}$) assay that measures infectious virions. Briefly, MDCK cells were grown to confluent monolayers in 96-well microtiter plates and a serial dilutions of calts influenza virus sample was added. The samples in the MDCK cell assay plate were typically at a final dilution of $10^{-4}$ to $10^{-10}$. The wells in columns 1-5 and 8-12 contained virus-diluted sample and wells in columns 6-7 received only virus diluent and served as cell controls. This format produced two data points (n=2) per plate. Replication of virus in the MDCK cells resulted in cell death and the release of progeny virus into the culture supernatant. The progeny virus infected other cells, resulting in the eventual destruction of the monolayer. The cytopathic effect (CPE) resulting from infection was allowed to develop during an incubation at 33±1° C. in a $CO_2$ environment for a period of six days. The plates were then removed from the incubator, the media in the wells discarded, and 100 µl of MEM+4 mM glutamine+penicillin/streptomycin+MTT was added to each well. The plates were incubated for 6 hrs at 37° C. 5% $CO_2$ and the number of wells showing CPE was determined by visual inspection of the color formed in each well (yellow/orange signifies CPE wells and solid purple signifying no CPE). The number of wells showing CPE in each half plate was used to calculate the titer ($\log_{10} TCID_{50}/mL$) based on the Karber modification of the Reed-Muench method.

Results and Discussion

Figure 2:
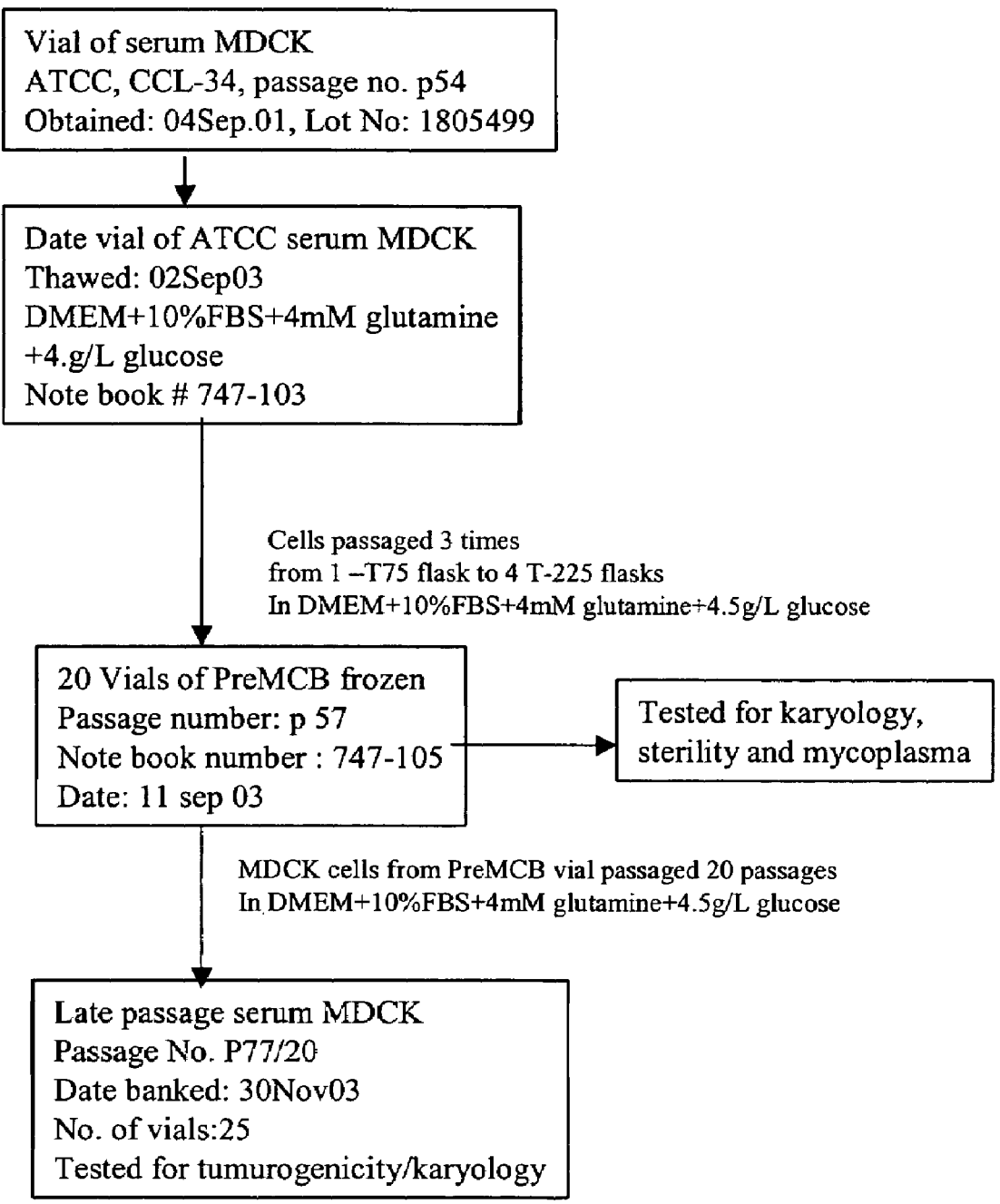
FIG. 2 outlines the process used for the derivation of MDCK-S PreMCB (passage No. 57). The process is described in detail in Example 2.
Figure 3:
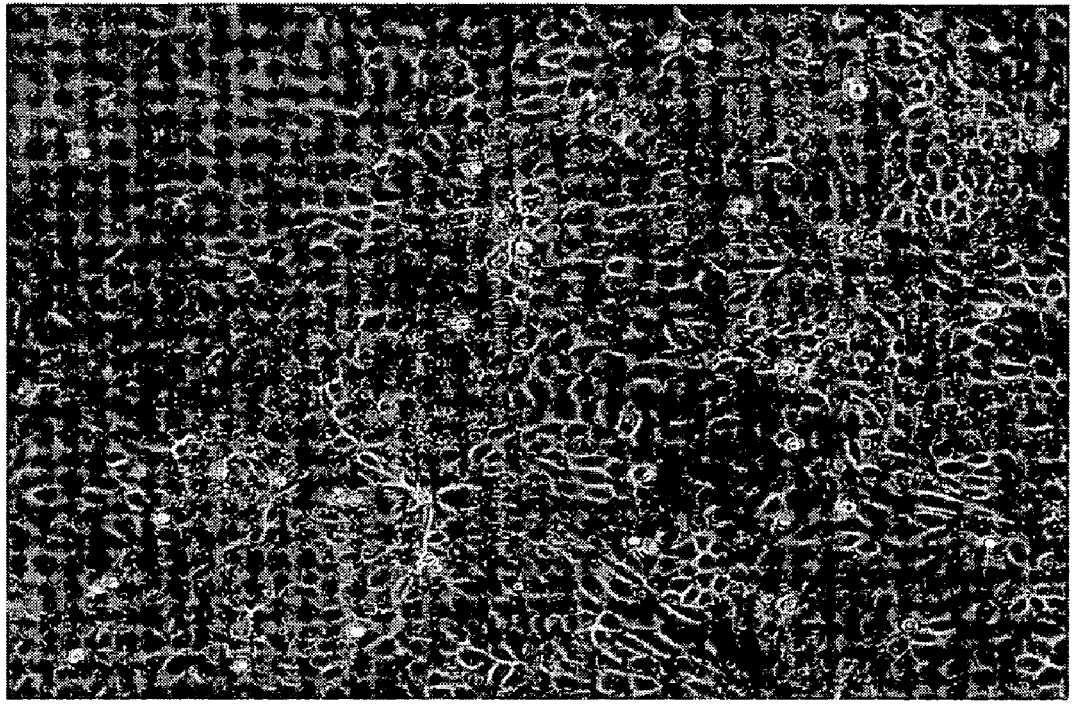
FIG. 3 is a photograph showing that MDCK-S cells have an epithelial-like morphology. The photo was taken 3 days after seeding.

Two frozen vials of serum MDCK cells were thawed in complete growth medium (DMEM+10% FBS+4 mM glutamine+4.5 g/L glucose) on separate occasions into T-75 flasks. The cell viability on thaw was 97% and 98% respectively. Cells achieved confluence three days after thawing. The morphology of cells were epithelial-like and similar to the stock obtained from ATCC (FIG. 3). These cells were passaged 5 times and a Pre-master cell bank PreMCB was established for these serum grown MDCK cells (MDCK-S cells). FIG. 2 outlines the process used for the derivation of the MDCK-S pre-master cell bank (pre-MCB).

Figure 4:
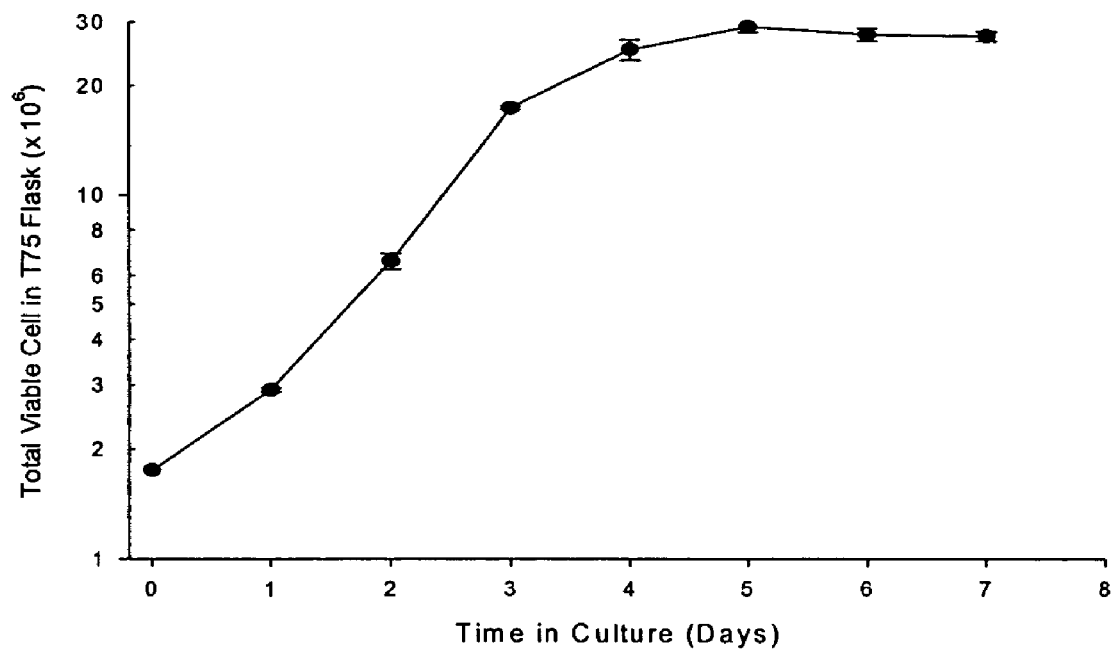
FIG. 4 is the growth curve of MDCK-S cells in 10% FBS DMEM medium. Cells had about a 1 day lag phase followed by exponential growth entering stationary phase at day 4 post seeding achieving a maximum density of ~29×10$^6$ cells on day 5.
Figure 5:
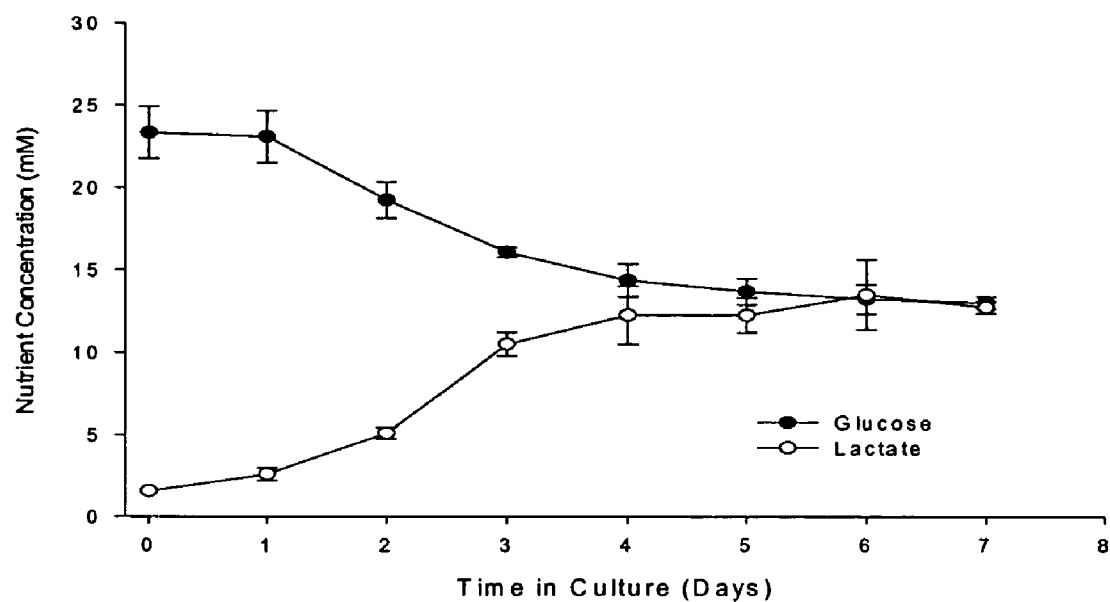
FIG. 5 is a graph of the glucose consumption and lactate production of MDCK-S cells in 10% FBS DMEM medium. The rates were low during lag phase increasing to 2.93 mM/day and 3.43 mM/day for glucose and lactate, respectively.

The growth curves for MDCK-S cells in 10% FBS DMEM medium are showed in FIG. 4. The results are the average of two experiments using cells at different passage numbers (P63&P65). MDCK-S cells had an approximately 1 day lag phase where the cell number did not double from seeding ($1.75 \times 10^6$ total cell/T75 flask at seeding and $2.9 \times 10^6$ total/T-75 day 1). The glucose consumption/lactate production rate was almost zero for the first day showing that the cells were in the lag phase (FIG. 5). Then cells grew exponentially during cell growth period before entering stationary phase at day 4 post seeding. The doubling time of MCDK-S cells in exponential growth phase was 23.1 hours. During the exponential phase the glucose consumption and lactate production mirrored each other with lactate increasing in concentration as the glucose concentration decreased (FIG. 5). The glucose consumption/lactate production rate correlated well with the cell growth curve (compare FIGS. 4 and 5). The rates were low during lag phase, increased to 2.93 mM/day for glucose, 3.43 mM/day for lactate during the exponential phase from day 1 to day 4.

The MDCK-S cells entered into the stationary phase day 4 post seeding, and achieved a maximum cell density was around $29\pm0.99\times10^6$ cell on day 5 post seeding (FIG. 4). The cell number remained constant after reaching maximum density and up to day 7 in this study. The glucose consumption and lactate production rate slowed to 0.33 mM/day for glucose and 0.25 mM/day for lactate in stationary phase. There was still approximately 12 mM glucose remaining in the medium after 7 days culture. The ratio of amount of glucose consumed to lactate produced at day 4 was 1.2.

Figure 6:
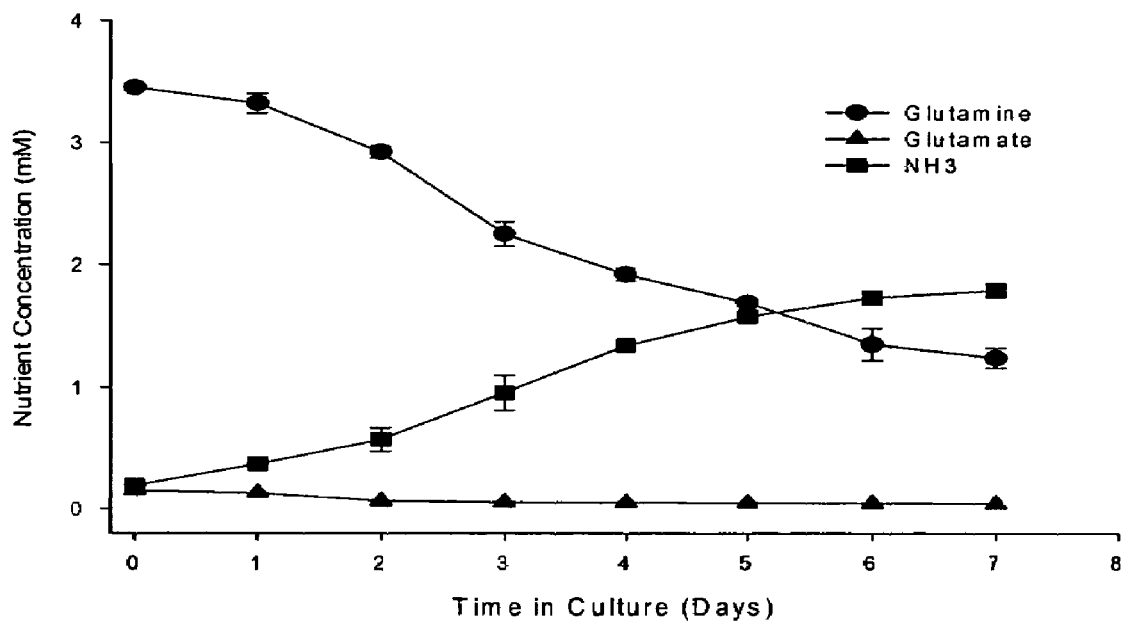
FIG. 6 is a graph of the glutamine consumption and both glutamate and ammonia production of MDCK-S cells in 10% FBS DMEM medium. The glutamine consumption rate was 0.49 mM/day up to day 4 and the ammonia production rate was 0.32 mM/day up to day 5. Glutamate did not accumulate in this study.

Glutamine consumption and both glutamate and ammonia production of the MDCK-S cells are shown in FIG. 6. The rate of glutamine consumption and production of ammonia correlated with the cell growth curve as well (compare FIGS. 4 and 6). The MDCK-S cells consumed glutamine at a rate of 0.49 mM/day during the exponential growth phase up to day 4 while producing ammonia at a rate of 0.32 mM/day up to day 5. Then the rate of glutamine consumption dropped to 0.24 mM/day while the ammonia production rate dropped to 0.11 mM/day, when the cells entered the stationary phase. The ratio of ammonia production to glutamine consumption was 0.7 on day 4 post seeding. Glutamate generated from glutamine metabolism did not accumulate in this 7 days cell growth study.

Figure 7:
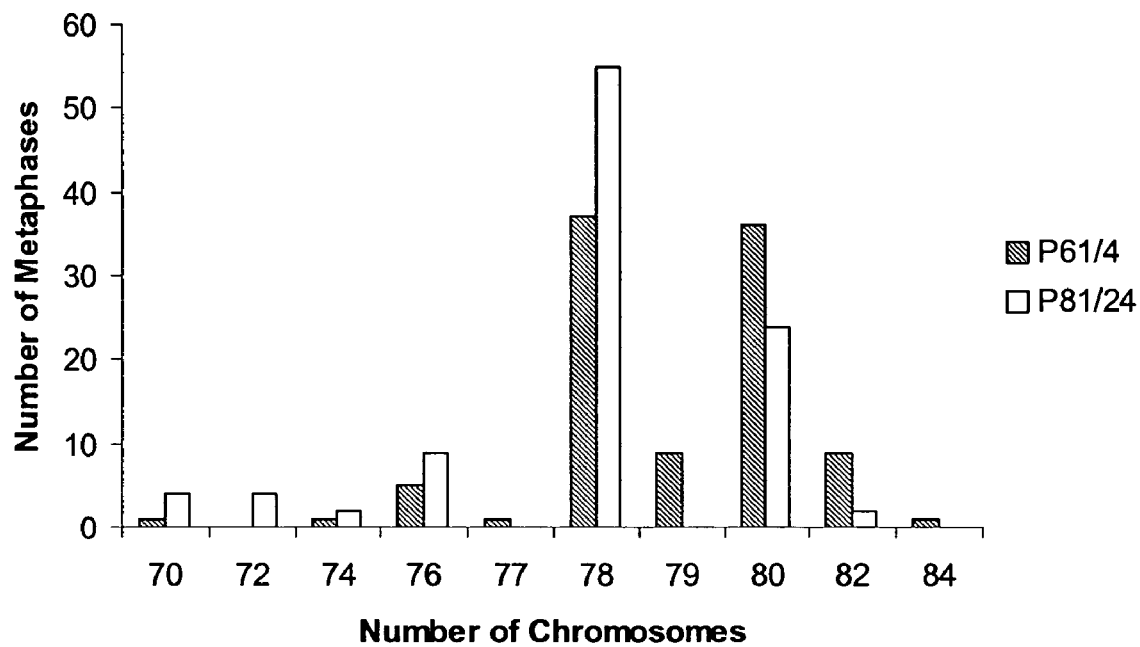
FIG. 7 is a plot of the distributions of chromosome number in 100 metaphase low passage (P61/4) and high passage (P81/24) MDCK-S cells. The chromosome count ranged from 70 to 84 per metaphase with a modal chromosome number of 78 for both the high and low passage cells.

The karyology of the MDCK-S cells was tested at passage 61/4 and passage 81/24. The G-band chromosome analysis showed that the cells were canine in origin. The distributions of chromosome number in 100 metaphases cells are shown in FIG. 7. The chromosome count ranged from 70 to 84 chromosomes per metaphase for cells at low passage 61/4 and 70 to 84 chromosomes for high passage 81/24. Both passages had a modal chromosome number of 78 chromosomes. The distribution of chromosomes did not change with passaging. The modality of cells were as expected for a normal canine kidney cell (Starke et al., 1972, *Prog Immunobiol Stand.*, 5:178).

The MDCK-S preMCB was tested for presence any bacterial, fungal or mycoplasma contaminants. The pre-MCB was passed sterility test (four media sterility test using direct inoculation method to check bacterial and fungal contaminants) and was found to be negative for presence of mycoplasma (agar-cultivable and non-agar cultivable assay). The test article was also found not to inhibit the growth of positive controls in both the bacteriostasis/fungistatis test and mycoplasmstatis test.

MDCK-S cells at passage 81/24 (pre-MCB+20 passages) were put on nude mice for tumorigenicity test for 3 months. No neoplasma were diagnosed in any mice that were inoculated with MDCK-S cells demonstrating that MDCK-S cells were not tumorigenic (Table 4).

The MDCK-S cells were tested and found to be capable of supporting the replication of cold adapted temperature sensitive attenuated reassortant influenza strains (Table 2).

TABLE 2

Growth of cold adapted influenza virus strains in serum and serum-free MediV SF101 adapted MDCK cells

| Virus Strain (6:2 reassortant) | Serum MDCK ($\log_{10} TCID_{50}/mL$) | Serum-free MDCK ($\log_{10} TCID_{50}/mL$) |
|---|---|---|
| A/New Caledonia/20/99 | 8.1 | 7.8 |
| A/Texas/36/91 | 6.4 | <5.2 |
| A/Panama/2007/99 | 6.8 | 6.4 |
| A/Sydney/05/97 | 7.0 | 6.5 |
| B/Brisbane/32/2002 | 7.2 | 7.5 |
| B/HongKong/330/01 | 7.2 | 7.4 |
| B/Victoria/504/2000 | 6.9 | 7.5 |

Example 3

Derivation of Serum-Free MDCK Cells in Taub's Media

The results detailed Example 2 above demonstrate that MDCK cells can be cultivated under conditions that maintain their epithelial morphology and normal karyology as well as their ability to replicate cold adapted influenza strains. In addition, we demonstrated that cultivation of MDCK cells under the conditions developed in the above study results in MDCK cells that are non-tumorigenic. However, the culture medium used in Example 2 contains fetal bovine serum (FBS). FBS is a complex mixture of constituents and there have been problems reported of lot-to-lot variation. Also, the ongoing problems with bovine spongiform encephalopathy (BSE) in cows raise safety concerns. The development of serum-free medium in which the non-tumorigenic nature and growth characteristics of the MDCK-S cell line is maintained is important for increasing the safety of biologicals produced for therapy and vaccination.

Figure 8:
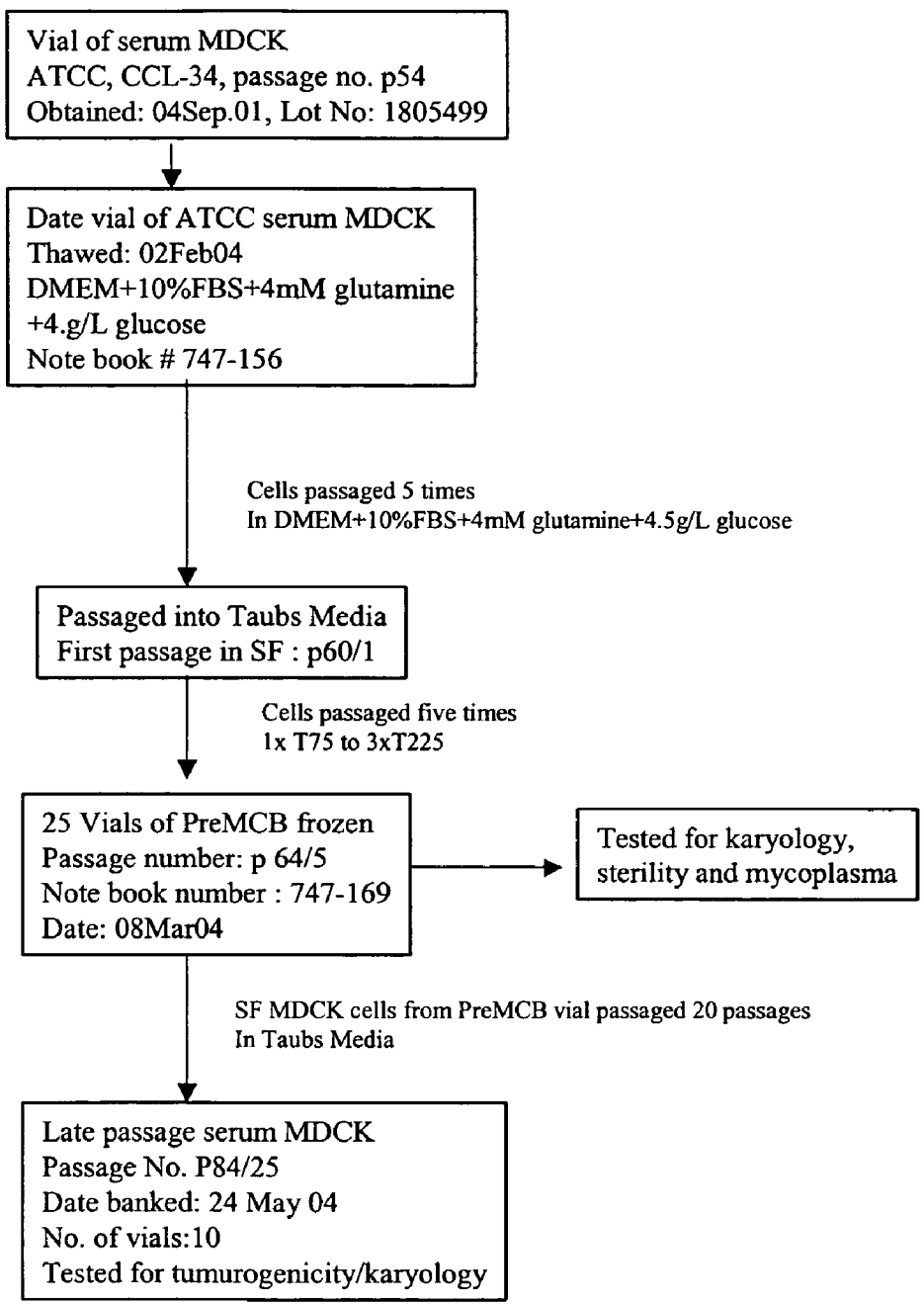
FIG. 8 outlines the process used for the derivation of MDCK-T PreMCB (passage No. 64/5). The process is described in detail in Example 3.

Madin Darby Canine Kidney Cells (MDCK) cells obtained from the ATCC (ccl 34) were expanded in T-flasks using DMEM supplemented with 10% FBS, 4 mM glutamine and 4.5 g/L glucose as the growth medium for 5 passages. The cells were then transferred to serum-free Taub's media (see below for formulation). The cells adapted to grow in the Taub's media formulations were designated MDCK-T. A pre-MCB was established for the MDCK-T cells (see FIG. 8) and was tested for bacterial/fungal contaminants and mycoplasma contamination. The cells the MDCK-T cell pre-Master cell bank were also tested by a karyotype assay found to be canine in origin and had a modal chromosome number of 78 with chromosome numbers ranging from 52 to 84. In addition, the MDCK-T cells were passaged for at least another 20 passages from a vial of PreMCB and tested for karyology and tumorigenicity in an vivo adult nude mice model. However, the MDCK-T cells were found to be tumorigenic in this model indicating that the published Taub's media did not support the stable cultivation of MDCK cells for the production of human vaccine material.

Materials and Methods

Materials: MDCK cell (ATCC, Cat. No: CCL-34, passage 54); T-25, T-75, T-225 flasks (Corning, Cat No.: 430639, 430641, 431082); Dulbecco's Modified Eagle's Medium (DMEM) powder (Gibco, Grand Island N.Y., Formulation No.: 01-5052EF); Ham F12 Nutrients mixture powder (Gibco, Grand Island N.Y., Cat. No.: 21700-075); Fetal Bovine Serum, Gamma-irradiated (JRH, Lenexa Kans., Cat. No.: 12107-500M); L-Glutamine (JRH, Lenexa Kans., Cat. No.: 59202-100M); D-Glucose (Amresco, Cat. No.: 0188-1KG); Dulbecco's Phosphate buffered saline (DPBS) without $Ca^{2+}$ and $Mg^{2+}$ powder (Gibco, Grand Island N.Y., Cat. No.: 21600-069); Insulin powder (Serological, Cat. No. 4506); Transferrin (APO form) (Gibco, Grand Island N.Y., Cat. No.: 11108-016); Prostaglandin E1 (Sigma, St. Louis Miss., Cat. No.: P7527); Hydrocortisone (Mallinckrodt, Cat. No.: 8830(-05)); Triiodothyronine (Sigma, St. Louis Miss., Cat. No.: T5516); Sodium Selenium (EMD, Cat. No.: 6607-31); 0.05% Trypsin-EDTA (Gibco, Grand Island N.Y., Cat. No.: 25300); Lima bean trypsin inhibitor (Worthington, Cat. No.:LS002829); Dimethylsulphoxide, DMSO (Sigma, St. Louis Miss., Cat. No.: D2650); 0.4% w/v Trypan blue dye in PBS (Sigma, St. Louis Miss., Cat. No.: T8154); Improved Neubaurr hemacytometer (Hausser Scientific, Brightline 0.1 mm deep/Reichert, Brightline 0.1 mm deep); YSI Bioanalyzer (YSI, Model No.: 2700 select); Vitro Chemistry System (Ortho clinic, Model: DT60 II).

Formulation of Taub's Serum-free Media: Taub's media (Taub and Livingston, 1981, *Ann NY Acad. Sci.*, 372:406) is a serum-free media formulation that consists of DMEM/HAM F12 (1:1) containing 4.5 g/L glucose and 4 mM glutamine as the basal media formulation, to which the hormones/factors are added as indicated in Table 3.

TABLE 3

Hormones and growth factors added to serum-free media formulations

| Name of Component | Final Concentration |
|---|---|
| Insulin | 5 µg/mL |
| Transferrin | 5 µg/mL |
| Triiodothyronine ($T_3$) | $5 \times 10^{-12}$ M |
| Hydrocortisone | $5 \times 10^{-8}$ M |
| Prostaglandin $E_1$ | 25 ng/mL |
| Sodium Selenite | $10^{-8}$ M |

Taub's SFM is made fresh at the time of passaging or refeed by the addition of stock solutions of hormone supplements to SF DMEM/Ham F12 medium+4 mM glutamine+4.5 g/L glucose+$10^{-8}$ M sodium selenite. 100 mL of Taubs Media is made by addition of 100 µL of insulin stock (5 mg/mL) solution, 100 µL transferrin stock solution (5 mg/mL), 100 µL triiodothyronine (T3) stock solution ($5\times10^{-9}$ M), 5 µL of hydrocortisone stock solution ($10^{-3}$ M) and 50 µL of prostaglandin E1 stock solution (50 µg/mL) to basal DMEM/Ham F12 medium+4 mM glutamine+4.5 g/L glucose+$10^{-8}$ M sodium selenite. All stocks solutions are prepared as follows:

Insulin Stock Solution—A 5 mg/ml stock solution is made by dissolving the appropriate amount of insulin in 0.01 N HCl. The solution is passed through a 0.2 micron sterilizing grade filter and aliquoted into Nalgene cryovial and stored at 4° C.

Transferrin Stock Solution—A 5 mg/ml stock solution is made by dissolving the appropriate amount of transferrin in MilliQ water. The solution is passed through a sterilizing grade filter and then aliquoted into Nalgene cryovial and store <–20° C. Triiodothyronine ($T_3$) Stock Solution—A stock solution is made by dissolving the appropriate amount of T3 in 0.02 N NaOH to obtain a $10^{-4}$ M solution. This is stock solution is further diluted to a concentration of $5\times10^{-9}$ M stock solution with 0.02 N NaOH, passed through a sterilizing grade filter, aliquoted into Nalgene cryovial and stored at <–20° C.

Hydrocortisone Stock Solution—A $10^{-3}$ M stock solution is made by dissolving the appropriate amount of hydrocortisone in 100% EtOH and aliquoted into Nalgene cryovials. The vials are stored at 4° C. for 3-4 months.

Prostaglandin $E_1$ Stock Solution—A 50 µg/mL stock solution made by dissolving the appropriate amount of PGE1 in 100% sterile EtOH and aliquoted into Nalgene cryovial and stored at <–20° C.

$Na_2SeO_3$ Stock Solution—A $10^{-2}$ M stock solution is made by dissolving the appropriate amount of sodium selenide in WFI water or MilliQ water. This is further diluted in water to a final concentration of $10^{-5}$ M passed through a sterilizing grade filter and stored at 4° C.

Adaptation of MDCK-S cells into Serum-free Taub's media: A frozen vial of MDCK cells from ATCC (passage 54) was grown in 10% FBS DMEM medium with 4.5 g/L glucose, 2.2 g/L $NaHCO_3$ and 4 mM L-glutamine for 5 passages (as described above) before passaging into a serum-free Taub's media. Serum MDCK grown in a T-75 flask were recovered by trypsinization. The spent growth medium was removed and cell monolayer washed twice with DPBS (calcium and magnesium free) and then DPBS was discarded. The appropriate amount of pre-warmed trypsin-EDTA (3 mL/T-75) was added and the T-flask was incubated in a 37° C., 5% $CO_2$ incubator for about 15 min. The flasks were rapped against the palm of the hand several times to completely detach the cells. Equal volume of lima bean trypsin inhibitor was added to neutralize the trypsin and two samples were taken to determine concentration of cells in the cell suspension. $1.75 \times 10^6$ cells were then diluted into 35 mL Taub's media in a fresh T75 flask. The flask was placed in an cell culture incubator maintained at 5% $CO_2$, $37 \pm 1°$ C. The cells were either subcultured 3 days post seeding or a complete medium exchange was performed on day 3 followed by subculturing on day 4 postseeding.

Subculturing of Taub's media Adapted MDCK cells: The spent growth medium was removed and cell monolayer washed twice with DPBS (calcium and magnesium free). The appropriate amount of pre-warmed trypsin-EDTA (3 mL/T-75, 7.5 mL/T-225) was added and the T-flask was incubated in a 37° C., 5% $CO_2$ incubator for about 15 min. The flasks were rapped against the palm of the hand several times to completely detach the cells. The trypsin was then inhibited by addition of equal volumes of lima bean trypsin inhibitor (3 mL/T-75, 7.5 mL/T-225). The cell suspension was homogenized by aspirating up and down with an appropriately sized pipette. Two 0.5 mL samples of cell suspension were taken for cell counting. The cell counts were repeated if the results of the two counts were not within 15% of each other. After counting, the cells were diluted to $0.05 \times 10^6$ viable cells/mL in fresh prewarmed Taub's media in fresh flasks, for a total volume of 35 mL/T75 or 100 mL/T-225. The flasks were then incubated in a $37 \pm 1°$ C., 5% $CO_2$ environment. Cells were either subcultured to new T-flasks on day 3 (as described below) or a complete media exchange was performed and the culture subcultured to new T-flasks on day 4 post seeding.

Preparation of Taub's media Adapted MDCK cell PreMCB Banks: The pre-master cell banks for the Taub's serum-free adapted MDCK cell line (MDCK-T) were prepared as described in Example 2 above, except that the 2× freezing medium was Taub's media+15% DMSO.

Characterization of Taub's media Adapted MDCK (MDCK-T) cells: Karyology, sterility and mycoplasma testing of the MDCK-T preMCB was performed as described in Example 2 except that Taub's media was used in place of serum containing complete media. In addition the growth curve characteristics of MDCK-T cells in T-75 flasks and the replication of cold adapted influenza strains in MDCK-T cells were examined as described in Example 2 except that Taub's media was used in place of serum containing complete media. Tumorigenicity studies were performed on MDCK-T cells at passage 88/29 (pre-MCB+20 passages) by BioReliance as described in Example 2 above.

Results and Discussion

Figure 9:
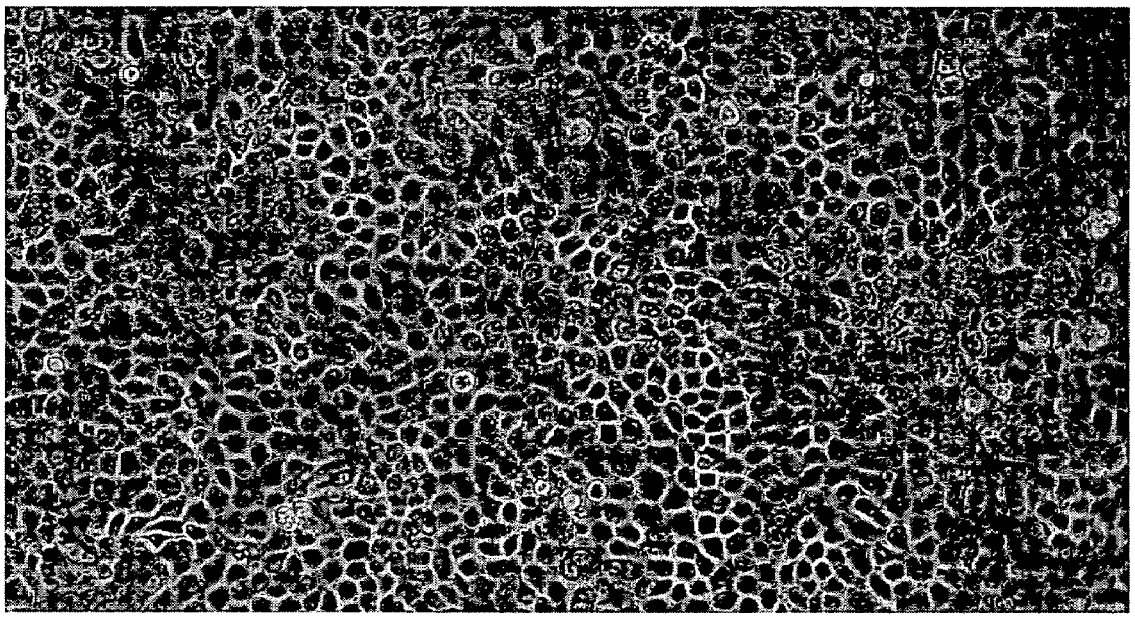
FIG. 9 is a photograph showing that MDCK-T cells have an epithelial-like morphology. The photo was taken 3 days after seeding.

A frozen vial of MDCK-T preMCB (passage 64/5) cells was thawed into serum-free Taub's media in T-75 flasks. The cell viability was 97% and $5.25 \times 10^6$ cells were recovered from frozen vial upon thawing. Cells were confluent three days after thawing. Cell morphology showed epithelia-like cells similar to the parent MDCK-S cells. (FIG. 9).

Figure 10:
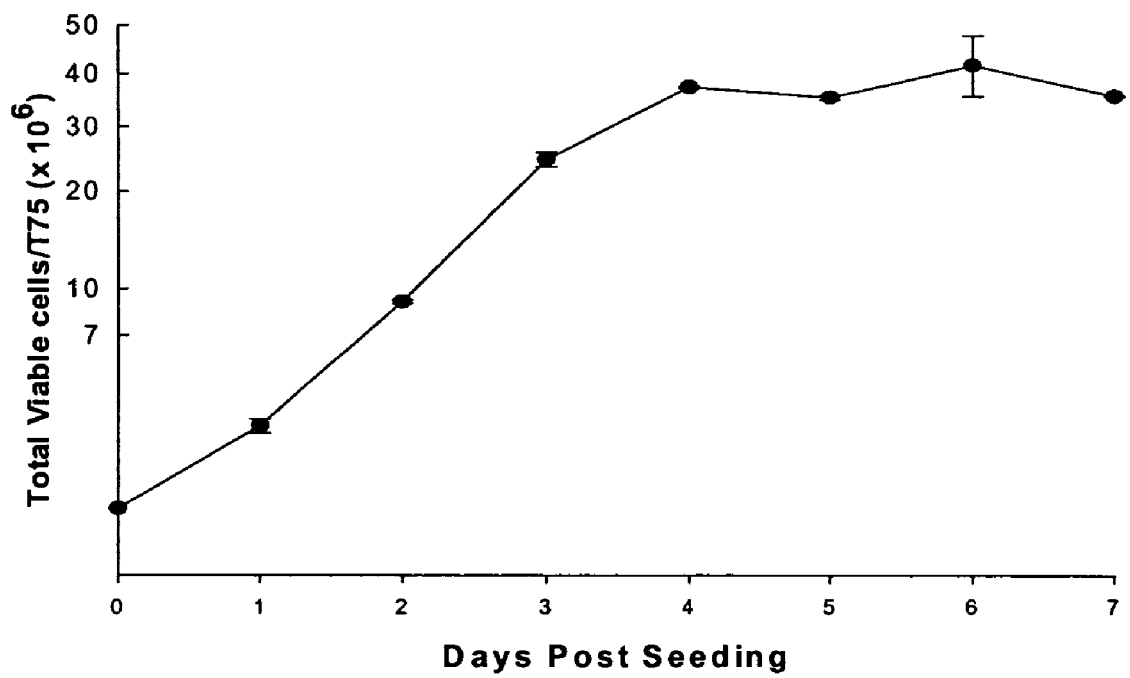
FIG. 10 is the growth curve of MDCK-T cells in Taub's media. Cells had no lag phase and were in exponential growth until entering stationary phase at day 4 post seeding.

The growth curves for MDCK-T cells in Taub's SF medium are showed in FIG. 10. The results are the average of two experiments using cells at different passage numbers (P71/12 & P73/14). MDCK-T cells had no lag phase with cells doubling one day post seeding ($3.42 \times 10^6$ total cell/T75 flask day 1 versus $1.75 \times 10^6$ total cell/T75 flask on day 0). The cells were in the exponential phase of growth till day 4, when they entered into the stationary phase. The doubling time of cells in the exponential phase was 20.4 hrs. During the exponential phase (day 0 to day 4) they utilized glucose and glutamine (FIGS. 11 and 12) while producing lactate and ammonia. The glucose consumption/lactate production rate correlated well with the cell growth curve (compare FIGS. 10 and 11). The glucose consumption rate was 1.78 mM/day during the exponential phase from day 0 to day 4 and lactate was produced at a rate of 2.88 mM/day. MDCK-T cells only consumed about a total of 10 mM glucose in the medium up to 7 days culture. The ratio of amount of glucose consumed to lactate produced at day 4 post seeding was 1.2. The rate of glucose consumption and lactate production slowed down after day 4 when cells entered into the stationary phase, with the glucose consumption being 0.65 mM/day and lactate being produced at a rate of 0.46 mM/day. The maximum cell density of $37 \pm 0.24 \times 10^6$ was achieved around day 4 post seeding. The cell density did not drop during the stationary phase and remained constant till day 7.

Figure 11:
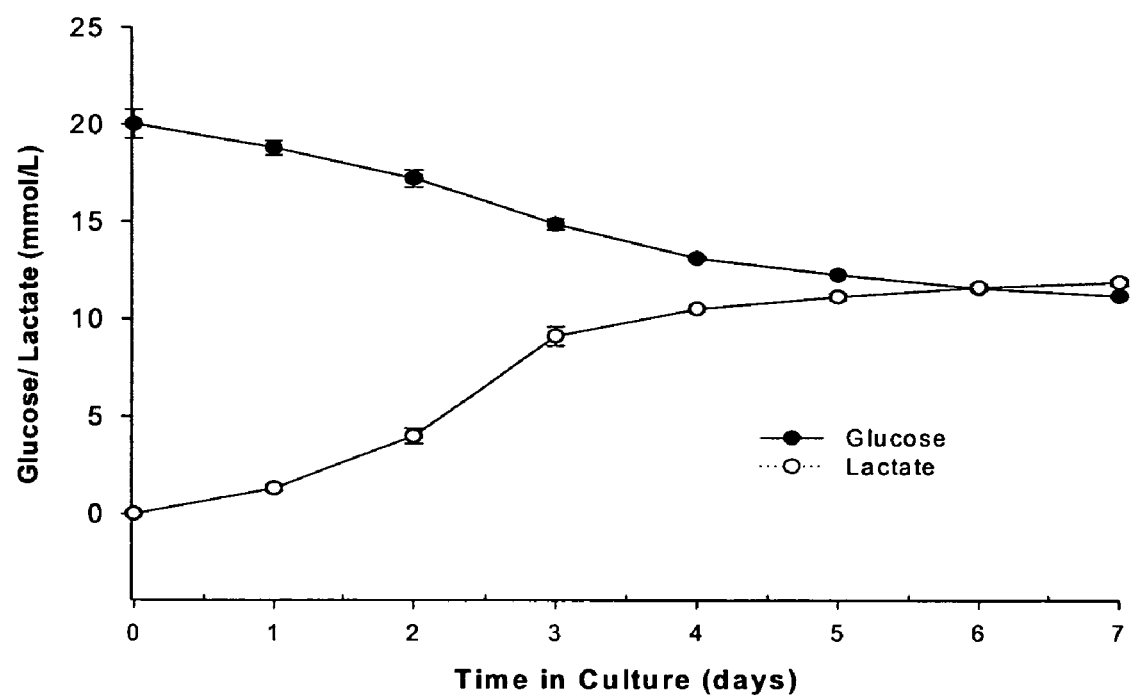
FIG. 11 is a graph of the glucose consumption and lactate production of MDCK-T cells in Taub's media. During the exponential phase the rates were 1.78 mM/day and 2.88 mM/day for glucose and lactate, respectively.
Figure 12:
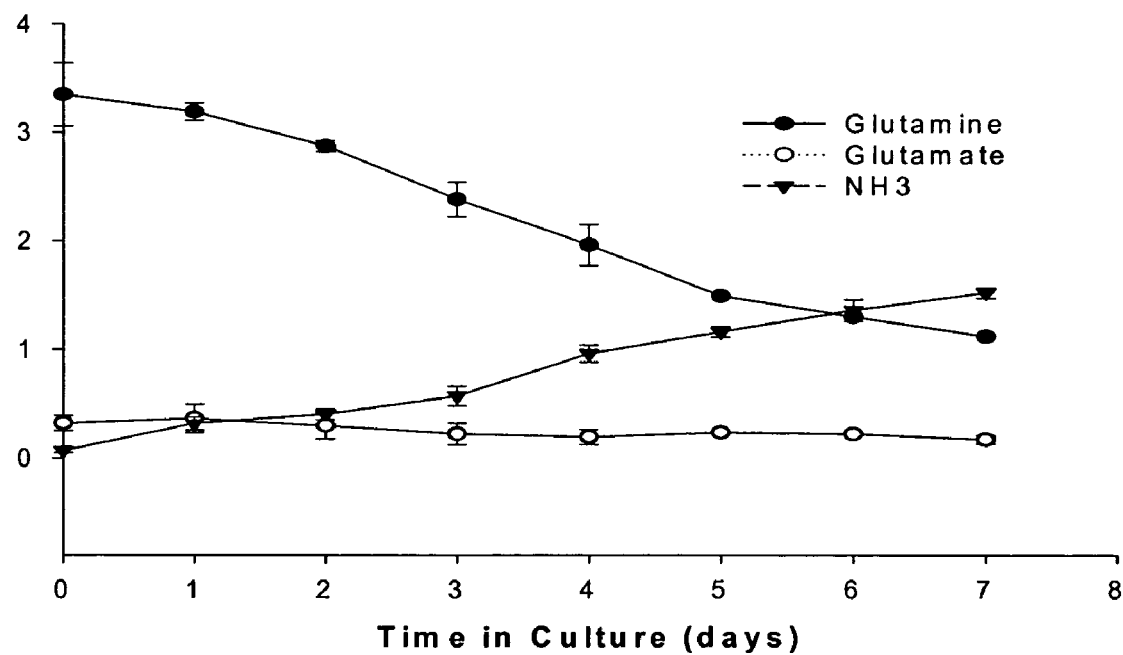
FIG. 12 is a graph of the glutamine consumption and both glutamate ammonia production of MDCK-T cells in Taub's media. The glutamine consumption rate was 0.36 mM/day up to day 4 and the ammonia production rate increased linearly up to day 7 at a rate of 0.22 mM/day. Glutamate did not accumulate in this study.

The glutamine consumption rate and ammonia production rate were similar to the MDCK-T cell growth and glucose/lactate profiles (compare FIGS. 10, 11 and 12). The MDCK-T cells consumed glutamine at a rate of 0.36 mM/day during the exponential growth phase (day 0 to day 4) with the rate dropping to 0.27 mM/day when the cells entered the stationary phase (day 4 to day 7). Ammonia production increased linearly up to day 7 at rate of 0.22 mM/day. The ratio of ammonia production to glutamine consumption was 0.49 on day 4 post seeding. Glutamate concentration did not change appreciably during the entire 7 day period.

MDCK-T cells were tested for their ability to support ca/ts influenza replication as per example 2. The results shown in Table 2 indicate that MDCK-T cells were able to support the replication of ca/ts influenza replications to levels nearly the same as seen for the MDCK-S cells.

Figure 13:
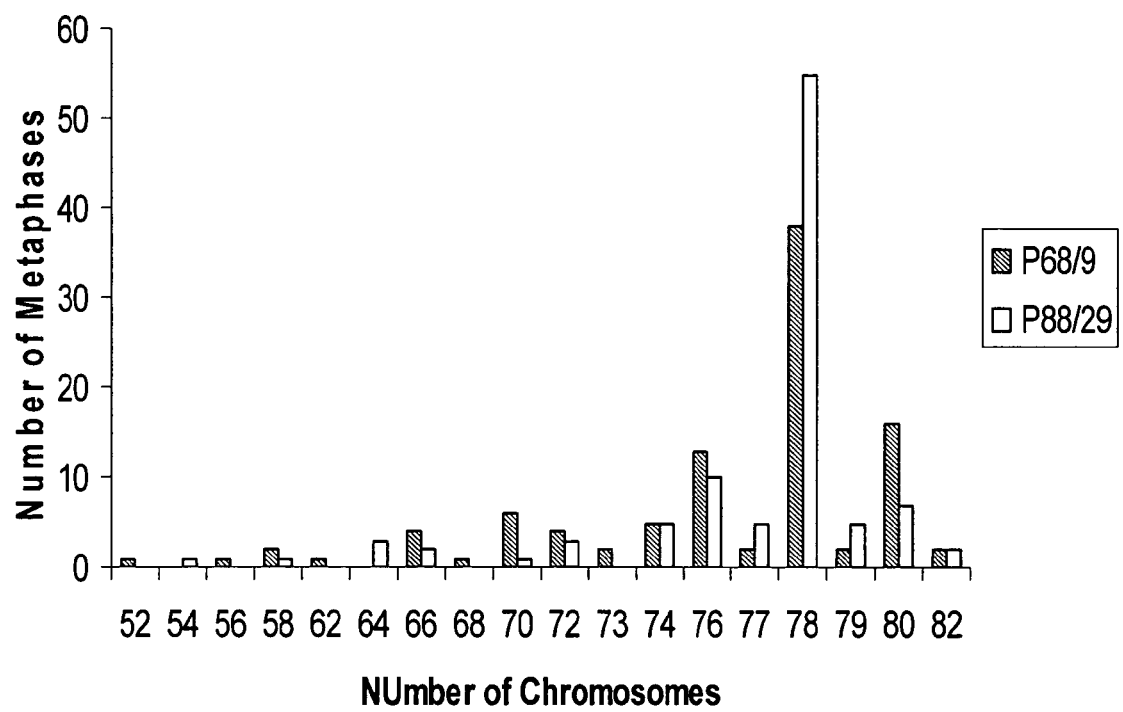
FIG. 13 is a plot of the distributions of chromosome number in 100 metaphase low passage (P61/4) and high passage (P81/24) MDCK-T cells. The chromosome count ranged from 52 to 82 per metaphase for low passage cells and from 54 to 82 for high passage cells.

MDCK-T cell karyology was tested at passage 68/9 and passage 88/29. The G-band chromosome analysis showed that the cells were canine in origin. The distributions of chromosome number in 100 metaphases cells were shown in FIG. 13. The chromosome count ranged from 52 to 82 chromosomes per metaphase for cells at low passage 68/9, range from 54 to 82 chromosomes for high passage 81/24 indicating that the distribution of chromosomes did not change with passaging. However, it can be seen that the MDCK-T cells show a wider spread in chromosome number (52 to 84) as compared to the MDCK-S cells (70-84).

The MDCK-T preMCB was tested for presence any bacterial, fungal or mycoplasma contaminants. The MDCK-T pre-MCB was passed sterility test (four media sterility test using direct inoculation method to check bacterial and fungal contaminants) and was found to be negative for presence of mycoplasma (agar-cultivable and non-agar cultivable assay). The test article was also found not to inhibit the growth of positive controls in both the bacteriostasis/fungistatis test and mycoplasmstatis test.

MDCK-T cells at passage 88/29 (pre-MCB+20 passages) were put on nude mice for tumorigenicity test for 3 months. The test article was diagnosed as adenocarcinomas at the site of injection in six of ten test article mice. This shows that the MDCK cells grown in SF Taubs media are tumorigenic. The tumorigenicity, estimated TP50 and karyology for MDCK-S and MDCK-T cells is summarized in Table 4 below.

Example 4

Derivation of Serum-Free MDCK Cells in MediV Serum-Free Medias:

The results detailed in Example 3 demonstrate that, although MDCK cells adapted to grow in serum-free Taub's media (MDCK-T) had excellent growth characteristics and were able to support the replication of ca/ts influenza strains, they were tumorigenic. Thus, these results indicate that MDCK cells can readily become transformed in the standard serum-free media formulations reported in the literature. In accordance with the invention, several additional serum-free media formulations were developed and tested for their ability to maintain the non-tumorigenic nature of the MDCK-S cells. MDCK-S cells were adapted to each of the new serum-free formulations designated MediV SFM 101, 102 and 103. These serum-free adapted cell lines were designated MDCK-SF101, -SF102 and -SF103, respectively and are referred to as "MDCK-SF", collectively. PreMCBs were generated for each MDCK-SF adapted cell line. The MDCK-SF cell line preMCBs were tested for bacterial/fungal contaminants and mycoplasma contamination (awaiting final results). The MDCK-SF preMCBs were also tested by a karyotype assay, MDCK-SF101 and MDCK-SF102 cells had a modal chromosome number of 78 with chromosome numbers ranging from and 70 to 82 and 60 to 80, respectively. In addition, the cells from each serum-free media bank were passaged for at least another 20 passages from a vial of PreMCB and MDCK-SF103 was tested for karyology and tumorigenicity in an vivo adult nude mice model. At passage 87 MDCK-SF103 was found to have a modal chromosome number of 78 ranging from 66 to 80 and were deemed to be non tumorigenic.

Materials: MDCK cell (ATCC, Cat. No: CCL-34, passage 54); T-25, T-75, T-225 flasks (Corning, Cat No.: 430639, 430641, 431082); Dulbecco's Modified Eagle's Medium (DMEM) powder (Gibco, Grand Island N.Y., Formulation No.: 01-5052EF); Ham F12 Nutrients mixture powder (Gibco, Grand Island N.Y., Cat. No.: 21700-075); Fetal Bovine Serum, Gamma-irradiated (JRH, Lenexa Kans., Cat. No.: 12107-500M); L-Glutamine (JRH, Lenexa Kans., Cat. No.: 59202-100M); D-Glucose (Amresco, Cat. No.: 0188-1KG); Dulbecco's Phosphate buffered saline (DPBS) without $Ca^{2+}$ and $Mg^{2+}$ powder (Gibco, Grand Island N.Y., Cat. No.: 21600-069); Insulin powder (Serological, Cat. No. 4506); Transferrin (APO form) (Gibco, Grand Island N.Y., Cat. No.: 11108-016); Prostaglandin E1 (Sigma, St. Louis Miss., Cat. No.: P7527); Hydrocortisone (Mallinckrodt, Cat. No.: 8830(-05)); Triidothyronine (Sigma, St. Louis Miss., Cat. No.: T5516); Sodium Selenium (EMD, Cat. No.: 6607-31); 0.05% Trypsin-EDTA (Gibco, Grand Island N.Y., Cat. No.: 25300); Lima bean trypsin inhibitor (Worthington, Cat. No.:LS002829); Dimethylsulphoxide, DMSO (Sigma, St. Louis Miss., Cat. No.: D2650); 0.4% w/v Trypan blue dye in PBS (Sigma, St. Louis Miss., Cat. No.: T8154); Improved Neubaurr hemacytometer (Hausser Scientific, Brightline 0.1 mm deep/Reichert, Brightline 0.1 mm deep); YSI Bioanalyzer (YSI, Model No.: 2700 select); Vitro Chemistry System (Ortho clinic, Model: DT60 II).

Formulation of MediV Serum-free Medias (MediV SFM 101, 102 and 103): Each MediV serum-free media formulation uses Taub's media (see the methods section of example 2 above) as a basal media and adds supplements as follows:

MediV SFM 101: Taub's+2.5 g/L Wheat Peptone E1 from Organo Techine (cat no 19559). Wheat Peptone E1 is stored in water as a sterile 250 g/L stock solution.

MediV SFM 102: Taub's+100× chemically defined lipid concentrate from GIBCO BRL (cat no. 11905) added to a final concentration of 1X.

MediV SFM 103: Taub's+1× final concentration lipid concentrate from GIBCO+2.5 g/L Wheat Peptone E1 from Organo Technie.

Medi SFM 104: Taub's+1× final concentration lipid concentrate from GIBCO+2.5 g/L Wheat Peptone E1 from Organo Technie+0.01 μg/mL EGF (multiple sources).

Medi SFM105: Taub's without Transferrin, +1× final concentration lipid concentrate from GIBCO+2.5 g/L Wheat Peptone E1 from Organo Technie+0.01 μg/mL EGF+Ferric ammonium citrate:Tropolone or Ferric ammonium sulfate:Tropolone at a ratio of between 10 to 1 and 70 to 1.

Adaptation of MDCK-S cells into Serum-free MediV SFM media formulations: A frozen vial of MDCK cell from ATCC was grown in 10% FBS DMEM medium with 4.5 g/L glucose, 2.2 g/L $NaHCO_3$ and 4 mM L-glutamine for 5 passages (as described above) before passaging into a MediV SFM media formulation (MediV SFM 101, MediV SFM 102 or MediV SFM 103). Serum MDCK grown in a T-75 flask were recovered by trypsinization. The spent growth medium was removed and cell monolayer washed twice with DPBS (calcium and magnesium free) and then DPBS was discarded. The appropriate amount of pre-warmed trypsin-EDTA (3 mL/T-75) was added and the T-flask was incubated in a 37° C., 5% $CO_2$ incubator for about 15 min. The flasks were rapped against the palm of the hand several times to completely detach the cells. Equal volume of lima bean trypsin inhibitor was added to neutralize the trypsin and two samples were taken to determine concentration of cells in the cell suspension. $1.75 \times 10^6$ cells were then diluted into 35 mL of the desired MediV SFM media formulation in a fresh T75 flask. The flask was placed in an cell culture incubator maintained at 5% $CO_2$, 37±1° C. The cells were either subcultured 3 days post seeding or a complete medium exchange was performed on day 3 followed by subculturing on day 4 post-seeding. Cells maybe adapted to MediV SF104 and MediV SF105 using the same procedure described above.

Subculturing of MediV SFM media Adapted MDCK cells: The spent growth medium was removed and cell monolayer washed twice with DPBS (calcium and magnesium free). The appropriate amount of pre-warmed trypsin-EDTA (3 mL/T-75, 7.5 mL/T-225) was added and the T-flask was incubated in a 37° C., 5% $CO_2$ incubator for about 15 min. The flasks were rapped against the palm of the hand several times to completely detach the cells. The trypsin was then inhibited by addition of equal volumes of lima bean trypsin inhibitor (3 mL/T-75, 7.5 mL/T-225). The cell suspension was homogenized by aspirating up and down with an appropriately sized pipette. Two 0.5 mL samples of cell suspension were taken for cell counting. The cell counts were repeated if the results of the two counts were not within 15% of each other. After counting, the cells were diluted to $0.05 \times 10^6$ viable cells/mL in the appropriate fresh prewarmed MediV SFM media formulation in fresh flasks, for a total volume of 35 mL/T75 or 100 mL/T-225. The flasks were then incubated in a 37±1° C., 5% $CO_2$ environment. Cells were either subcultured to new T-flasks on day 3 (as described below) or a complete media exchange was performed and the culture subcultured to new T-flasks on day 4 post seeding. Note: MDCK-SF cells are always subcultured into the same MediV SFM media formulation as they were adapted to.

Preparation of MediV SFM media Adapted MDCK cell PreMCB Banks: The pre-master cell banks for the serum-free adapted MDCK cell lines are prepared as described in example 1 above, except that the 2× freezing medium is the appropriate MediV SFM media formulation+15% DMSO.

Characterization of MediV SFM media Adapted MDCK (MDCK-SF) cells: Karyology, sterility and mycoplasma testing of the MDCK-SF preMCBs are tested according to methodology described herein, e.g., in Example 2 except that the appropriate MediV SFM media formulation is used in place of serum containing complete media. Further, the growth curve characteristics of MDCK-SF cells in T-75 flasks and the replication of cold adapted influenza strains in MDCK-SF cells can be examined as described in Example 2 except that the appropriate MediV SFM media formulation is used in place of serum containing complete media. In addition, tumorigenicity studies can be performed on MDCK-SF cells after an additional number of passages (e.g., preMCB+20 passages) by a commercial contractor (e.g., BioReliance) as described in Example 2 above.

Results and Discussion

Figure 14:
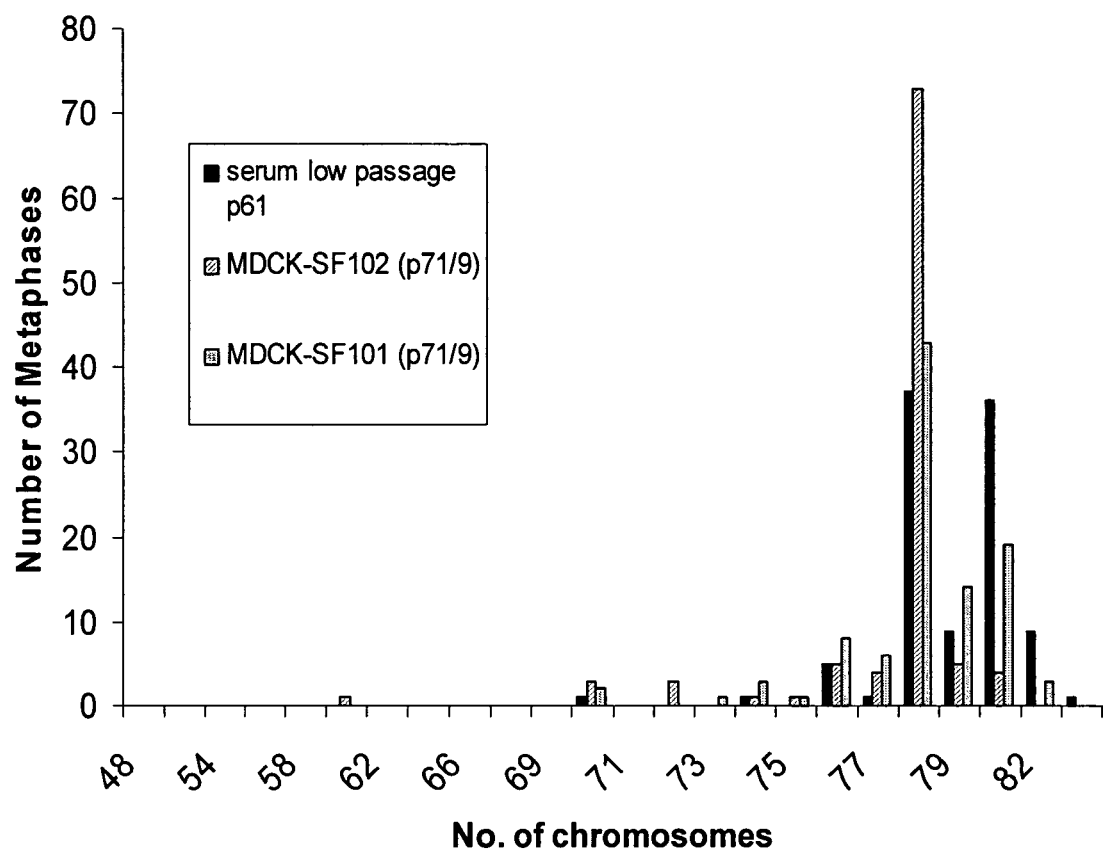
FIG. 14 is a plot of the distributions of chromosome number in 100 metaphase MDCK-T, MDCK-SF101 (passage 71/9) and MDCK-SF102 cells (passage 71/9). Both SF101 and SF102 cells had a modal chromosome number of 78, with the chromosome count ranging from 70 to 82 and 60 to 80 per metaphase for SF101 and SF102, respectively.
Figure 15:
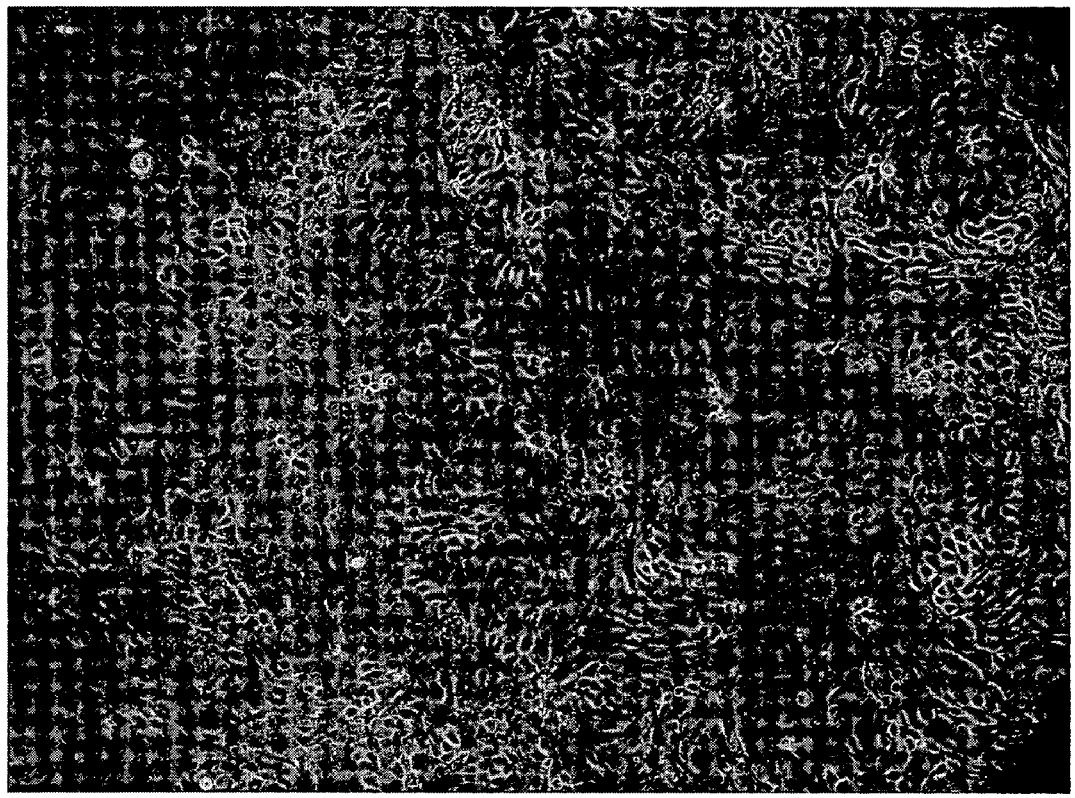
FIG. 15 is a photograph showing that MDCK-SF103 have an have an epithelial-like cell morphology. The photo was taken 3 days after seeding.
Figure 19:
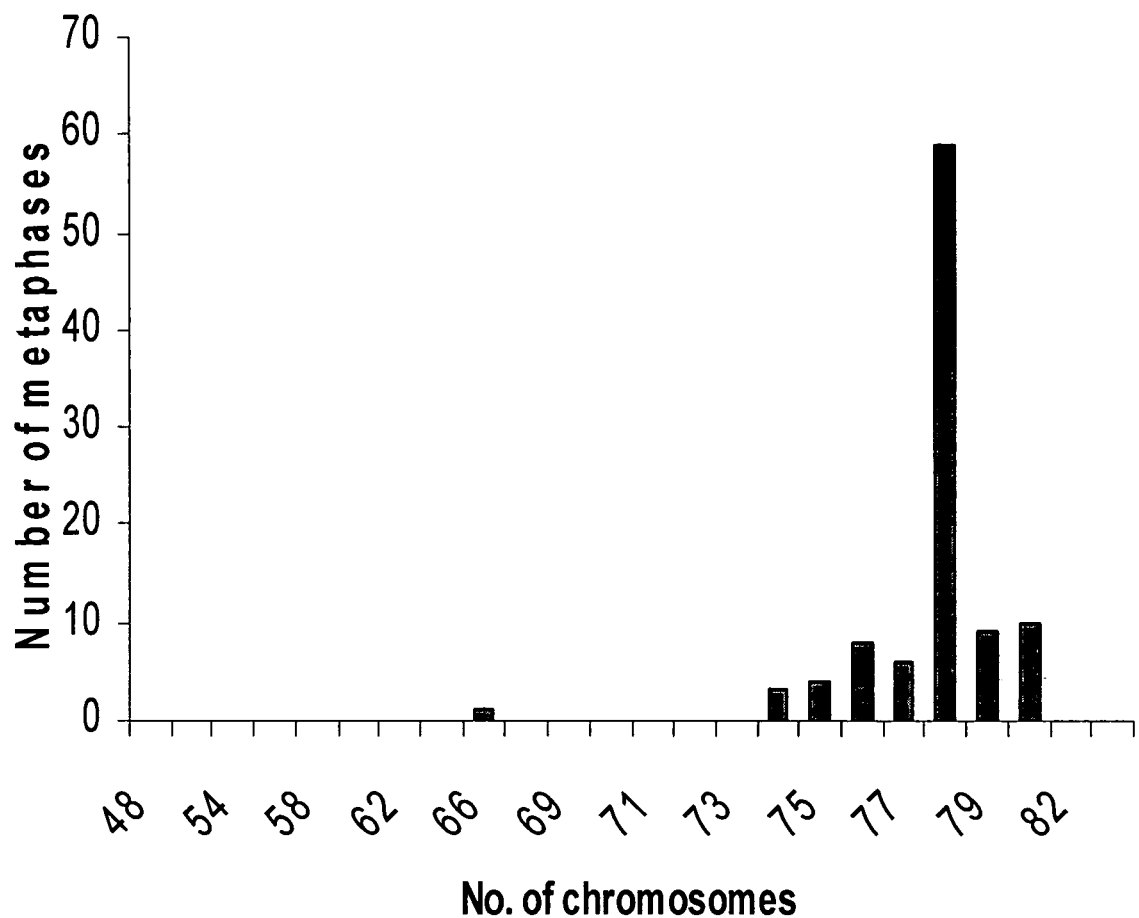
FIG. 19 is a plot of the distributions of chromosome number in 100 metaphase MDCK-SF103 cells at passage 87. SF103 cells had a modal chromosome number of 78, with the chromosome count ranging from 66 to 80.

The cell karyology of MDCK-SF101 and MDCK-SF102 cells was tested at passage 71/9 and of MDCK-SF103 at passage 87. The distributions of chromosome number in 100 metaphases of MDCK-T, MDCK-SF101 and MDCK-SF102 cells are shown in FIG. 14 and of MDCK-SF103 in FIG. 19. It can be seen that the MDCK-T cells show a wider spread in chromosome number (52 to 84) as compared to MDCK-SF111, MDCK-SF102 or MDCK-SF103 cells (70-82, 60-80, and 66-80 respectively). The spread in chromosome number for the MDCK-SF101, MDCK-SF102 and MDCK-SF103 cells is much closer to that seen for the non-tumorigenic MDCK-S serum grown cells (70-84) indicating that the MediV SF101, MediV SF102, and MediV SF103 media formulations are better able to maintain the normal chromosomal number of MDCK cells grown in these formulations.

Figure 16:
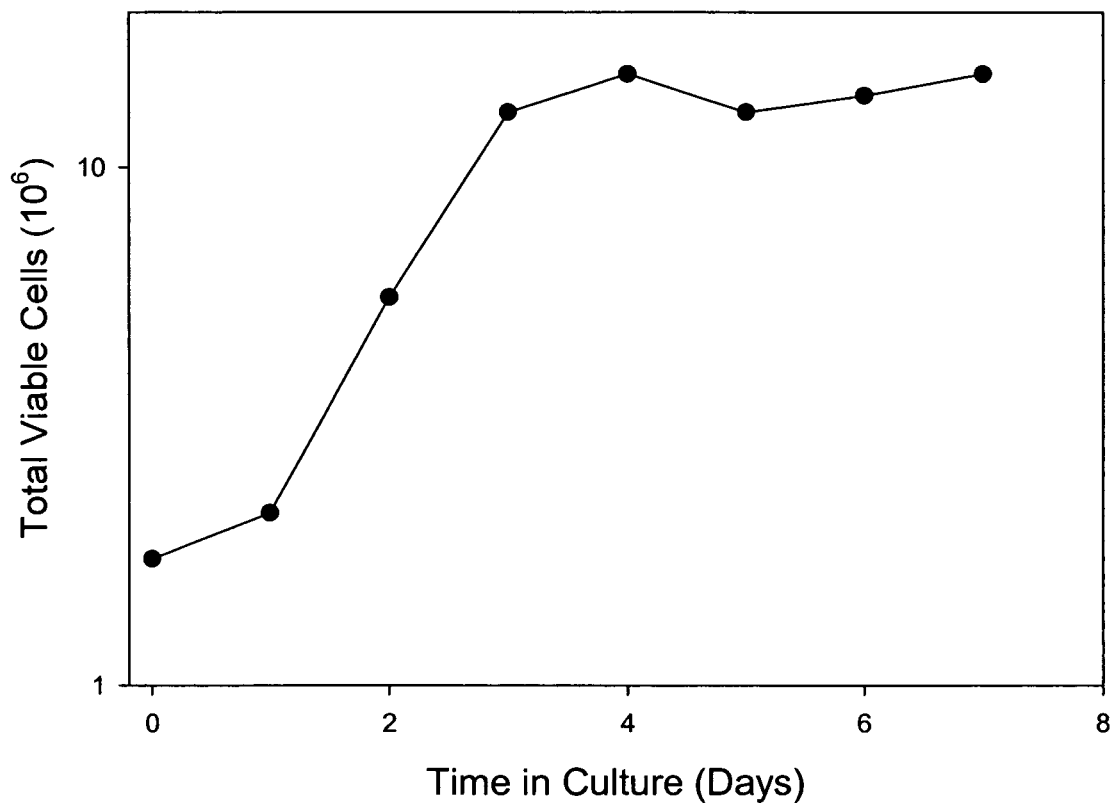
FIG. 16 is the growth curve of MDCK-SF103 cells in MediV SFM103. Cells had about a 1 day lag phase followed by exponential growth entering stationary phase at day 4 post seeding achieving a maximum density of ~17×10$^6$ cells on day 4.
Figure 17:
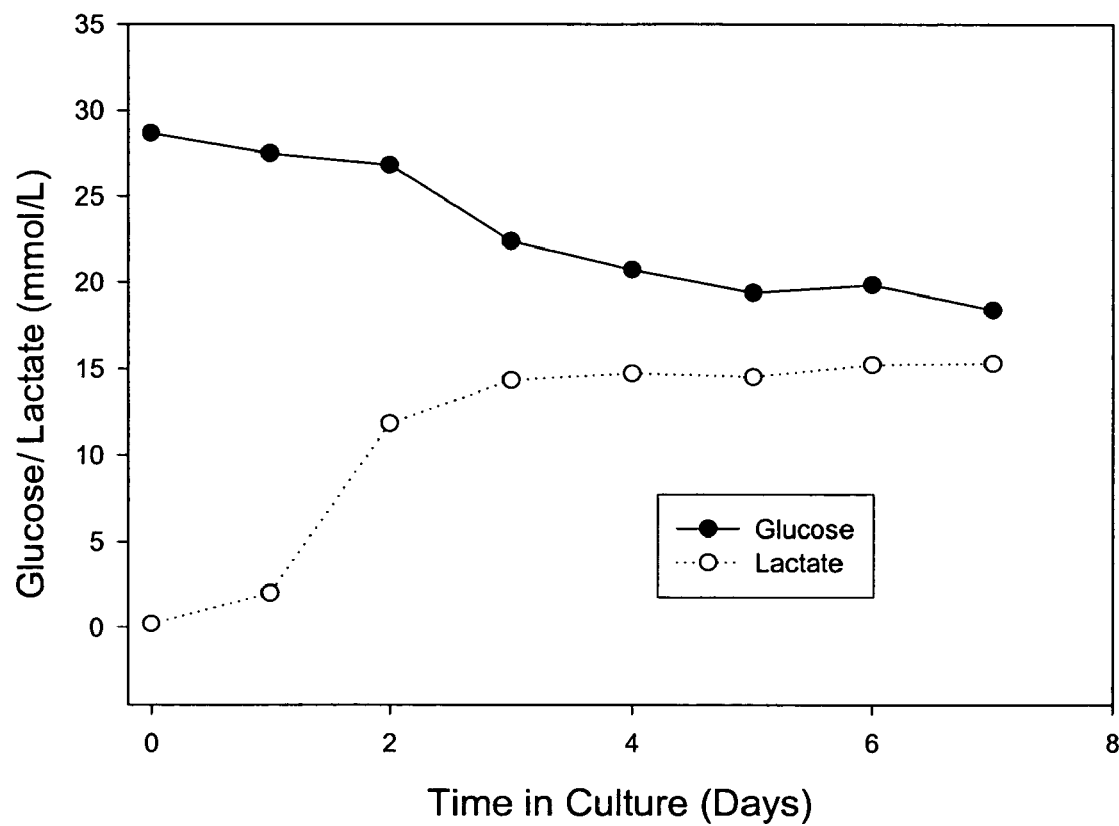
FIG. 17 is a graph of the glucose consumption and lactate production of MDCK-SF103 cells in MediV SFM103. During the exponential phase the glucose consumption and lactate production mirrored each other with lactate increasing in concentration as the glucose concentration decreased

A representative preliminary growth curve for MDCK-SF103 cells in MediV SF103 medium is showed in FIG. 16. MDCK-SF103 cells had about a one day lag phase. The cells were in the exponential phase of growth until about day 4, when they entered into the stationary phase. During the exponential phase (day 0 to day 4) they utilized glucose and glutamine (FIGS. 17 and 18) while producing lactate and ammonia. The glucose consumption/lactate production rate correlated well with the cell growth curve (see FIGS. 16 and 17). The maximum cell density of ~17×10$^6$ was achieved around day 4 post seeding. The cell density did not drop during the stationary phase and remained fairly constant till day 7.

Figure 18:
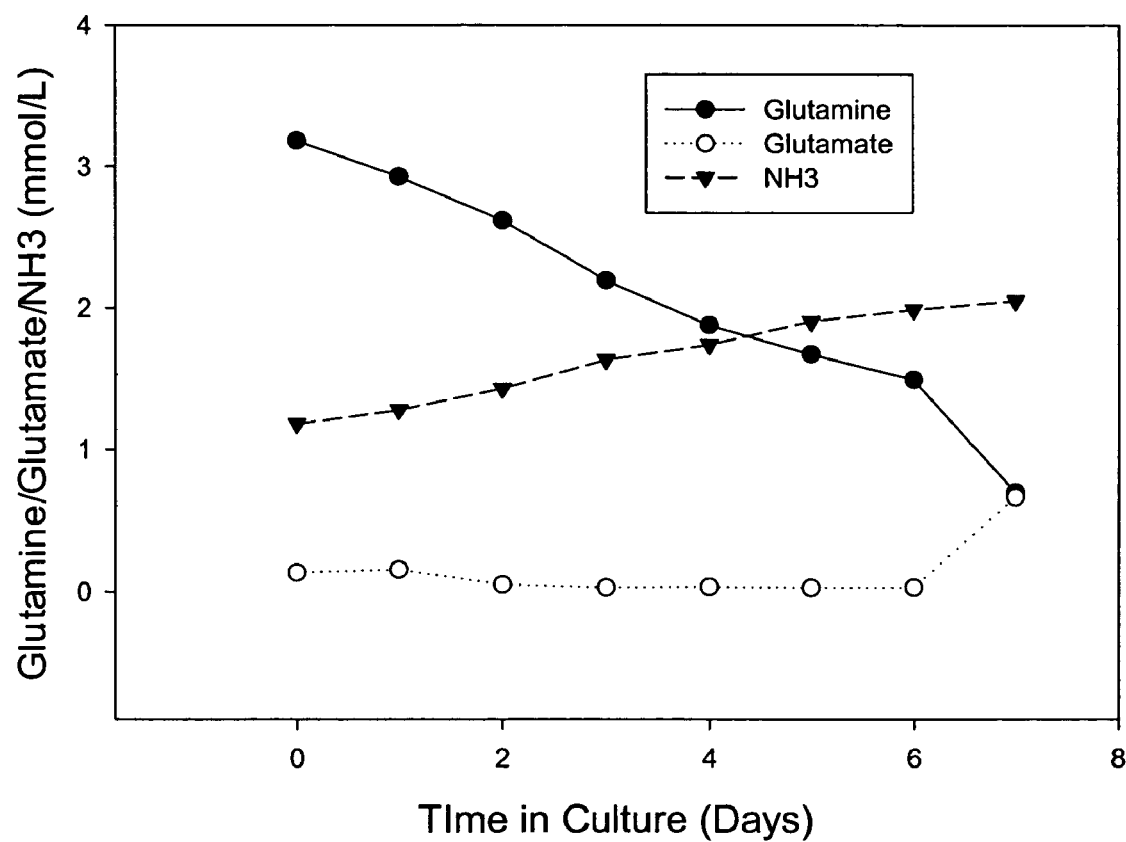
FIG. 18 is a graph of the glutamine consumption and both ammonia and glutamate production of MDCK-SF103 cells in MediV SFM103. The ammonia production rate increased nearly linearly up to day 7. Glutamate did not accumulate in this study.

The glutamine consumption rate and ammonia production rate were similar to the MDCK-SF103 cell growth and glucose/lactate profiles (see FIG. 18). Ammonia production increased linearly up to day 7 while the glutamate concentration did not change appreciably during the 7 day period.

MDCK-SF103 cells were tested for their ability to support the replication of several reassortant influenza strains as described in Example 7 below. The results shown in FIG. 20A indicate that MDCK-SF103 cells were able to support the replication of each influenza strain tested.

The MDCK-SF103 cells were put on nude mice for tumorigenicity test for 3 months as described above. The test article was deemed to be non-tumorigenic in the adult nude mouse model RioReliance Study Number AB09EU.001000.BSV).

TABLE 4

Tumorigenicity and Karyology of MDCK cells passed in different medias.

| Cells (passage number) | Tumorigenicity | Estimated TP$_{50}$* (no animals with tumors/ total animals) | Karyology Median number; comments |
|---|---|---|---|
| MDCK-S (P61/4) | ND | ND | 78; Few cells with anomalous chromosome number (70 to 82) |
| MDCK-S (P81/24) | No neoplasias. Fibrosarcomas at injection site | Not estimable (>10$^7$) (0/10) | 78; Few cells with anomalous chromosome number (70 to 82) |
| MDCK-T (P63/4) | ND | ND | 78; Large distribution of cells with chromosome number of 52 to 82 |
| MDCK-T (P88/29)) | Neoplasias noted | ~10$^7$ (6/10) | 78; Large distribution of cells with chromosome number of 52-82 |
| MDCK-SF101 | ND | ND | 78; Few cells with anomalous chromosome number (70 to 82) |
| MDCK-SF102 | ND | ND | 78; Few cells with anomalous chromosome number (60 to 80) |
| MDCK-SF103 | No neoplasias. Fibrosarcomas at injection site | Not estimable (>10$^7$) (0/10) | 78; Few cells with anomalous chromosome number (66 to 80) |

*TP$_{50}$: Number of cells required to induce tumors in 50% of animals
ND: Not done Example 5

Infection of Human Epithelial Cells in Culture

To evaluate the biochemical, biological, and structural similarities following replication of the MDCK and egg produced vaccines in cells of human origin, vaccines is passaged once in relevant diploid human cells, such as normal human bronchial epithelial cells (NHBE). This passage serves to mimic a single infection event in the human airway and then enable comparison of the progeny virus, the virus that is ultimately responsible for eliciting an effective immune response. Studies of the vaccines' hemagglutinin (binding and fusion) and neuraminidase activities are measured on these materials as well as other biochemical and structural studies including electron microscopy, infectious to total particle ratios, and viral genome equivalents are evaluated. Overall, these comparisons serve to demonstrate the comparability of the cell-derived vaccine to the effective and safe egg produced vaccine. Methods for testing for the presence of bacterial and fungal contaminants are well known in the art and routinely performed by commercial contractors (e.g., BioReliance®, Rockville, Md.). A summary of analytical studies which may be performed is summarized in Table 5.

TABLE 5

Preclinical Studies To Compare Cell And Egg Produced Vaccines

In vivo (ferrets)

Attenuation/Replication

Extent of replication in upper airway
Kinetics of replication in upper airway

TABLE 5-continued

Preclinical Studies To Compare Cell And Egg Produced Vaccines

Immunogenicity

Cross-reactivity
Kinetics
Infectivity

Dose required for detectable replication
Dose required for antibody response
In vitro*

Virus binding

Hemagglutination titer
Binding of different sialic acids
Phyical properties

Morphology by EM
Infectious: Total particles (genomes)
Fusion activity pH optimum
temperature optimum
Genomic sequence
Neuraminidase activity

Example 6

Production, Testing and Characterization of a Master Cell Bank

To initiate the generation of a master cell bank (MCB) cells from one or more of the preMCBs described above (see, Examples 2-4) are biologically cloned through limiting dilution in order to ensure that the production cells are derived from a unique genetic constellation. Clones are then screened for various phenotypic properties including doubling time and relative tumorigenicity, as well as viral production. In an initial proof of concept experiment, fifty-four MDCK clones were obtained in media containing FCS. These clones were passaged and each was infected with a low multiplicity of infection of ca A/New Calcdonia/20/99. Several days after infection, the supernatant was removed and the quantity of virus in the supernatant was measured by $TCID_{50}$. A minority of the clones produced relatively high titers of virus, greater than was produced in the noncloned parental cells. Clones with superior biological and physiological properties are used to establish a Master Cell Bank (MCB).

The MCB is extensively tested to ensure that there is no evidence of adventitious agents. For example, one or more of several PCR and/or antibody-specific tests for available viral agents are conducted, as shown in Table 6, below.

TABLE 6

Testing Regimen For a MCB

General tests

Sterility
Mycoplasma
Adventitious agents in vitro (multiple cell lines)
Adventitious agents in vivo
PERT
Co-cultivation
Karyology
Electron microscopy
Tumorigenicity intact cells ($TP_{50}$)
Oncogenicity of cellular DNA

TABLE 6-continued

Testing Regimen For a MCB

Oncogenicity of cellular lysate
Bovine viruses per 9CFR
Porcine viruses per 9CFR
PCR*/Ab specific AAV Types 1 & 2
HCMV
EBV
HSV
Hepatitis B, C & E
HHV 6, 7 & 8
HIV 1 & 2
HPV
HTLV I & II
Polyoma (BK and JC viruses)
Circovirus
Canine Parvovirus
Canine distemper
Adenovirus
SV40

Example 7

Process and Formulation of Vaccine Material

Figure 20A:
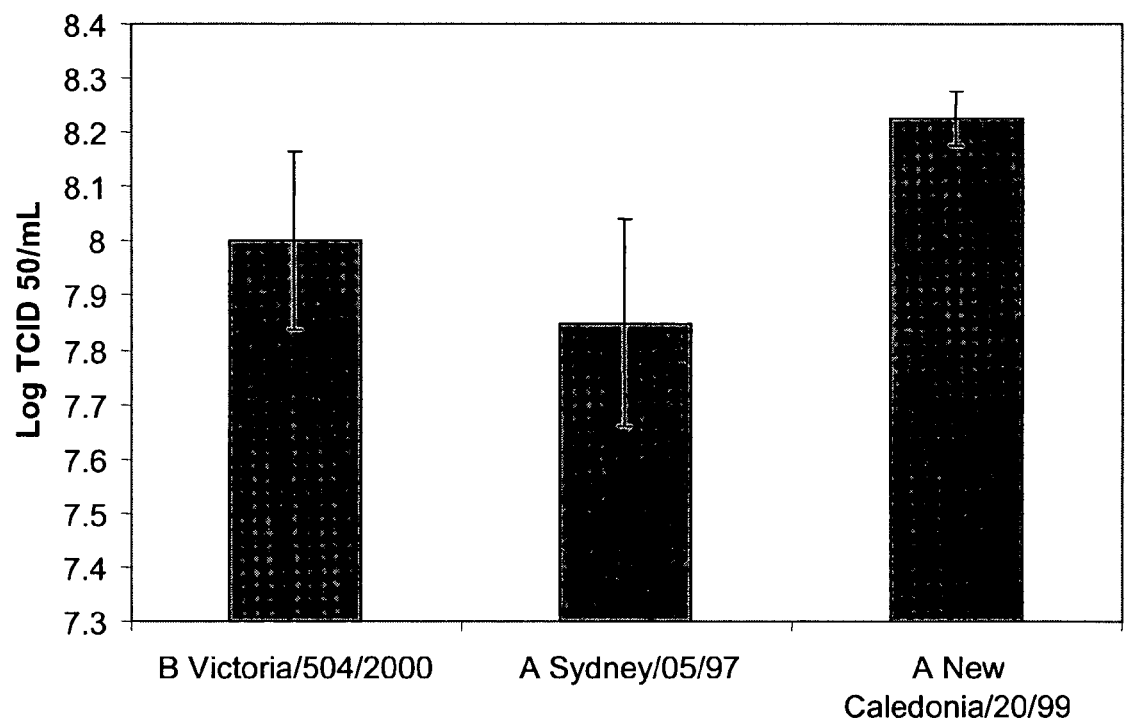
FIG. 20 Production Scale Growth and Purifiction. Panel A is a plot of the yield obtained for several vaccine reassortant strains, B/Victoria/504/2000 (~8 LogTCID 50/mL), A/Sydney/05/97 (~7.85 LogTCID 50/mL) and A/New Caledonia/20/99 (~8.2 LogTCID 50/mL), from 250 mL spinner flasks of MDCK-SF103 grown on Cytodex beads. Panel B outlines one cell culture scale up process which can be utilized for commercial scale production of vaccine material.
Figure 20B:
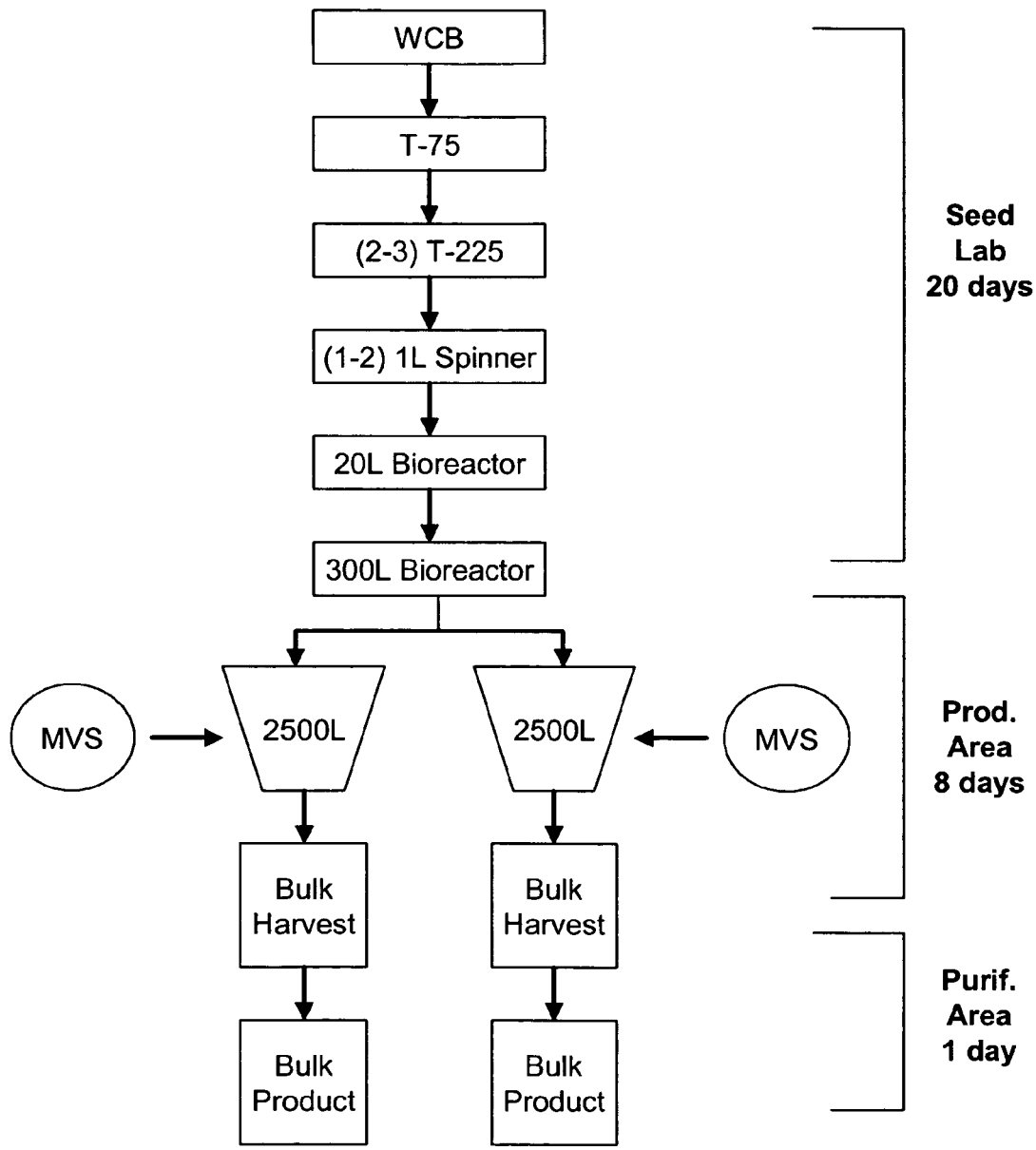

Use of a highly scalable microcarrier technology, similar to that used for the production of the currently licensed Polio vaccine, is applicable to the production of influenza in MDCK cells. Spherical beads made of dextran support excellent growth of MDCK cells and in 2 to 10 L bioreactors. Parental MDCK cells grown in SFMV 103 were found to be capable of growing on Cytodex 1 microcarriers to a density of $2 \times 10^6$ nuclei per mL in batch mode in both spinner flasks and MDCK cells have been grown to $>1 \times 10^6$ cell/mL in bioreactors up to a 10 L scale (data not shown). Initial pilot scale runs demonstrate that these MDCK cells are capable of producing vaccine influenza strains to high titer in a serum-free process and the titers were found to be equivalent or greater than the productivity obtained using serum grown cells in T-flasks. As shown in FIG. 20A, MDCK cells grown in Cytodex beads in 250 mL spinner flasks produced high titers of H1N1, H3N2 and B vaccine strains. For clinical manufacturing influenza virus may be produced in MDCK cells at the 20 L or 150 L scale, while commercial scale production may utilized 2,500 L bioreactors. FIG. 20B outlines one process that may be used for cell culture scale up to commercial production levels. The working cell bank is first expanded sequentially from a T-75 flask to T-225 flasks to 1 liter spinner flasks to a 20 liter then 300 liter bioreactors which are finally expanded to a 2500 liter bioreactor. When the optimal cell density is obtained the culture in inoculated with the master viral strain. The virus is then bulk harvested from the culture supernatant.

The purification process for cell culture based influenza vaccines is modeled on purification of egg-based influenza vaccines (see, e.g., PCT Publication WO 05/014862 and PCT Patent Application PCT/US05/035614 filed Oct. 4, 2005). The purification of viral vaccine materials from cells may include any or all of the following processes, homogenation, clarification centrifugation, ultrafiltration, adsorption on barium sulfate and elution, tangential flow filtration, density gradient ultracentrifugation, chromatography, and sterilization filtration. Other purification steps may also be included. For example, crude medium from infected cultures can first be clarified by centrifugation at, e.g., 1000-2000×g for a time sufficient to remove cell debris and other large particulate matter, e.g., between 10 and 30 minutes. Alternatively, the medium is filtered through a 0.8 μm cellulose acetate filter to remove intact cells and other large particulate matter. Optionally, the clarified medium supernatant is then centrifuged to pellet the influenza viruses, e.g., at 15,000×g, for approximately 3-5 hours. Following resuspension of the virus pellet in an appropriate buffer, such as STE (0.01 M Tris-HCl; 0.15 M NaCl; 0.0001 M EDTA) or phosphate buffered saline (PBS) at pH 7.4, the virus may be concentrated by density gradient centrifugation on sucrose (60%-12%) or potassium tartrate (50%-10%). Either continuous or step gradients, e.g., a sucrose gradient between 12% and 60% in four 12% steps, are suitable. The gradients are centrifuged at a speed, and for a time, sufficient for the viruses to concentrate into a visible band for recovery. Alternatively, and for most large scale commercial applications, virus is elutriated from density gradients using a zonal-centrifuge rotor operating in continuous mode.

A feature which may included in the purification of viral vaccine materials from cells is the use of Benzonase®, a non-specific endonuclease, early in the process. While MDCK cellular DNA does not pose an oncogenic risk based on studies evaluating oncogenicity of cellular DNA, Benzonase® treatment would virtually eliminate any potential or hypothetical risk. In one purification process, following Benzonase® treatment, the material is clarified by direct flow filtration (DFF) which will also remove any residual intact mammalian cells in the bulk material. The filtered bulk is then concentrated by tangential flow filtration (TFF) prior to further purification steps. Purification methods including affinity chromatography as well as ion-exchange chromatography and/or hydroxyapatite which, have worked well for other viral systems are useful for cell culture based influenza vaccine production. The highly purified viral material obtained by the process developed is then utilized in the production of vaccine material. For example, for use in a live attenuated vaccine production (e.g., FluMist®) the viral material may be subjected to a buffer exchange by filtration into a final formulation followed by a sterilization step. Buffers useful for such a formulation may contain 200 mM sucrose and a phosphate or histidine buffer of pH 7.0-7.2 with the addition of other amino acid excipients such as arginine. If necessary for stabilization protein hydrolysates such as porcine gelatin may also be added. Ideally the vaccine material is formulated to be stable for an extended storage time. One method which may be utilized to extend storage time is spray drying, a rapid drying process whereby the formulation liquid feed is spray atomized into fine droplets under a stream of dry heated gas. The evaporation of the fine droplets results in dry powders composed of the dissolved solutes (see, e.g., US Patent Publication 2004/0042972). Spray drying offers the advantages of ease of scalability and manufacturing cost as compared to conventional freeze-drying processes. Alternatively, the vaccine material is formulated to be stable as a refrigerator stable liquid formulation using methods known in the art. For example, methods and compositions for formulating a refrigerator stable attenuated influenza vaccine are described in PCT Patent Application PCT/US2005/035614 filed Oct. 4, 2005.

In-process characterization steps are incorporated into the purification scheme to monitor the production. Characterization steps which may be utilized include but are not limited to Fluorescent Focus Assay (FFA, see, e.g., above) which uses a simple antibody binding and fluorescent staining method to determine virus infectivity. Total protein and DNA determination which may be performed using numerous methods known to one of skill in the art are used to determine the percent of the initial impurities remaining. The specific activity of the preparation may be determined by calculating the viral infectivity per quantity of vaccine (e.g., infectivity/mg).

Example 8

Preclinical Animal Models

The ferret is a robust animal model used to evaluate the attenuation and immunogenicity of attenuated influenza vaccines and component vaccine strains. The performance of cell derived influenza strains produced from the MCB are compared to the same strains produced in eggs. Head to head comparison of these materials in controlled studies enables a high level of assurance of the comparability of these viral products.

In order to evaluate the ability of the two vaccines to infect or achieve a "take" in the ferret, animals are lightly anesthetized and inoculated intranasally with either the cell or egg produced viral preparations. Nasal wash material is collected at several time points following inoculation and the quantity of virus is evaluated by one of several available methods in order to evaluate the kinetics and extent of viral replication in the animals' upper respiratory tract. Experiments are performed with a range of doses and include multiple strains and different trivalent mixtures to generalize the relative infectivity of cell culture grown strains to egg produced strains. These same studies are also used to evaluate the immunogenicity of the influenza strains, a property that is inherently linked to the ability of the virus to initiate infection. Animals are bled and nasal washes are harvested at various points (weeks) post inoculation; these specimens are used to assess the serum antibody and nasal IgA responses to infection. The culmination of these data, infectivity, serum antibody and mucosal antibody responses, will be used to compare and evaluate the relative infectivity of the cell-produced vaccine to the egg produced vaccine. The most likely outcome is predicted to be that the cell and egg produced vaccine strains have similar infectivity and immunogenicity. If the cell derived vaccine appeared to be more infective or more immunogenic than the egg-derived product, further studies evaluating the possibility of lower dosage are performed.

A number of immunogenicity and replication studies are performed in the ferret model to evaluate the cell culture-derived vaccines with a single unit human dose. Infection with ca/ts/att strains generally elicits strong and rapid antibody responses in ferrets. In addition, individual ca/ts/att strains are routinely tested and shown to express the attenuated (att) phenotype by replicating to relatively high titers in the nasopharynx but to undetectable levels in the lung of these animals. The impact of cell culture growth on these biological traits is also assessed. However, it is unlikely that any differences will be seen, since the att phenotype is an integral part of the genetic composition of these strains. The growth kinetics and crossreactivity of these strains is evaluated following administration of a single human dose in these animals. Live attenuated vaccines generated from egg derived material elicit serum antibodies that cross-react with multiple strains within a genetic lineage; and it is expected that a cell-derived vaccine will have the same capability.

These comparability evaluations should provide significant insight into potential biochemical and/or biophysical differences of the primary virus product and demonstrate the impact of these epigenetic differences on the performance of the ca/ts/att strains measured by first passaging the virus in human cells or animal studies. Based on the sequence information to date, there is no expected impact on the ca/ts/att strains immunogenic performance resulting from production on MDCK cells.

Ferrets are a well document animal model for influenza and are used routinely to evaluate the attenuation phenotype and immunogenicity of ca/ts/att strains. In general, 8-10 week old animals are used to assess attenuation; typically study designs evaluate n=3-5 animals per test or control group. Immunogenicity studies are evaluated in animals from 8 weeks to 6 months of age and generally require n=3-5 animals per test article or control group. These numbers provide sufficient information to obtain statistically valid or observationally important comparisons between groups. During most studies Influenza-like signs may be noticed, but are not likely. Ferrets do not display signs of decrease in appetite or weight, nasal or ocular discharge; observing signs of influenza-like illness is a necessary part of the study and interventions such as analgesics are not warranted. Other signs of discomfort, such as open sores or significant weight loss, would result in appropriate disposition of the animal following discussion with the attending veterinarian.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A cell culture composition comprising non-tumorigenic MDCK cells, wherein said non-tumorigenic MDCK cells are of the MDCK-SF 103 cell line deposited as ATCC Accession Number PTA-6503.

2. A non-tumorigenic MDCK cell line selected from the group consisting of: MDCK-S deposited as ATCC Accession Number PTA-6500; and MDCK-SF 103 deposited as ATCC Accession Number PTA-6503.

3. The cell culture composition of claim 1, wherein said non-tumorigenic MDCK cells are non-tumorigenic in an adult nude mouse model.

4. The cell culture composition of claim 1, wherein said non-tumorigenic MDCK cells remain non-tumorigenic after at least 20 passages.

5. The non- tumorigenic MDCK cell line of claim 2, wherein said cell line is MDCK-S deposited as ATCC Accession Number PTA-6500.

6. The non- tumorigenic MDCK cell line of claim 2, wherein said cell line is MDCK-SF 103 deposited as ATCC Accession Number PTA-6503.

7. The non- tumorigenic MDCK cell line of claim 2, wherein said cell line is non-tumorigenic in an adult nude mouse model.

8. The non- tumorigenic MDCK cell line of claim 2, wherein said cell line remains non-tumorigenic after at least 20 passages.

* * * * *